US012681004B1

(12) United States Patent
Reynard

(10) Patent No.: US 12,681,004 B1
(45) Date of Patent: Jul. 14, 2026

(54) METHODS AND SYSTEMS FOR MULTIMODAL MEASUREMENT, FORECASTING, AND MODULATION OF AQUEOUS OUTFLOW

(71) Applicant: Michael Reynard, Santa Monica, CA (US)

(72) Inventor: Michael Reynard, Santa Monica, CA (US)

(*) Notice: Subject to any disclaimer, the term of this patent is extended or adjusted under 35 U.S.C. 154(b) by 0 days.

(21) Appl. No.: 19/371,168

(22) Filed: Oct. 28, 2025

(51) Int. Cl.
| | |
|---|---|
| *G01N 33/483* | (2006.01) |
| *G01N 21/49* | (2006.01) |
| *G01N 21/65* | (2006.01) |
| *G16B 25/00* | (2019.01) |

(52) U.S. Cl.
CPC ......... *G01N 33/4833* (2013.01); *G01N 21/49* (2013.01); *G01N 21/65* (2013.01); *G16B 25/00* (2019.02)

(58) Field of Classification Search
None
See application file for complete search history.

(56) References Cited

U.S. PATENT DOCUMENTS

| | | | |
|---|---|---|---|
| 7,094,225 B2 | 8/2006 | Tu et al. | |
| 7,508,524 B2 | 3/2009 | Mahadevan-Jansen et al. | |
| 8,447,526 B2 * | 5/2013 | Weng ..................... | G16B 40/10 703/11 |
| 9,506,907 B2 | 11/2016 | Bergkvist et al. | |
| 10,314,742 B2 | 6/2019 | Badawi et al. | |
| 11,071,647 B2 | 7/2021 | Berlin | |
| 11,318,047 B2 | 5/2022 | Berlin | |
| 2009/0021724 A1 | 1/2009 | Mahaevan-Jansen et al. | |
| 2025/0236843 A1 | 7/2025 | Segal et al. | |

FOREIGN PATENT DOCUMENTS

WO WO-2005016418 A1 * 2/2005 ......... A61F 9/00781

OTHER PUBLICATIONS

Lu R. Human ocular fluid outflow on-chip reveals trabecular meshwork-mediated Schlemm's canal endothelial dysfunction in steroid-induced glaucoma. Nature Cardiovascular Research 4: 1066-1076. (Year: 2025).*

Apostolidi A. Advances in Modeling the Inner Blood-Retinal Barrier: From Static Tissue Cell Cultures to Microphysiological Systems. Pharmaceuticals 18(1374): 27 pgs. (Year: 2025).*

Ding F. Classification of Whole-Slide Pathology Images Based on State Space Models and Graph Neural Networks. Electronics 14(2056): 22 pgs. (Year: 2025).*

Zhang B. Organ-on-a-chip devices advance to market. Lab Chip 17: 2395-2420. (Year: 2017).*

Wang F. Uncertainty in graph neural networks: a survey. arXiv 2403(07185): 20 pgs. (Year: 2025).*

Coca-Lopez N. Artificial Intelligence-Powered Raman Spectroscopy through Open Science and Fair Principles. ACS Nano 19: 38189-38218. (Year: 2025).*

Cornell University News. "'Eye on a chip' reveals trigger for steroid induced glaucoma." Cornell Chronicle, Aug. 30, 2025. Press summary of Lu et al.

Technology Networks Editorial. "Eye on a Chip Identifies Cause of Steroid Induced Glaucoma." Technology Networks, Aug. 28, 2025. Secondary coverage.

Koornwinder A.; Zhang Y.; Ravindranath R.; Chang R. T.; Bernstein I. A.; Wang S. Y. "Multimodal Artificial Intelligence Models Predicting Glaucoma Progression Using Electronic Health Records and Retinal Nerve Fiber Layer Scans." Translational Vision Science & Technology, Mar. 3, 2025. DOI: 10.1167/tvst.14.3.27; PMID: 40152766; PMCID: PMC11954538.

Núñez R.; Vérticchio A.; Rowe L.; et al. "Artificial Intelligence to Aid Glaucoma Diagnosis and Monitoring: State of the Art and New Directions." Photonics 9(11):810, Oct. 28, 2022. DOI: 10.3390/photonics9110810.

Prabhakar B.; et al. "Artificial intelligence (AI) impacting diagnosis of glaucoma: a review." Seminars in Ophthalmology, 2021. ScienceDirect record.

Coan L. J.; Williams B. M.; et al. "Automatic detection of glaucoma via fundus imaging and artificial intelligence: A review." Survey of Ophthalmology 68(1):17-41, 2023. DOI: 10.1016/j.survophthal. 2022.08.005; PMID: 35985360.

Rogers T. W.; et al. "Evaluation of an AI system for the automated detection of glaucoma from stereoscopic optic disc photographs." arXiv 1906.01272, 2019. Preprint.

Chayan T. I.; Islam A.; Rahman E.; Reza M. T.; Apon T. S.; Alam M. G. R. "Explainable AI based Glaucoma Detection using Transfer Learning and Lime." arXiv 2210.03332, 2022. Preprint.

Kim J, Park DY, Bae H, Park DY, Kim D, Lee CK, Song S, Chung TY, Lim DH, Kubota Y, Hong YK, He Y, Augustin HG, Oliver G, Koh GY. Impaired angiopoietin/Tie2 signaling compromises Schlemm's canal integrity and induces glaucoma. J Clin Invest. Oct. 2, 2017;127(10):3877-3896. doi: 10.1172/JCI94668. Epub Sep. 18, 2017. PMID: 28920924; PMCID: PMC5617682.

(Continued)

*Primary Examiner* — Olivia M. Wise
*Assistant Examiner* — Robert J. Kallal
(74) *Attorney, Agent, or Firm* — Richard A Baker, Jr.

(57) ABSTRACT

A system and method for measuring, forecasting, and modulating aqueous outflow is described here. The system and method operate on an ocular microphysiological system that reproduces the trabecular-meshwork-membrane-Schlemm's canal interface under a defined hydrodynamic program. The signals may include TEER resistance, pressure-flow measurements, OCT/OCTA images, and Raman spectra. The Ocular MPS system may include encoding the multimodal signals into a device-agnostic feature representation that includes descriptors of junction continuity, belt thickness, tortuosity, pathway activity, and outflow-resistance proxies. The Ocular MPS system may execute a physics-informed graph state-space model that fuses the device-agnostic feature representation into inferred parameters. The inferred parameters may be inferred from barrier integrity, permeability, and outflow facility, subject to monotonic constraints between structural and hydraulic variables. The Ocular MPS system may quantify uncertainty of inferred parameters, generating calibrated forecasts of aqueous outflow performance. The Ocular MPS system may control a drive actuator according to the calibrated forecasts.

30 Claims, 22 Drawing Sheets

(56) References Cited

OTHER PUBLICATIONS

Thomson, B.R., Liu, P., Onay, T. et al. Cellular crosstalk regulates the aqueous humor outflow pathway and provides new targets for glaucoma therapies. Nat Commun 12, 6072 (2021). https://doi.org/10.1038/s41467-021-26346-0.

Stamer, W.D., Lei, Y., Boussommier-Calleja, A., Overby, D.R., Ethier, C.R., eNOS, a pressure-dependent regulator of intraocular pressure. Invest Ophthalmol Vis Sci. 2011;52(13):9438-9444.

Ashpole, N.E., Overby, D.R., Ethier, C.R., Stamer, W.D. Shear stress-triggered nitric oxide release from Schlemm's canal cells. Invest Ophthalmol Vis Sci. 2014;55(12):8067-9706.

Lu R. "Eye-on-a-Chip Identifies Cause of Steroid-Induced Glaucoma." Technology Networks Cell Science, Aug. 28, 2025. downloaded from https://www.technologynetworks.com/cell-science/news/eye-on-a-chip-identifies-cause-of-steroid-induced-glaucoma-404012.

Lu R.; Kolarzyk A. M.; Lee E. "Human ocular fluid outflow on chip reveals trabecular meshwork mediated Schlemm's canal endothelial dysfunction in steroid induced glaucoma." Nature Cardiovascular Research (Letter), Aug. 27, 2025. Primary mechanism reference (ALK5/VEGFC).

* cited by examiner

START-UP / PRE-SHIFT CHECKS
402

TEER BLANK & AREA NORM
404

RAMAN 520.7 CM⁻¹ REF
406

SAFETY GATES (ΔP, SHEAR, LASER POWER/DWELL, CURRENT DENSITY)
408

OCT SCALE/FOCUS
410

BASELINE STABILITY
(<~10% DRIFT / 30 MIN)
412

ΔP-Q LINEARITY (OFF-CELL)
414

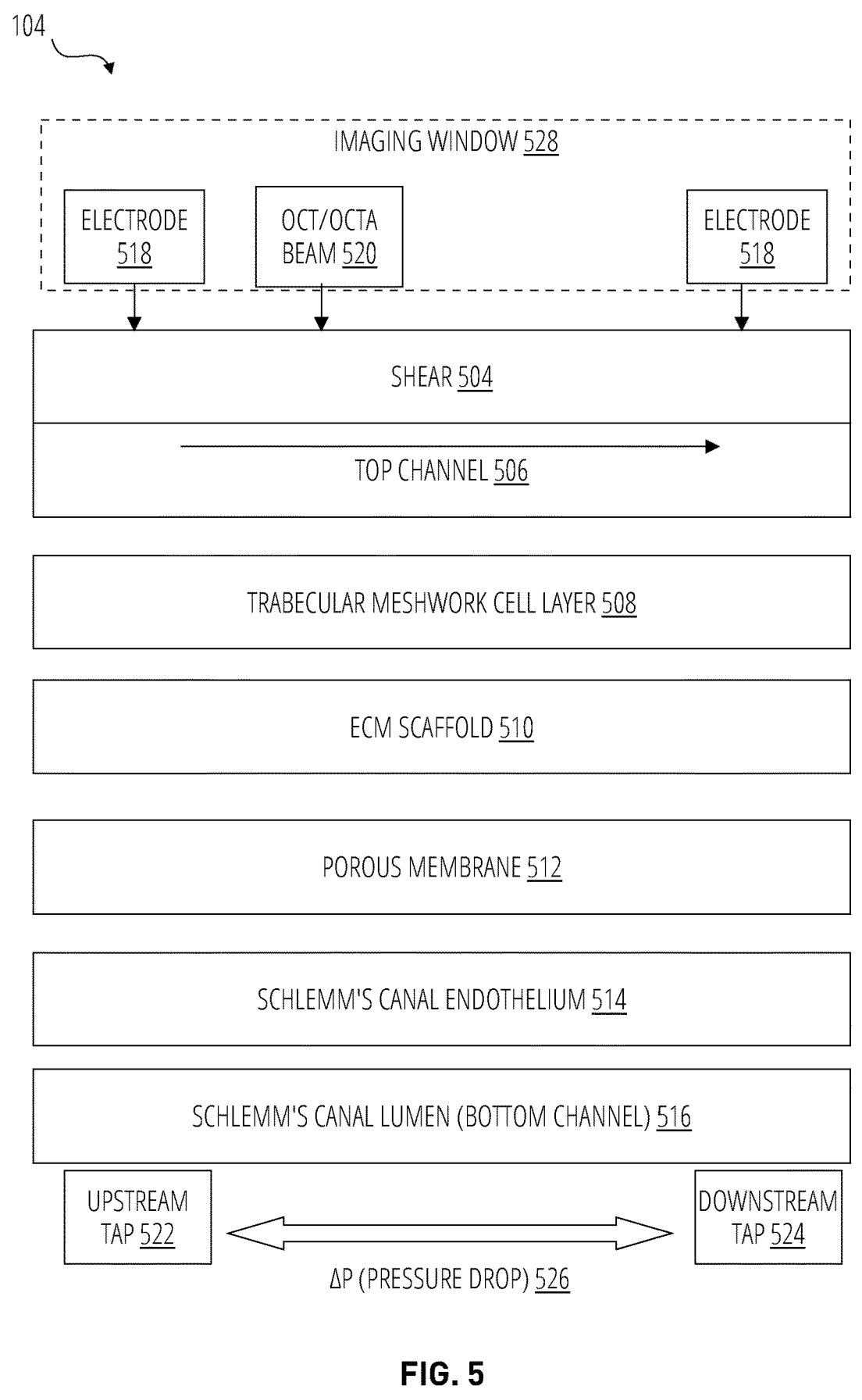

104

IMAGING WINDOW 528

| ELECTRODE 518 | OCT/OCTA BEAM 520 | | ELECTRODE 518 |

SHEAR 504

TOP CHANNEL 506

TRABECULAR MESHWORK CELL LAYER 508

ECM SCAFFOLD 510

POROUS MEMBRANE 512

SCHLEMM'S CANAL ENDOTHELIUM 514

SCHLEMM'S CANAL LUMEN (BOTTOM CHANNEL) 516

UPSTREAM TAP 522　　　　DOWNSTREAM TAP 524

ΔP (PRESSURE DROP) 526

FIG. 5

TIME T0
1312

TIME T1
1314

TIME T2
1316

TRABECULAR NETWORK
NODE
[ALK5, JUNCTION, PERM]
1302

SCHLEMM'S CANAL NODE
[VEGFC, JUNCTION, PERM]
1304

TRABECULAR NETWORK
NODE
[ALK5, JUNCTION, PERM]
1306

SCHLEMM'S CANAL NODE
[VEGFC, JUNCTION, PERM]
1318

CONSTRAINTS:
JUNCTION <–> HYDRAULIC
RESISTANCE PROXY
MONOTONE RELATIONS
1308

OUTPUTS:
FACILITY/PERMEABILITY
ΔFACILITY (WINDOW)
IOP TRAJECTORY
UNCERTAINTY SETS
1310

1502. Predicted vs Measured Facility

1504 Uncertainty Coverage

1506 Baseline Drift (TEER / Raman)

+10%

-10%

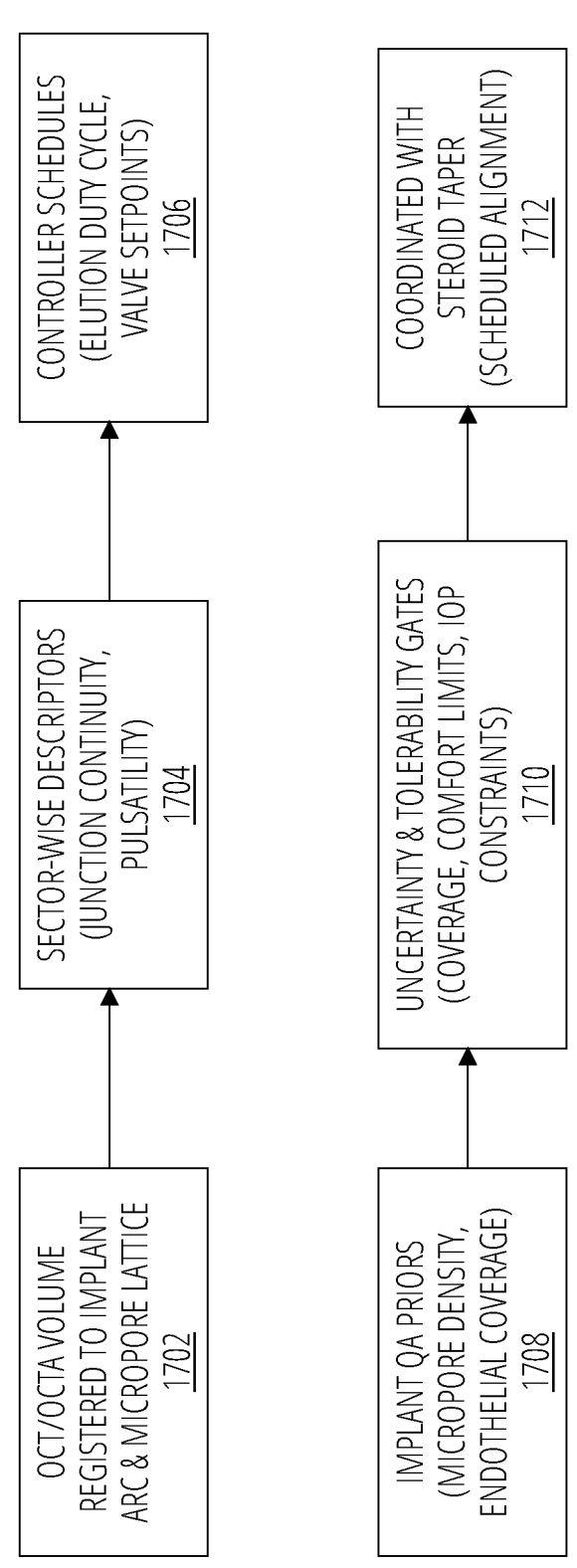

OCT/OCTA VOLUME REGISTERED TO IMPLANT ARC & MICROPORE LATTICE
1702

SECTOR-WISE DESCRIPTORS (JUNCTION CONTINUITY, PULSATILITY)
1704

CONTROLLER SCHEDULES (ELUTION DUTY CYCLE, VALVE SETPOINTS)
1706

IMPLANT QA PRIORS (MICROPORE DENSITY, ENDOTHELIAL COVERAGE)
1708

UNCERTAINTY & TOLERABILITY GATES (COVERAGE, COMFORT LIMITS, IOP CONSTRAINTS)
1710

COORDINATED WITH STEROID TAPER (SCHEDULED ALIGNMENT)
1712

FIG. 17

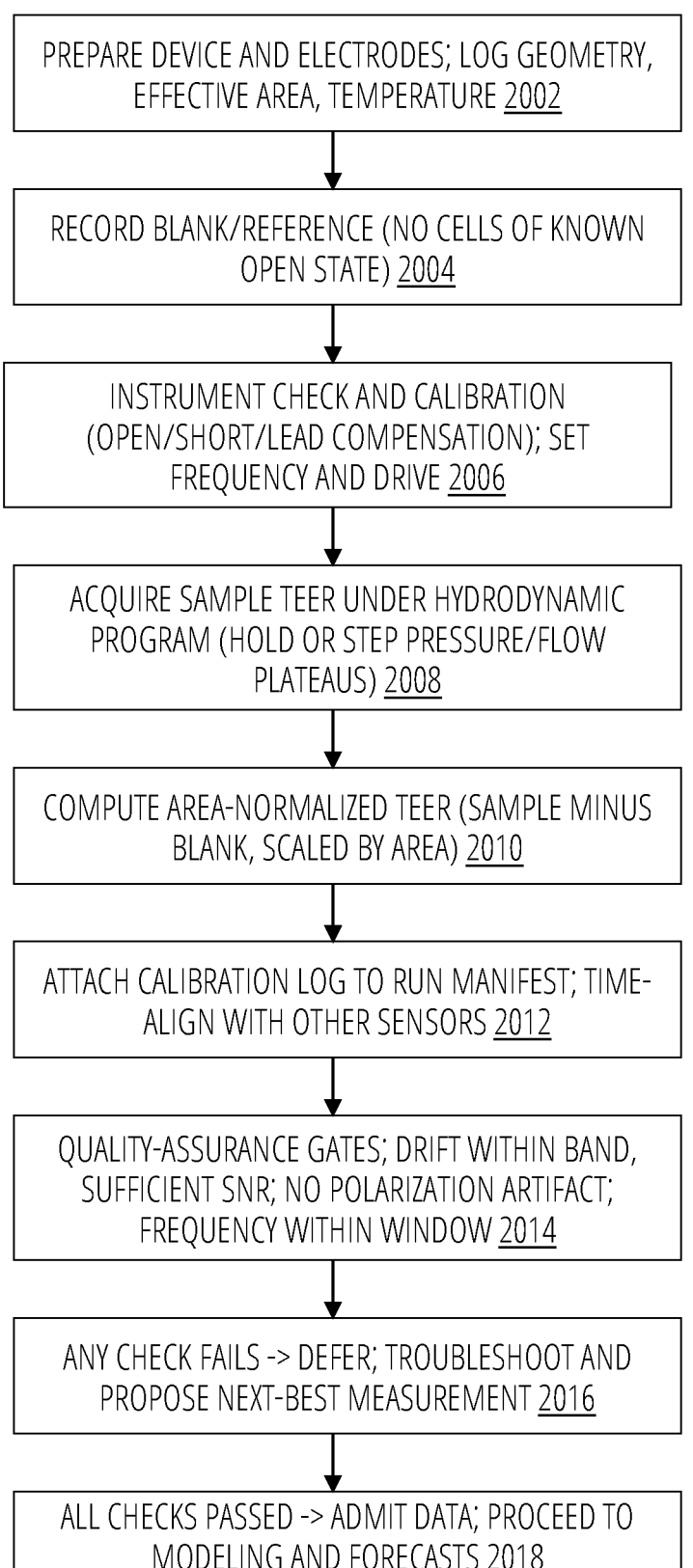

PREPARE DEVICE AND ELECTRODES; LOG GEOMETRY, EFFECTIVE AREA, TEMPERATURE 2002

RECORD BLANK/REFERENCE (NO CELLS OF KNOWN OPEN STATE) 2004

INSTRUMENT CHECK AND CALIBRATION (OPEN/SHORT/LEAD COMPENSATION); SET FREQUENCY AND DRIVE 2006

ACQUIRE SAMPLE TEER UNDER HYDRODYNAMIC PROGRAM (HOLD OR STEP PRESSURE/FLOW PLATEAUS) 2008

COMPUTE AREA-NORMALIZED TEER (SAMPLE MINUS BLANK, SCALED BY AREA) 2010

ATTACH CALIBRATION LOG TO RUN MANIFEST; TIME-ALIGN WITH OTHER SENSORS 2012

QUALITY-ASSURANCE GATES; DRIFT WITHIN BAND, SUFFICIENT SNR; NO POLARIZATION ARTIFACT; FREQUENCY WITHIN WINDOW 2014

ANY CHECK FAILS -> DEFER; TROUBLESHOOT AND PROPOSE NEXT-BEST MEASUREMENT 2016

ALL CHECKS PASSED -> ADMIT DATA; PROCEED TO MODELING AND FORECASTS 2018

FIG. 20

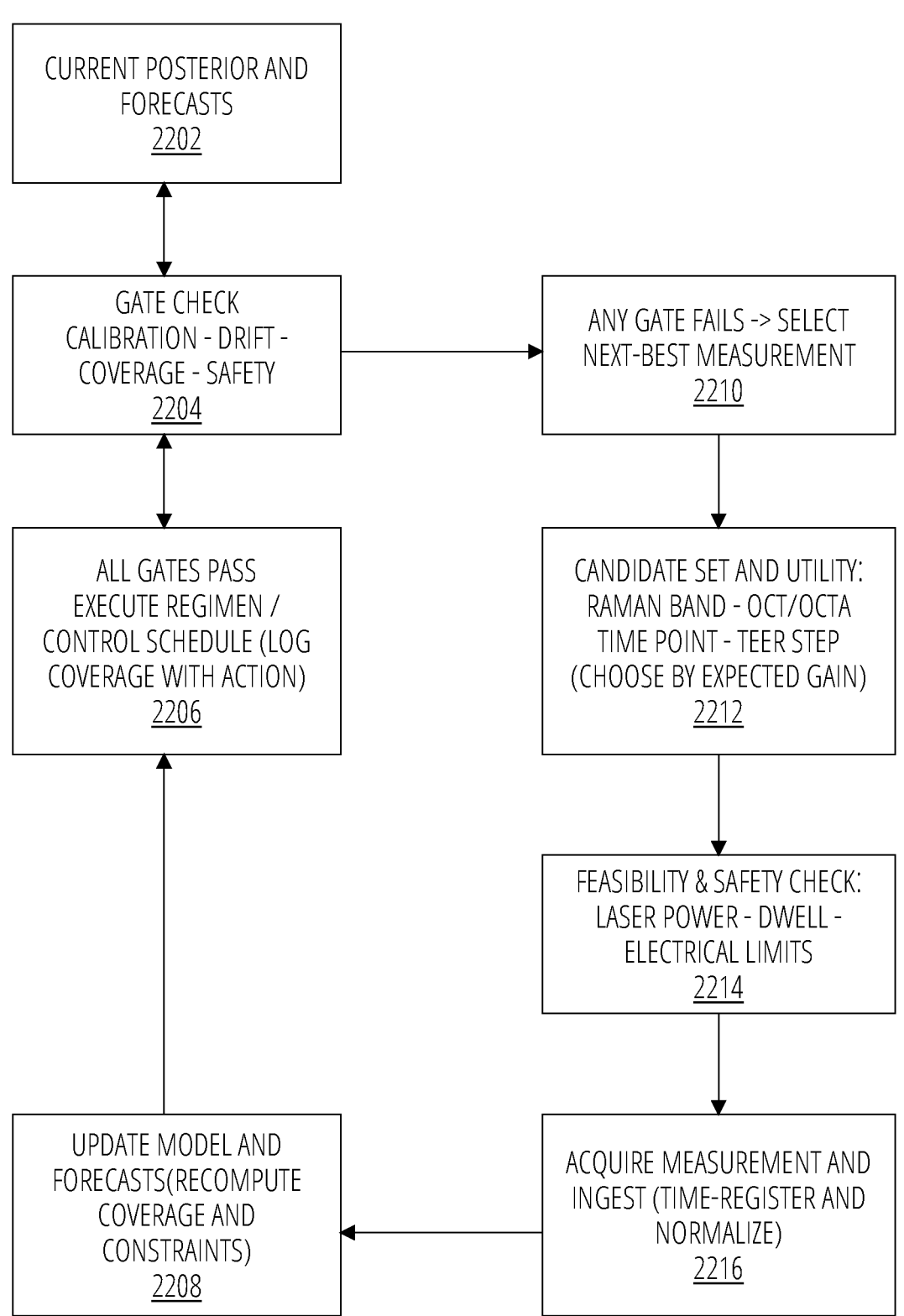

CURRENT POSTERIOR AND FORECASTS
2202

GATE CHECK CALIBRATION - DRIFT - COVERAGE - SAFETY
2204

ANY GATE FAILS -> SELECT NEXT-BEST MEASUREMENT
2210

ALL GATES PASS EXECUTE REGIMEN / CONTROL SCHEDULE (LOG COVERAGE WITH ACTION)
2206

CANDIDATE SET AND UTILITY: RAMAN BAND - OCT/OCTA TIME POINT - TEER STEP (CHOOSE BY EXPECTED GAIN)
2212

FEASIBILITY & SAFETY CHECK: LASER POWER - DWELL - ELECTRICAL LIMITS
2214

UPDATE MODEL AND FORECASTS(RECOMPUTE COVERAGE AND CONSTRAINTS)
2208

ACQUIRE MEASUREMENT AND INGEST (TIME-REGISTER AND NORMALIZE)
2216

FIG. 22

METHODS AND SYSTEMS FOR MULTIMODAL MEASUREMENT, FORECASTING, AND MODULATION OF AQUEOUS OUTFLOW

CROSS-REFERENCE TO RELATED APPLICATIONS

This is a priority application.

BACKGROUND

Field of the Inventions

The disclosure relates to microphysiological systems (MPS) for modeling ocular tissues, including platforms configured to study aqueous humor outflow across the trabecular meshwork (TM) and Schlemm's canal (SC). It further relates to measurement and analysis techniques for such systems, including label-free spectroscopy and data-driven evaluation.

Background of the Inventions

Ocular hypertension and primary open-angle glaucoma have been associated with altered resistance to aqueous outflow in the conventional pathway. Researchers have explored ex vivo perfusion of anterior segments, in vitro cultures of TM and SC cells on porous interfaces, and microfluidic "organ-on-chip" approaches to impose controlled pressure and shear.

In some embodiments, the Ocular MPS system 102 is evaluated and optimized using an ex-vivo ocular microphysiological system that reproduces the TM-SC stack under controlled hydrodynamics. A representative device includes a TM compartment, a porous TM-SC interface (e.g., track-etched PC or PET, 0.2-3 μm pores, 6-20 μm thickness; or a microfabricated SU-8 scaffold), and an SC channel with optical access. Perfusion and pressure control impose defined pressure drops (about 0-10 mmHg) and shear (about 0.5-5 dyn·cm$^{-2}$).

Embedded or adjacent electrodes acquire TEER and impedance data, while Raman spectroscopy (e.g., near-infrared excitation with approximately 4-10 cm$^{-1}$ resolution) and optical coherence tomography (OCT), optical coherence tomography angiography (OCTA), or microscopy provide co-registered biochemical and structural readouts correlated to ΔP and shear. The acquired signals are time-stamped, normalized, and integrated through physics-informed analytics to estimate permeability and outflow facility, guiding dosing or genetic and pharmacologic modulation. This framework is device-agnostic across substrates and geometries, supporting iterative optimization of the therapies disclosed herein.

While these efforts have advanced understanding of cellular mechanics, junctional integrity, and transport, existing approaches can suffer from variability in scaffold composition and geometry, limited standardization of readouts across devices, and challenges in monitoring biochemical state at the TM-SC interface under physiologic load. Electrical and hydraulic measurements (e.g., TEER, permeability, pressure-flow) quantify barrier function and facility but do not, by themselves, resolve concurrent molecular changes within cells and matrix. In addition, data generated on one platform may not readily translate to another due to differences in materials, pore structures, hydrodynamics, or sensor placement, complicating comparison, meta-analysis, and the training of generalized computational models.

Steroid-induced glaucoma represents a clinically significant complication of corticosteroid therapy, leading to increased intraocular pressure (IOP) and irreversible optic nerve damage if left untreated. The mechanism underlying this phenomenon has recently been clarified through micro-engineered platforms, showing that corticosteroid exposure activates ALK5 receptors in trabecular meshwork (TM) cells, which in turn downregulates vascular endothelial growth factor C (VEGFC) signaling in Schlemm's canal (SC) endothelial cells. This results in abnormal tightening of endothelial junctions, impaired aqueous humor outflow, and subsequent elevation of IOP.

No work to date on this subject integrates AI with chip-based molecular and microfluidic platforms, nor does it leverage AI to model mechanistic disruptions in the ALK5/VEGFC axis or guide drug, genetic, and cellular interventions.

Accordingly, there remains a need for systems and methods that: (i) provide controlled, reproducible microenvironments at the TM-SC interface; (ii) enable noninvasive, in-situ biochemical readouts during applied pressure and shear; and (iii) support unified analysis frameworks that fuse heterogeneous signals across platforms to estimate barrier function, outflow facility, and treatment response with improved reliability. The Ocular MPS system 102 addresses this gap with a novel, mechanistically anchored, AI-driven system.

BRIEF SUMMARY

In one aspect, a method for measuring, forecasting, and modulating aqueous outflow, includes providing an ocular microphysiological system reproducing a trabecular-meshwork-membrane-Schlemm's-canal interface under a defined hydrodynamic program includes pressure-drop and shear waveforms, acquiring synchronized multimodal signals from said ocular microphysiological system including TEER resistance, pressure-flow measurements, OCT/OCTA images, and Raman spectra, encoding said multimodal signals into a device-agnostic feature representation includes descriptors of junction continuity, belt thickness, tortuosity, pathway activity, and outflow-resistance proxies, executing a physics-informed graph state-space model that fuses the device-agnostic feature representation into inferred parameters, the inferred parameters are inferred from barrier integrity, permeability, and outflow facility subject to monotonic constraints between structural and hydraulic variables, quantifying uncertainty of inferred parameters, generating calibrated forecasts of aqueous outflow performance, and controlling a drive actuator according to the calibrated forecasts only when uncertainty, calibration, and safety gates are satisfied.

The defined hydrodynamic program may impose a pressure drop of 0-10 mm Hg and shear stress of 0.5-5 dyn·cm$^{-2}$. The method may also include performing electrical calibration and optical wavelength calibration prior to acquisition. The Raman spectra may be acquired with near-infrared excitation at approximately 785 nm and spectral resolution of 4-10 cm$^{-1}$. The physics-informed graph state-space model may represent trabecular-meshwork and Schlemm's canal compartments as coupled nodes exchanging mechanical and biochemical messages. The observation that monotonic constraints enforce that increases in junction continuity or VEGFC signaling decrease hydraulic resistance, whereas increases in ALK5 signaling increase resistance. The quantifying of uncertainty may employ conformal prediction to establish coverage probabilities. The method may also include an active-learning controller that selects a next measurement configuration when uncertainty exceeds a defined threshold.

The safety gates may restrict laser power, electrode current density, and maximum pressure drop. The ocular microphysiological system may include a porous membrane between the trabecular-meshwork and Schlemm's canal chambers fabricated from polycarbonate. The method may also include cross-MPS normalization that maps heterogeneous device outputs into a common latent space. The modulation includes pharmacologic intervention targeting ALK5/TGF-β pathways. The forecasts and control decisions are stored with model version, calibration record, and gate outcomes.

In one aspect, a system for multimodal measurement, forecasting, and modulation of aqueous outflow, includes an ocular microphysiological device including a trabecular-meshwork compartment, a porous membrane, and a Schlemm's-canal channel with inlet and outlet ports. The system for multimodal measurement also includes a plurality of synchronized sensors connected to the ocular microphysiological device, the plurality of synchronized sensors configured to measure TEER, pressure-flow pairs, OCT/OCTA data, and Raman spectra into synchronized sensor data. The system for multimodal measurement also includes a timing hub configured to align the synchronized sensor data to a common clock into a multimodal feature set. The system for multimodal measurement also includes a computing module executing a physics-informed graph state-space model trained to infer barrier integrity, permeability, and outflow facility from the multimodal feature set into model forecasts. The system for multimodal measurement also includes a controller configured to control a drive actuator based on the model forecasts only when calibration, uncertainty, and safety gates are satisfied.

The computing module may apply device-agnostic encoders normalizing geometry, temperature, and sampling cadence. The drive actuator may include a dosing pump configured for closed-loop regulation of pressure and flow. The system may also include a calibration subsystem performing TEER blank correction, Raman wavelength alignment, and OCT scale verification. The physics-informed graph state-space model may include monotone constraints coupling junction features to hydraulic resistance. The uncertainty and safety gates may be implemented as acceptance metrics for coverage, drift, and power thresholds. The ocular microphysiological device may further include optical windows allowing simultaneous OCT/OCTA and Raman interrogation. The system may also include a data logger that records calibration artifacts, model parameters, and control histories for regulatory audit. The computing module may execute active-learning logic selecting a next-best measurement. The plurality of synchronized sensors and the controller are network-connected to permit federated learning across multiple laboratory or clinical sites. The corticosteroid challenge may elevate ALK5 activity and forecast facility recovery under an ALK5 inhibitor regimen.

In one aspect, a non-transitory computer-readable medium storing instructions that, when executed by one or more processors, cause the one or more processors to receive synchronized electrical, hydraulic, optical, and spectroscopic data from an ocular microphysiological system, encode the synchronized electrical, hydraulic, optical, and spectroscopic data into device-agnostic features, apply a physics-informed graph state-space model on the device-agnostic features to estimate barrier integrity, permeability, and outflow facility with uncertainty, and output dosing schedules when calibration, uncertainty, and safety criteria are satisfied.

The instructions may further cause adaptive updating of model parameters based on calibration results or longitudinal drift. The physics-informed graph state-space model may employ monotonicity regularization and causal constraints derived from fluid-structure relations. The uncertainty quantification may use Bayesian techniques to define prediction intervals. The instructions may interface with an electronic laboratory notebook to export standardized diagnostic reports. The instructions may further cause computation of ALK5 and VEGFC signaling indices from Raman or omics features to forecast therapeutic response. Other technical features may be readily apparent to one skilled in the art from the following figures, descriptions, and claims.

BRIEF DESCRIPTION OF THE DRAWINGS

To easily identify the discussion of any particular element or act, the most significant digit or digits in a reference number refer to the figure number in which that element is first introduced.

FIG. 5 illustrates an ocular MPS cross-section with hydrodynamic loading and optical access (illustrative).

FIG. 17 illustrates implant-registered sector control.

FIG. 20 is a flowchart of a TEER calibration and measurement workflow.

FIG. 22 shows a flowchart of the active learning flow under governance gates.

DETAILED DESCRIPTION

Figure 1:
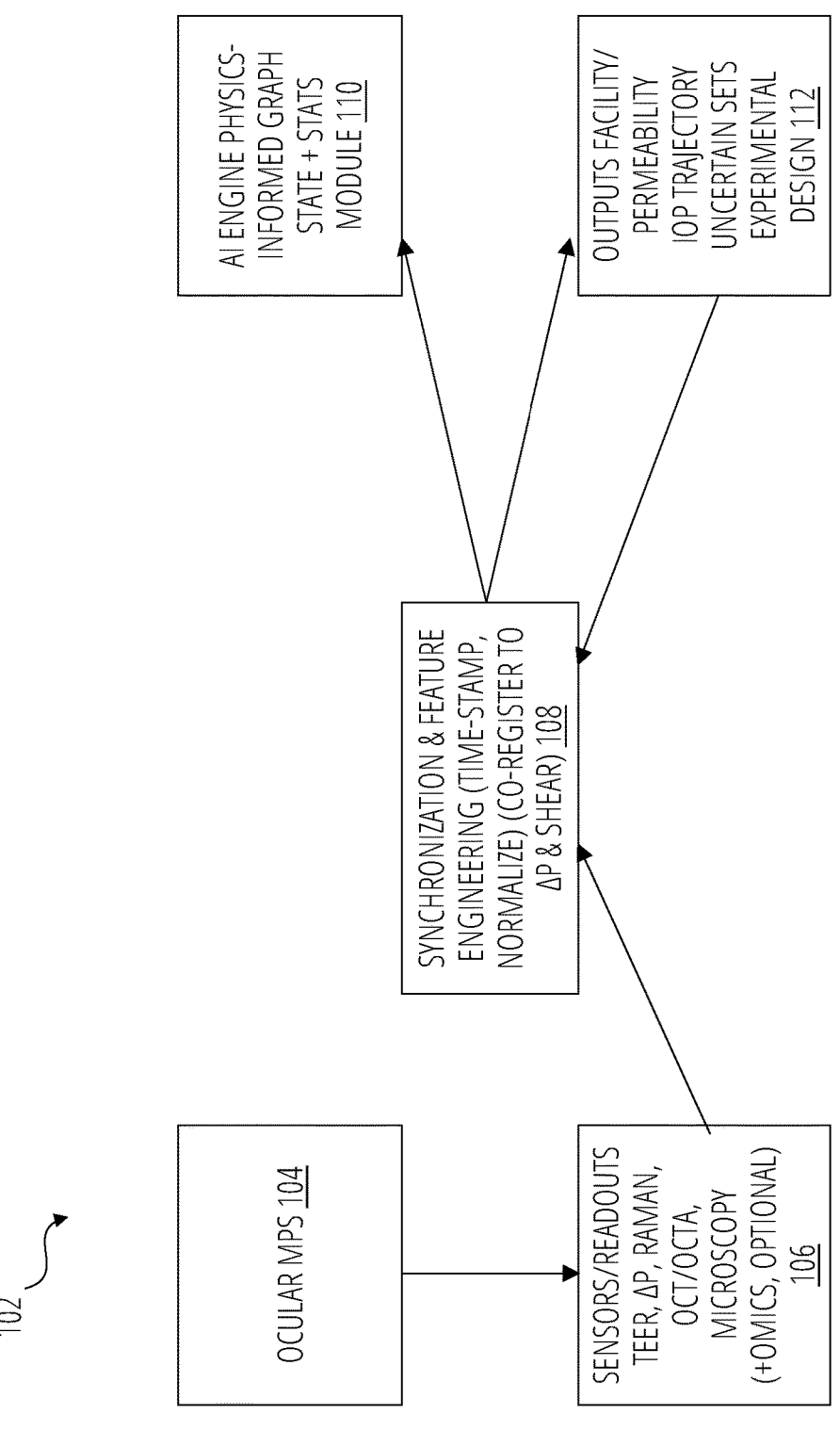
FIG. 1 depicts the system architecture linking the ocular MPS to multimodal acquisition (TEER, ΔP-Q, OCT/OCTA, Raman), feature encoders, a physics-informed learning model, and an optimizer/controller that outputs dosing or perfusion commands with safety and QA gating.

Disclosed are methods, systems, and computer-readable media for measuring, forecasting, and modulating aqueous outflow using ocular microphysiological systems (MPS) operated under controlled hydrodynamic loading. In various embodiments, a device that reproduces the trabecular-mesh-work (TM)-membrane-Schlemm's-canal (SC) interface is subjected to defined pressure drops ($\Delta P$) and shear while synchronized, multimodal signals are acquired, including (i) electrical measurements of transepithelial/endothelial resistance (TEER), (ii) pressure-flow pairs ($\Delta P$-Q), (iii) optical coherence tomography (OCT/OCTA) and/or brightfield imaging, and (iv) Raman spectra. Modality-specific features are registered to loading conditions and fused to estimate barrier integrity, permeability, and outflow facility.

In certain embodiments, a physics-informed learning framework, such as a graph state-space model with modality encoders, produces facility and permeability estimates with calibrated uncertainty, supports hypothesis testing, and enables closed-loop control. The framework may schedule additional measurements when uncertainty exceeds thresholds, apply acceptance/QA criteria to gate decisions, and optimize actuation (e.g., perfusion profiles or dosing schedules) subject to predefined safety limits on pressure, shear, illumination, and electrode current density.

The platforms are device-agnostic and support multiple scaffolds, membranes, and cartridge geometries, as well as ex vivo preparations and, where appropriate, clinical analytics based on co-registered imaging and sensor streams. Cross-MPS normalization allows results to be compared across hardware variants and laboratories.

Illustrative embodiments include mechanistic perturbations and regimen design involving transforming growth factor-$\beta$/ALK5 signaling and VEGF-C pathways; however, the disclosed systems and methods are not limited to any particular pathway, agent, or scaffold and may be applied to pharmacologic, genetic, or mechanical interventions.

The disclosure discusses a synchronized, hydrodynamically loaded measurement and control pipeline that acquires co-registered multimodal signals from an ocular microphysiological system and/or the clinic; encodes those signals into a device-agnostic feature space; infers barrier integrity, permeability, and outflow facility by means of a physics-informed graph state-space model with monotonic constraints linking junction descriptors to hydraulic resistance; and produces calibrated forecasts and action recommendations whose execution is gated by uncertainty and safety criteria. These embodiments may include calibration/QA sequences, ALK5/VEGFC perturbation studies, dose-schedule optimization, and implant-registered sector control, regardless of scaffold, sensor subset, actuator type, or clinical setting, because the embodiments may practice a synchronized acquisition to a physics-constrained inference to an uncertainty-gated decision loop.

Outflow Regulation by ALK/VEGFC

This section describes ALK (with emphasis on ALK5/TGF$\beta$R1) and VEGFC/VEGFR3 signaling at the trabecular meshwork-Schlemm's canal (TM-SC) interface, including their biomechanical context, mutual crosstalk, temporal dynamics, and consequences for junctional architecture, permeability, and outflow.

Without limiting to any particular mechanism, the TM-SC interface may be viewed as a coupled, load-responsive epithelium-endothelium system in which transforming growth factor-$\beta$ (TGF$\beta$) signaling through Activin receptor-like kinases, particularly ALK5/TGF$\beta$R1, tends to promote barrier tightening and extracellular-matrix (ECM) accumulation, whereas vascular endothelial growth factor-C (VEGFC) signaling through VEGFR3/FLT4 in Schlemm's canal supports a lymphatic-like endothelial identity associated with junctional patency and facilitated fluid entry into the canal. These axes operate under hydrodynamic load; pressure drop ($\Delta P$) across the TM-membrane-SC stack 506, 508, 512, 516 and shear over the TM and along the canal are not merely boundary conditions but active inputs that modulate receptor availability, cytoskeletal tone, nuclear mechanotransduction, and therefore the net balance between tightening and loosening programs.

On the TM side, canonical TGF$\beta$ engages a type-II receptor that recruits and activates ALK5, which phosphorylates SMAD2/3. The SMAD2/3-SMAD4 complex translocates to the nucleus and remodels gene expression toward ECM production and cytoskeletal reinforcement, including increased transcription of collagens and fibronectin, induction of connective-tissue growth factor, and upregulation of plasminogen-activator inhibitors that reduce matrix turnover. In parallel, non-canonical branches engage RhoA/ROCK, p38/JNK, and PI3K/AKT signaling, further stabilizing actin stress fibers and focal adhesions. The combined effect is increased TM stiffness, enhanced cell-substrate coupling, and reinforcement of junctional complexes at the juxtacanalicular region, which together reduce effective pore formation and elevate hydraulic resistance.

Corticosteroid exposure can amplify this program by increasing TGF$\beta$ pathway tone and altering glucocorticoid-responsive cytoskeletal genes, thereby shifting the set point toward tighter junctions and higher outflow resistance. Load accentuates this shift: elevated $\Delta P$ transmits strain across the microporous interface and ECM, promotes nuclear localization of YAP/TAZ and other mechanosensors that synergize with SMAD2/3, and accelerates a positive feedback loop in which stiffening begets additional stiffening and reduced facility.

On the SC side, VEGFC is synthesized as a precursor that is processed to its mature, high-affinity form and binds VEGFR3 (with co-receptors such as NRP2), activating intracellular cascades that include PI3K/AKT and ERK. In Schlemm's canal endothelium this signaling reinforces a lymphatic-like phenotype marked by PROX1 and related transcriptional programs. Functionally, VEGFC/VEGFR3 activity promotes junctional configurations compatible with fluid ingress, supports transcellular vacuole and pore dynamics under load, and maintains responsiveness to shear cues through KLF2/KLF4 and nitric-oxide synthase pathways. The net effect is a loosening or patterning of junctions that allows aqueous humor to enter the canal with lower resistance, often accompanied by subtle re-arrangements of VE-cadherin/ZO-1 belts and cortical actin that maintain barrier selectivity without imposing an impermeable seal. Shear along the canal further augments VEGFC-responsive signaling, stabilizing PROX1 expression and increasing endothelial compliance to cyclical loading, which in turn sustains vacuolation and valve-like behaviors at physiologic ΔP.

Antagonism between these axes creates a tunable balance at the interface. Increased ALK5 tone in TM and the adjacent interface tends to suppress junctional permeability and, through paracrine and mechanical feedback, can diminish VEGFC availability or VEGFR3 responsiveness in SC endothelium. Conversely, sustained VEGFC signaling in SC can counter junctional tightening by preserving a lymphatic-like program and enhancing shear-adaptive traits that favor fluid entry.

Crosstalk operates at multiple layers: transcriptional (e.g., PROX1 and SMAD-dependent target sets with opposing effects on junctional architecture), post-translational (e.g., RhoA/ROCK-mediated cytoskeletal tension vs. AKT-mediated relaxation), and biomechanical (e.g., ECM-driven stiffness versus shear-induced nitric-oxide production). Steroid regimens can tip this balance by elevating ALK5 activity, down-modulating VEGFC expression or signaling competency, and altering the kinetics of vacuole formation and pore persistence. Time scales are distinct and informative: ALK5-driven transcriptional remodeling and ECM deposition often evolve over hours to days, whereas VEGFC-dependent junctional and vacuolar responses to shear can change over minutes to hours; these differing dynamics generate history-dependent trajectories in which early steroid exposure may prime the interface for later, larger drops in facility unless countered.

In the Ocular MPS system 102, these pathways are observed under controlled ΔP and shear while molecular and structural readouts are synchronized to the load. TM ALK5 activity is captured by phospho-SMAD2/3 and related markers, ECM and cytoskeletal indices, and Raman spectral bands sensitive to protein and matrix composition. SC VEGFC signaling is quantified by VEGFC transcripts and protein, junctional-protein distribution, VEGFR3/PROX1 status, and shear-responsive metrics such as vacuole frequency, pore size distributions, and lumenal patency determined by OCT/OCTA or microscopy.

Electrical and fluidic measurements provide TEER, apparent permeability, facility, and resistance proxies aligned in time with the molecular snapshots. These heterogeneous signals are fused by physics-informed analytics that encode monotone relationships between junctional integrity, permeability, and resistance, enabling estimation of the latent state of the ALK-VEGFC balance and forecasting of outflow trajectories under candidate perturbations.

The resulting picture is one of a coupled, load-sensitive control system in which ALK5/TGFβ signaling provides a tightening drive on the TM side of the interface while VEGFC/VEGFR3 signaling confers a loosening or patterning influence on the SC side, both modulated by hydrodynamic inputs and by the cell-matrix context. Therapeutic leverage follows directly: attenuation of ALK5 tone, restoration, or supplementation of VEGFC signaling, or coordinated schedules that separate steroid anti-inflammatory benefit from junction-tightening penalty can shift the balance toward reduced resistance and improved facility. Because the pathways are interactive and history-dependent, model-based planning with uncertainty quantification is advantageous; by treating ALK5 activity, VEGFC signaling, junctional integrity, and permeability as state variables constrained by known fluid-structure relations, the Ocular MPS system 102 generates calibrated predictions and identifies the minimal additional measurements needed to resolve ambiguity. In this way, the ALK and VEGFC pathways are not merely biomarkers but actionable levers within a quantitatively controlled, device-agnostic framework for measuring, forecasting, and modulating aqueous outflow.

1. Terms and Definitions

Microphysiological system (MPS). Any in-vitro or ex-vivo platform that recapitulates one or more functional aspects of ocular tissue under controlled conditions, including microfluidic organ-/tissue-on-chip devices, organoid-on-chip hybrids, explant perfusion chambers, and hydrogel/scaffold bioreactors, as well as equivalents performing substantially the same functions. References to an "MPS" are device-agnostic and encompass present and foreseeable configurations.

Ocular MPS/AO-MPS. An ocular MPS is an MPS configured for ocular tissues. Aqueous-Outflow MPS (AO-MPS) models any portion of the conventional or distal aqueous outflow pathway (e.g., trabecular meshwork, Schlemm's canal, collector channels, distal conduits).

Measurement/Feature. "Measurement" includes any signal or datum from an MPS (e.g., pressure-flow, permeability/TEER, shear/strain responses, imaging-based morphology, spectroscopy, omics, and device metadata). A "feature" is any representation derived therefrom (scalar, vector, image, spectrum, sequence, graph).

Platform heterogeneity/Cross-MPS normalization. "Platform heterogeneity" refers to differences in geometry, materials, membrane pores, ECM composition, actuation, readouts, or scale. "Cross-MPS normalization" means algorithmic mapping (including learned embeddings) that renders heterogeneous MPS measurements comparable for training or inference.

AI model/Digital twin. "AI model" includes any computational model trained or executed on MPS data and deployable locally, remotely, or in federated form. A "digital twin" is an executable proxy calibrated to an MPS to simulate inputs/outputs for training, prediction, or control.

MPS. MPS device-agnostic in-vitro/ex-vivo platform recapitulating tissue function.

Ocular MPS/AO-MPS. MPS for ocular tissues, including TM-SC outflow.

Measurement/Feature: any signal and derived representation (pressure-flow, TEER, Raman, OCT, metadata).

Cross-MPS normalization: mapping that aligns heterogeneous measurements.

AI model/Digital twin: computational models used to predict or control MPS behavior.

2. Theory of Operation and General Application

In general terms, and without limiting the claims or being bound by any particular theory, the aqueous outflow facility may be viewed as the result of serial and parallel hydraulic resistances contributed by the trabecular meshwork (TM), the TM-membrane interface, and the endothelialized lumen of Schlemm's canal (SC). In microphysiological systems that reproduce this stack 506, 508, 512, 516, the pressure-flow relationship can be expressed with geometry-dependent resistance terms whose effective values are modulated by cellular state and extracellular-matrix composition.

Hydrodynamic loading, combinations of transchannel pressure differentials (ΔP) and wall shear, evokes adaptive cellular and matrix responses that alter barrier function over time. These responses include junctional remodeling (tight-junction continuity and leak paths), cytoskeletal tone and contractility, and pore/vacuole dynamics that influence transcellular and paracellular routes. By acquiring complementary signals in situ, electrical (TEER as a surrogate for barrier integrity), hydraulic (simultaneous ΔP-Q measurement for facility), optical (OCT/brightfield for microstructure, lumen patency, and vacuole formation), and spectroscopic (Raman signatures associated with protein/lipid states and matrix crosslinking), the disclosed system characterizes both function and biochemical/microstructural state from the same specimen under controlled loading.

A learning and inference layer then maps these multimodal features to facility and permeability estimates, and, in various embodiments, to latent state variables that capture the evolving tissue and interface behavior. The models can be physics-informed (constraining predictions to obey pressure-flow relations and continuity), uncertainty-aware (quantifying confidence to gate decisions), and adaptive (updating priors as calibration and longitudinal data accumulate). This enables prediction and hypothesis testing, such as forecasting the facility response to a dose schedule or a shear profile, and supports closed-loop control in which actuation (e.g., pressure, flow, shear, or pharmacologic input) is adjusted in real time to achieve target facility or barrier-integrity setpoints while respecting safety limits.

Because the feature space and control objectives are defined in device-agnostic terms, TEER, $\Delta$P-Q, OCT-derived descriptors, and Raman features rather than any particular scaffold, cartridge, or coating, the approach generalizes across materials and geometries and remains applicable as hardware evolves. Accordingly, the same framework supports pharmacologic, genetic, or mechanical interventions, and can be deployed from benchtop MPS assays to ex vivo preparations and, where appropriate, to clinical analytics that rely on co-registered imaging and sensor streams.

FIG. 1 Sensors/Readouts 106 (TEER/impedance, pressure-flow $\Delta$P-Q, OCT/OCTA, Raman) feed synchronized encoders 108 and a physics-informed state-space model 110 that estimates facility/permeability and junctional integrity with uncertainty; an optimizer/controller proposes experiments and actuation schedules (e.g., dosing, micro-valve control) subject to acceptance metrics and safety limits.

Referring to FIG. 1, the platform integrates an ocular microphysiological system (ocular MPS 104), synchronized sensors/readouts 106, and an analytics/decision layer that produces calibrated facility/permeability estimates and optional control outputs 112. The Ocular MPS system 102 couples an ocular microphysiological device 104 to a measurement- and -control stack arranged in four tiers:

Acquisition layer 104. The device is instrumented with (i) electrical sensing (TEER/impedance) across the TM-membrane-SC stack 506, 508, 512, 516, (ii) hydraulic sensing (pressure and flow to define $\Delta$P-Q and facility), and (iii) optical/spectroscopic sensing (OCT/OCTA for structure/flow and Raman for biochemical state). A timing hub time-stamps all channels and aligns them to a shared clock (see FIG. 9). Calibration and readiness checks (see FIG. 4) precede each run.

Feature/encoding layer. 106 Raw streams are converted into stable, device-agnostic features: TEER ($\Omega \cdot cm^2$) and drift, $\Delta$P-Q slope/linearity, OCT/OCTA-derived junction continuity and lumen patency, and Raman band ratios indicative of junctional or ECM states. These encoders normalize for geometry, temperature, and sampling cadence so results are comparable across chips and days.

Modeling layer 110. A physics-informed state-space/graph model (see FIG. 8) fuses the features to infer latent variables such as permeability, outflow facility, and junction integrity, while producing calibrated uncertainty (e.g., prediction intervals or conformal sets). The model supports counterfactuals (e.g., expected change in facility under an ALK5 inhibitor) and can suggest informative next measurements ("active experiment design") when uncertainty remains high.

Control/decision layer 108. An optimizer/controller uses the model outputs to (a) design experiments (dose levels, timing, $\Delta$P ramps, shear steps) and (b) drive actuators, for example, dosing pumps, micro-valves, perfusion schedules, hydrodynamic actuators, or (in clinical modes) implant-associated reservoirs/controls. Proposed actions are filtered through acceptance metrics and safety gates (see FIG. 14) covering repeatability, coverage, power/current limits, and $\Delta$P bounds. All artifacts, calibrations, parameters, model versions, and control decisions, are logged for traceability.

Outputs 112 layer. The outputs 112 layer assembles the analysis from the AI engine 110 and the synchronization 108 layer to provide a report.

Figure 6:
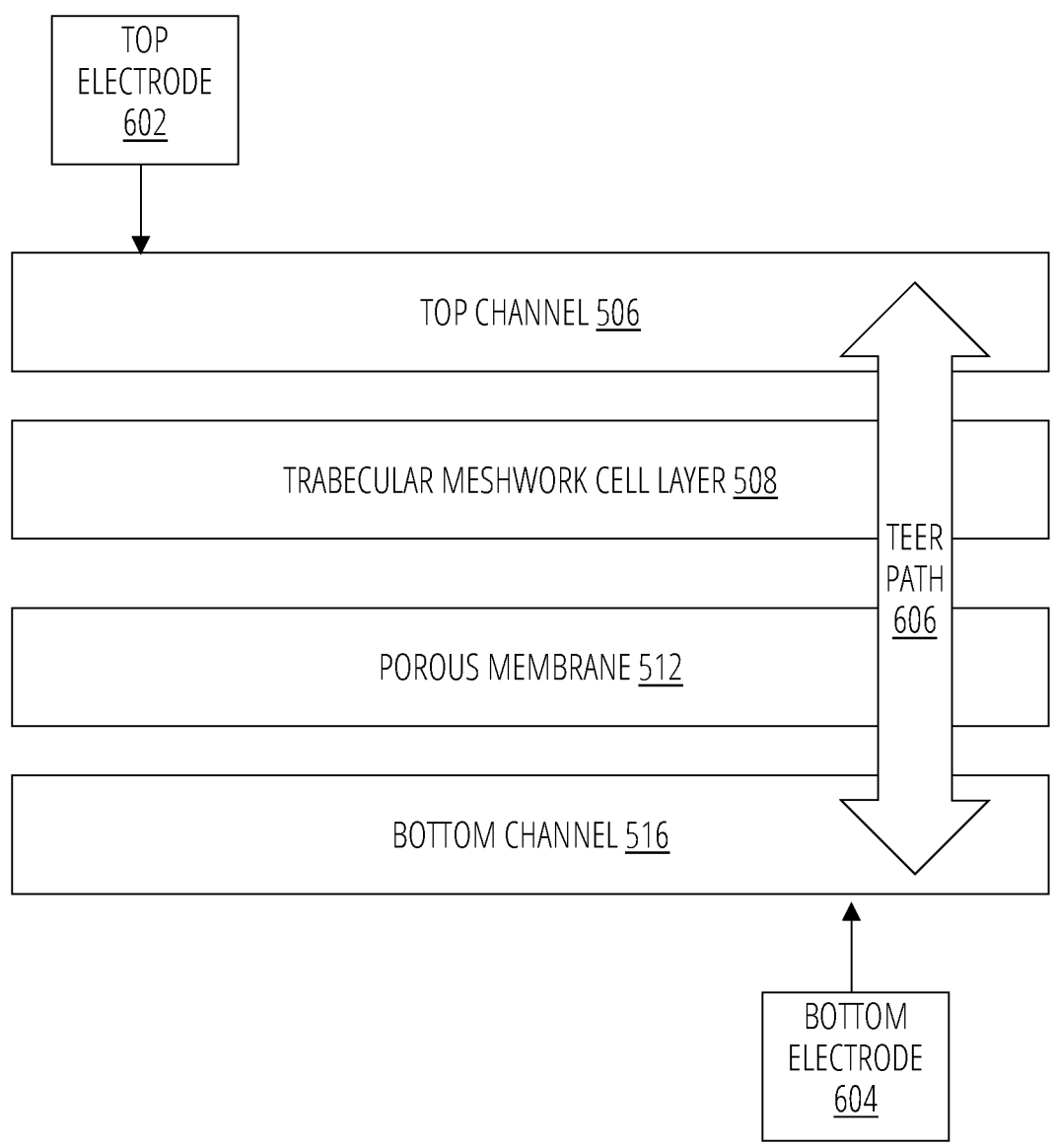
FIG. 6 shows TEER electrode placement and measurement path.
Figure 7:
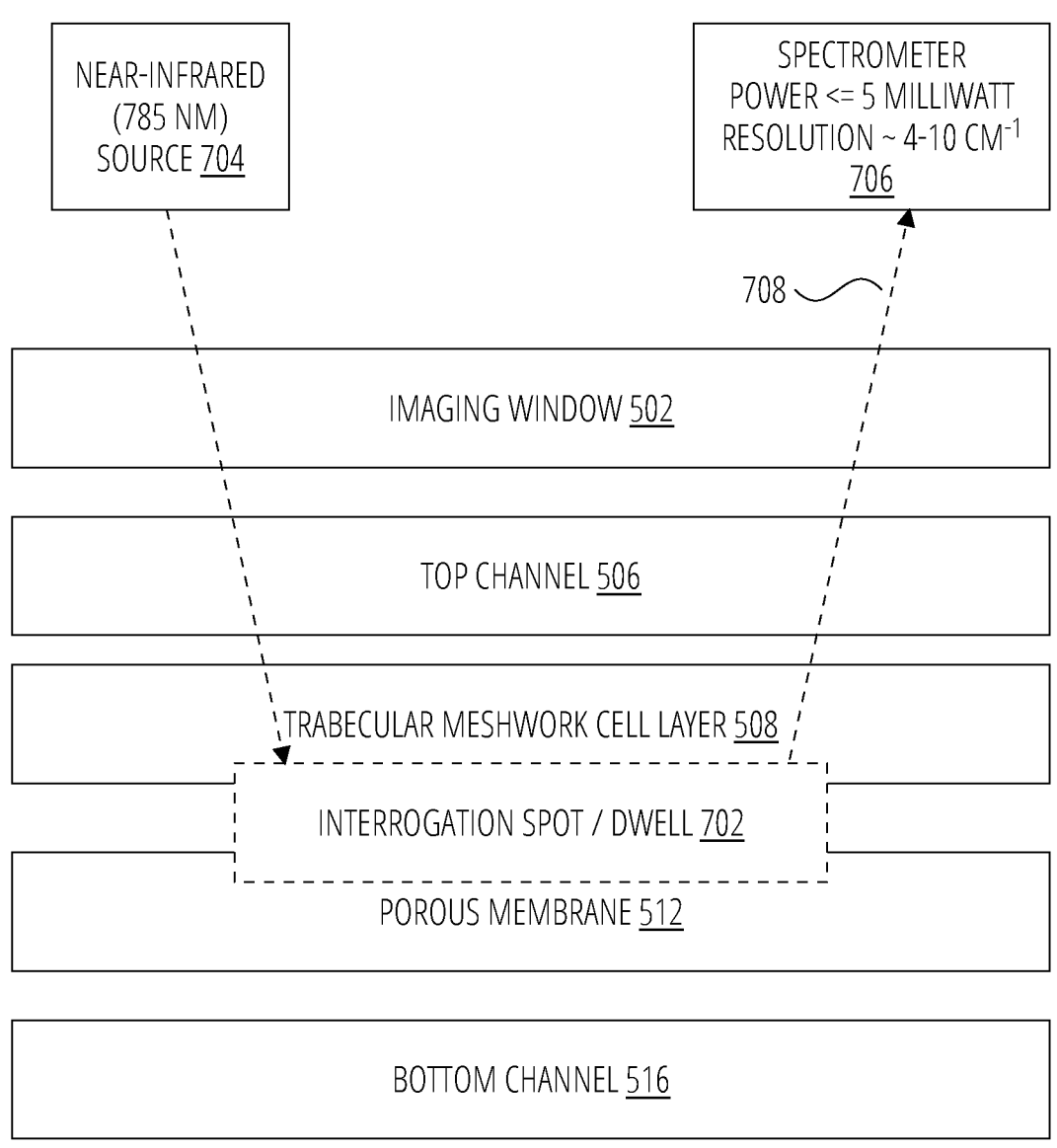
FIG. 7 shows Raman excitation and collection geometry (illustrative).
Figure 8:
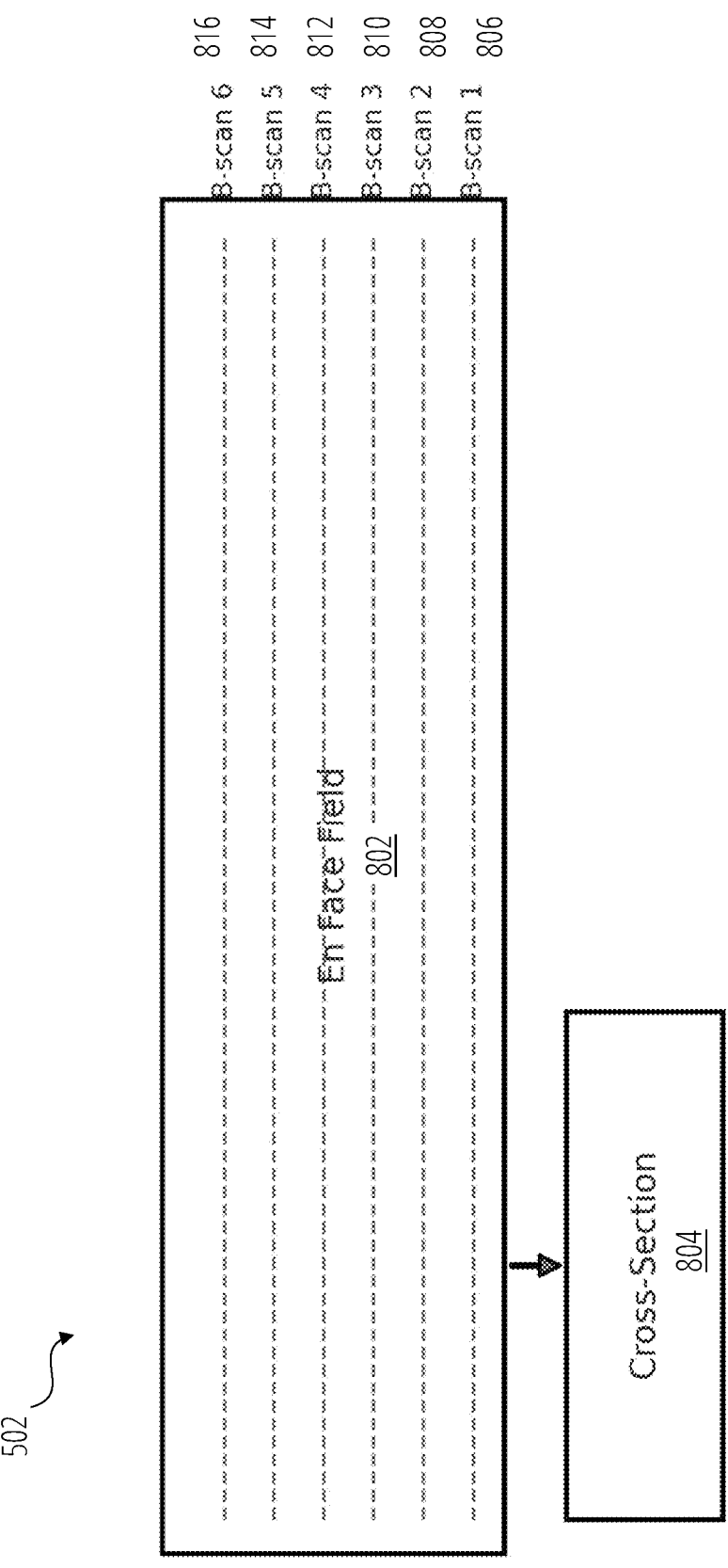
FIG. 8 illustrates the OCT/OCTA scan geometry (illustrative).

This architecture is device-agnostic: it generalizes across scaffold materials and geometries (see FIG. 5), and across sensing configurations (see FIG. 6-FIG. 8). In the Examples, the same loop establishes baseline facility (Example 1), quantifies steroid/ALK-biased remodeling (Example 2), and executes screening-to-optimization workflows (Example 3). The figure is illustrative and non-limiting; modules may be implemented in hardware, firmware, or software, integrated, or distributed, provided that synchronized acquisition, feature encoding, model inference with uncertainty, and safety-gated control are maintained.

Figure 2:
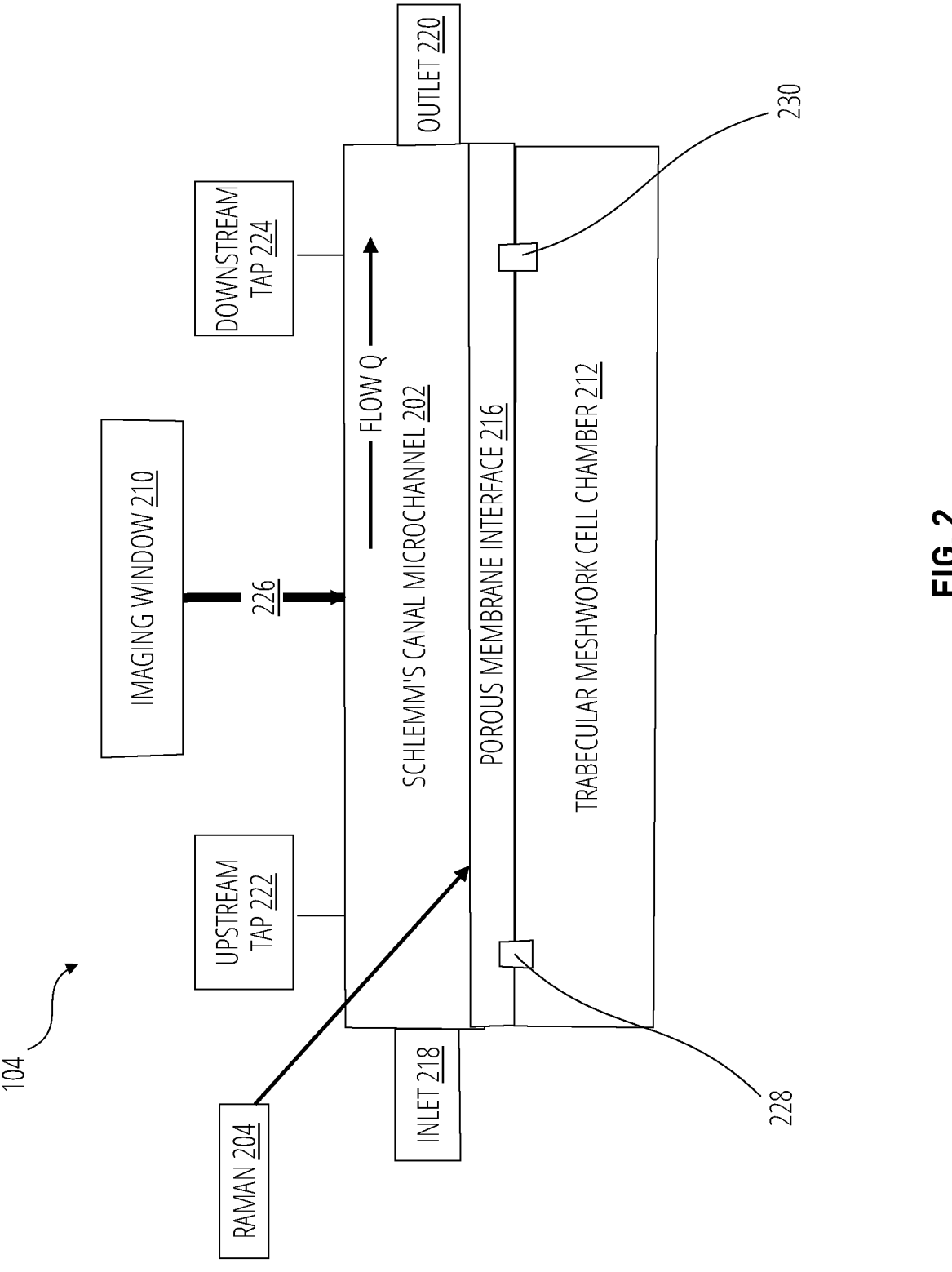
FIG. 2 illustrates a schematic of an eye-on-a-chip (TM-SC) device (not to scale) showing a Schlemm's canal (SC) microchannel over a trabecular meshwork (TM) chamber separated by a porous membrane/interface; inlet and outlet ports; upstream and downstream pressure taps (P_up, P_down) that define ΔP; flow direction (Q); TEER electrode locations across the stack; an OCT/OCTA imaging window and beam path; and an optional Raman excitation path (≈785 nm).

FIG. 2 shows an ocular microphysiological system 104 ("Eye-on-a-Chip") schematic. The trabecular meshwork cell chamber 212, porous membrane interface 216, and Schlemm's canal microchannel 2021 with inlet 218/outlet 220 ports, upstream tap 222/downstream tap 224 ($\Delta$P measurement), optional TEER electrodes 228, 230, and optical access for Raman 204 and OCT/OCTA 226 are shown; perfusion direction indicated (geometry not to scale).

Figure 3:
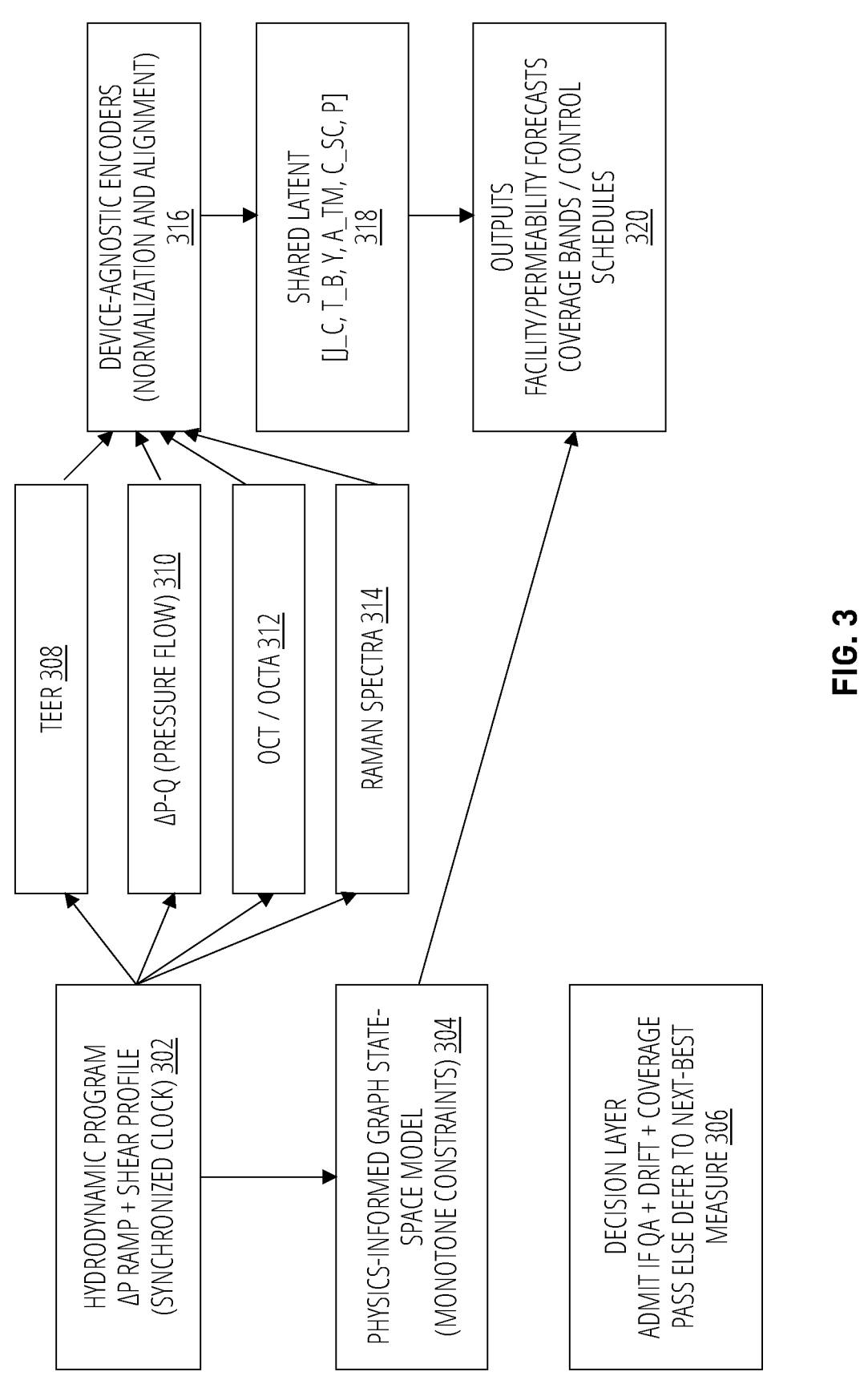
FIG. 3 is a block diagram of the synchronized sensing, physics-constrained inference, and uncertainty-gated actuation pipeline that links the hydrodynamic program, multimodal measurements (TEER, ΔP-Q, OCT/OCTA, Raman), device-agnostic encoders, a graph state-space model, and a decision layer that issues forecasts and control schedules.

FIG. 3 shows the synchronized sensing to physics-constrained inference to uncertainty-gated actuation. A programmable hydrodynamic profile (pressure-drop ramp and shear waveform on a synchronized clock) drives concurrent acquisitions of TEER 308, $\Delta$P-Q (pressure flow) 310, OCT/OCTA 312, and Raman spectra 314. Device-agnostic encoders 316 normalize these signals and map them into a shared latent 318 state [Jc,Tb,Y,aTM,vSC,p]. A physics-informed graph state-space model 304 propagates the coupled TM-SC dynamics under monotone constraints to generate facility/permeability forecasts and candidate control schedules 320. A decision layer 306 admits outputs only when calibration, baseline-drift, coverage, and safety gates are satisfied; otherwise, actions are deferred.

Referring to FIG. 3, the system operates on a single synchronized clock that drives a programmable hydrodynamic program 302 comprising pressure-drop ramps and shear waveforms. While this program runs, the platform acquires co-registered measurements from multiple modalities, trans-epithelial/endothelial electrical resistance (TEER 308), $\Delta$P-Q (pressure flow) 310, OCT/OCTA 312 imaging, and Raman spectra 314. Time-locking the actuation and the sensors prevents phase error between loading and readout and ensures that every sample can be compared on a common timeline.

Signals from each modality are first normalized and mapped by device-agnostic encoders 316 into a shared latent 318 representation. This representation captures geometry-independent descriptors of the tissue state, including junction continuity (J_c), junction "belt" thickness (T_b), tortuosity (Y), proxies of trabecular-meshwork ALK5 activity (a_TM) and Schlemm's-canal VEGFC signaling (v_SC), and an outflow-resistance proxy (p) derived from ΔP-Q. Cross-device normalization places data from different scaffolds and chip layouts into the same latent space so that experiments can be pooled and transferred.

Inference proceeds in a physics-informed graph state-space model 304 in which the trabecular meshwork and Schlemm's canal are represented as coupled nodes. Message-passing captures paracrine and mechanical interactions across the interface, and recurrent dynamics propagate the state forward in time. Monotone and directionality constraints encode domain knowledge, for example, increased junction thickness is penalized unless it corresponds to increased resistance, improved junction continuity must not increase resistance, and antagonism between ALK5 and VEGFC pathways is preserved. The model 304, therefore, produces forecasts of facility and permeability that are consistent with known physiology and returns calibrated bands that quantify prediction uncertainty.

All model outputs are evaluated by a decision layer 306 instrumented with explicit gates. The sensing stack must pass calibration checks; baseline drift limits must be satisfied; conformal prediction must guarantee coverage within policy; and safety limits for laser power, electrode current density, and allowed ΔP/shear must be respected. If the gates pass, the system admits the result and issues actionable outputs-facility/permeability forecasts with confidence intervals and control schedules such as dose timing/duty cycle or implant-sector actuation. If any gate fails or the predictive bands are too wide, the system defers action and recommends the next measurement most likely to shrink uncertainty under the current conditions.

Figure 4:
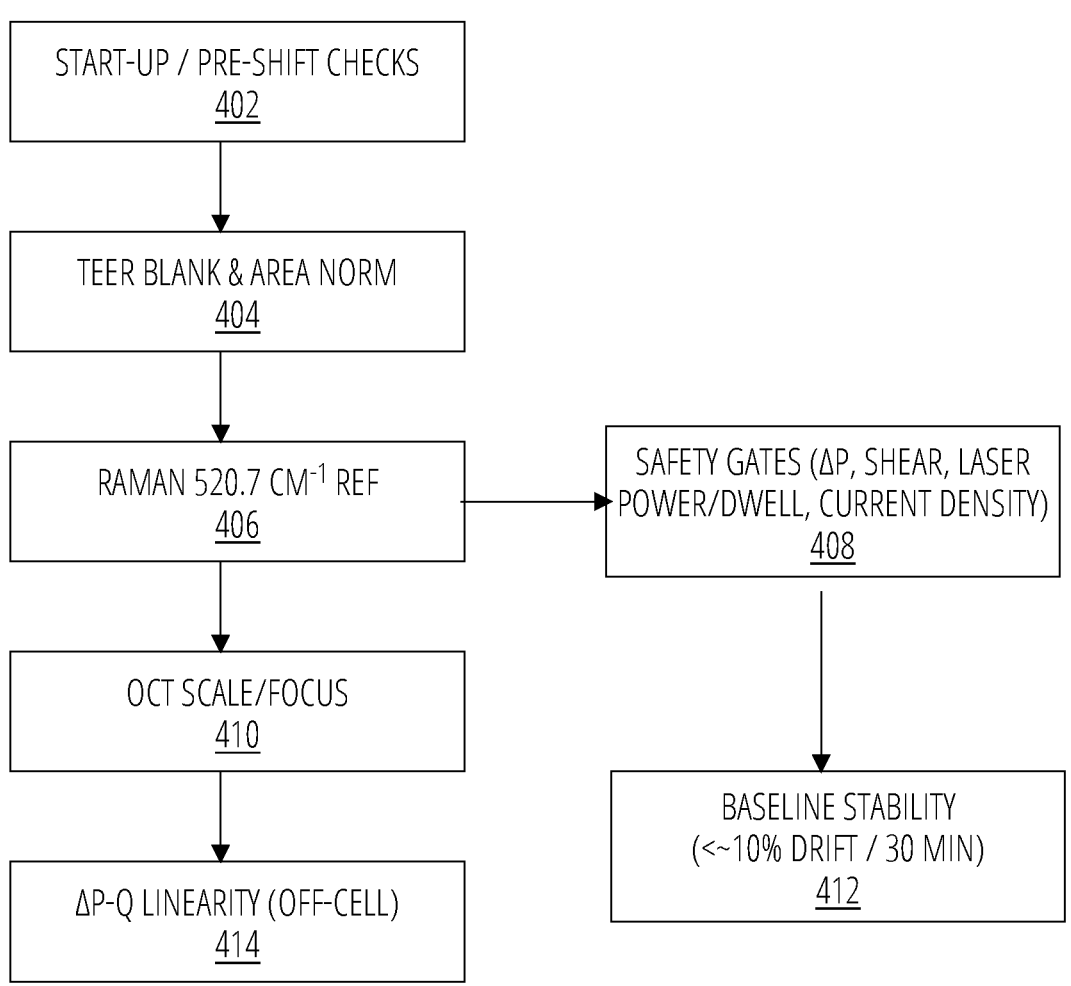
FIG. 4 depicts the Calibration and Quality-Assurance workflow used prior to experimental runs.
Figure 9:
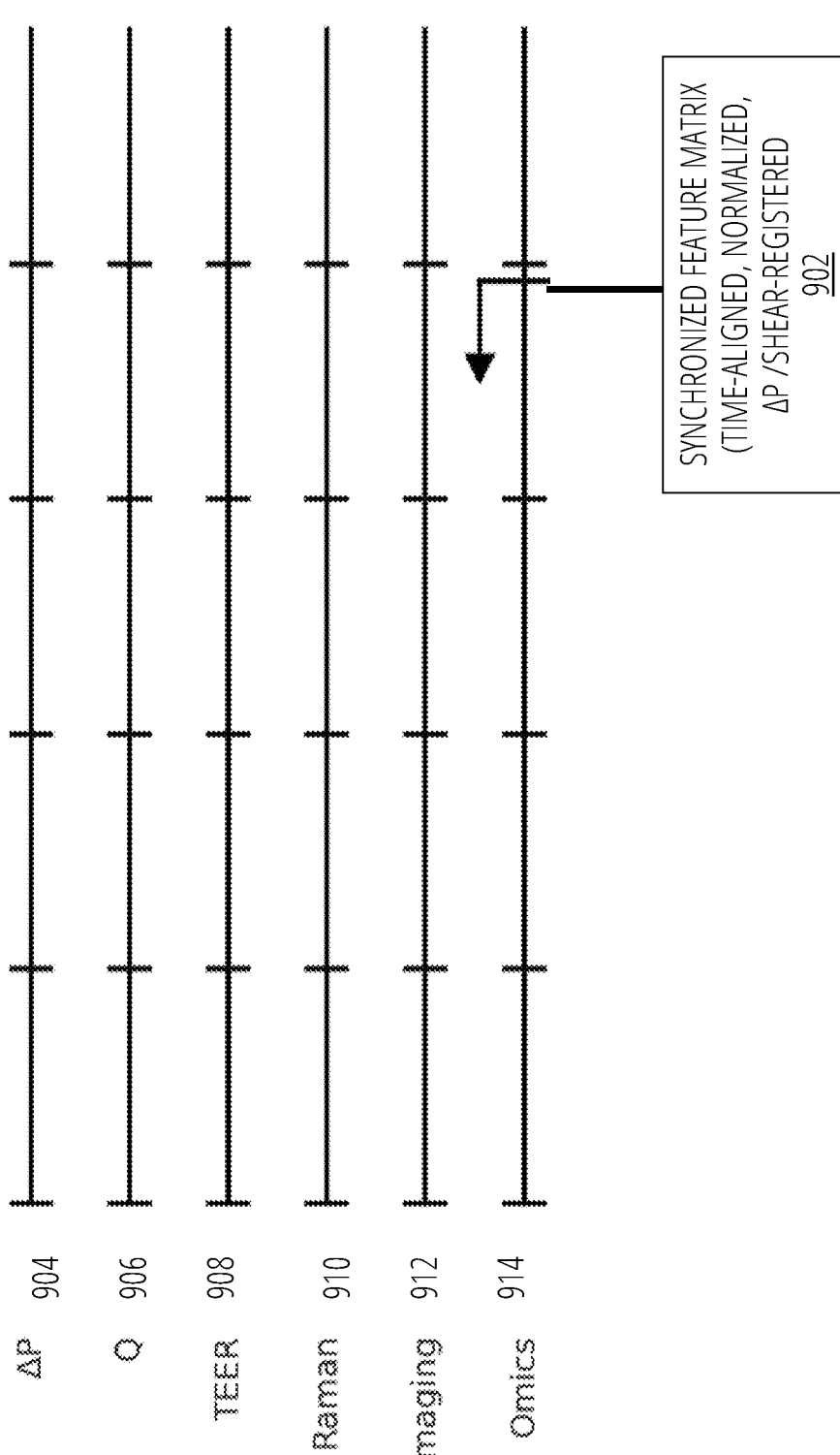
FIG. 9 shows a timeline synchronization and feature assembly (illustrative).
Figure 12:
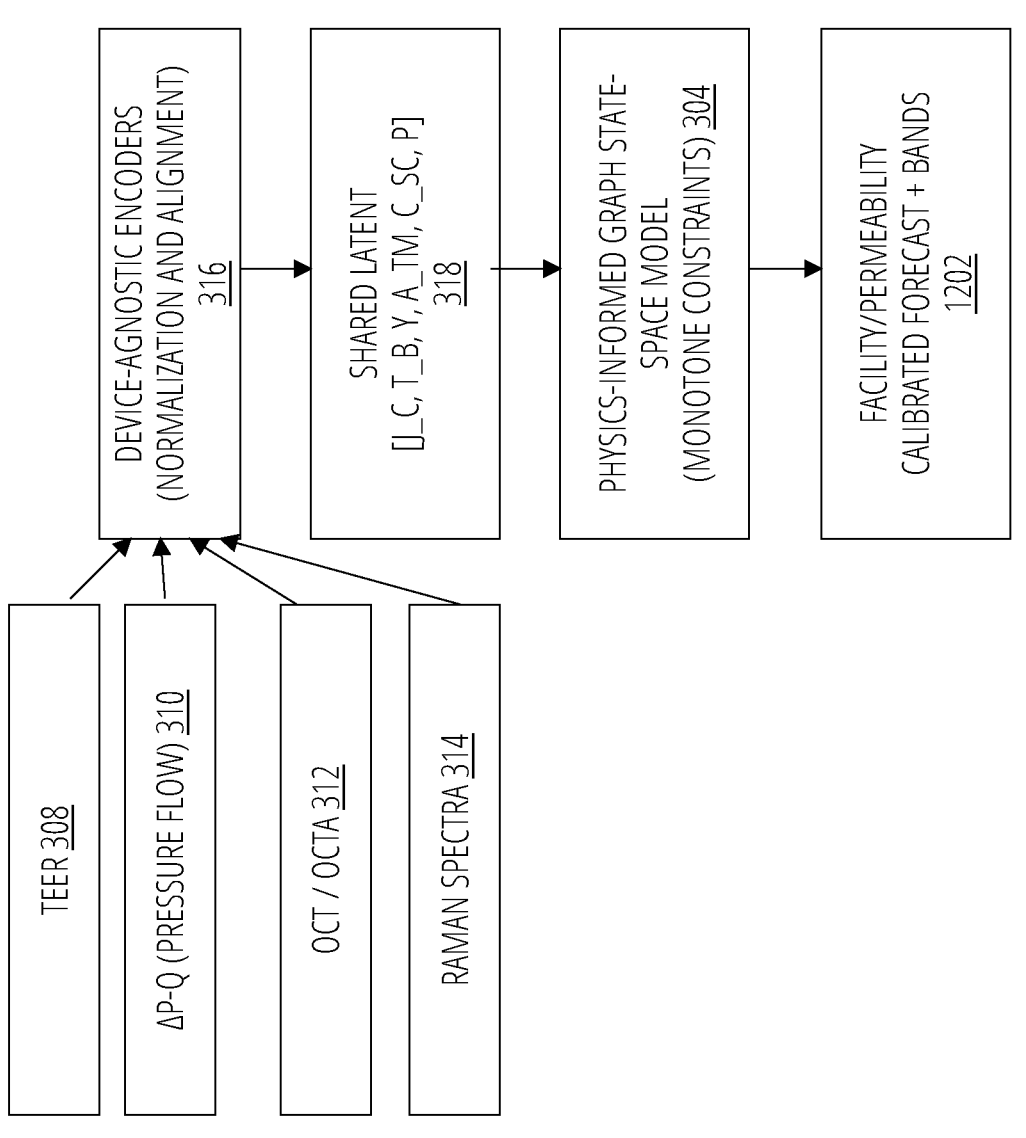
FIG. 12 shows a device-agnostic feature space and cross-MPS normalization flowchart.
Figure 13:
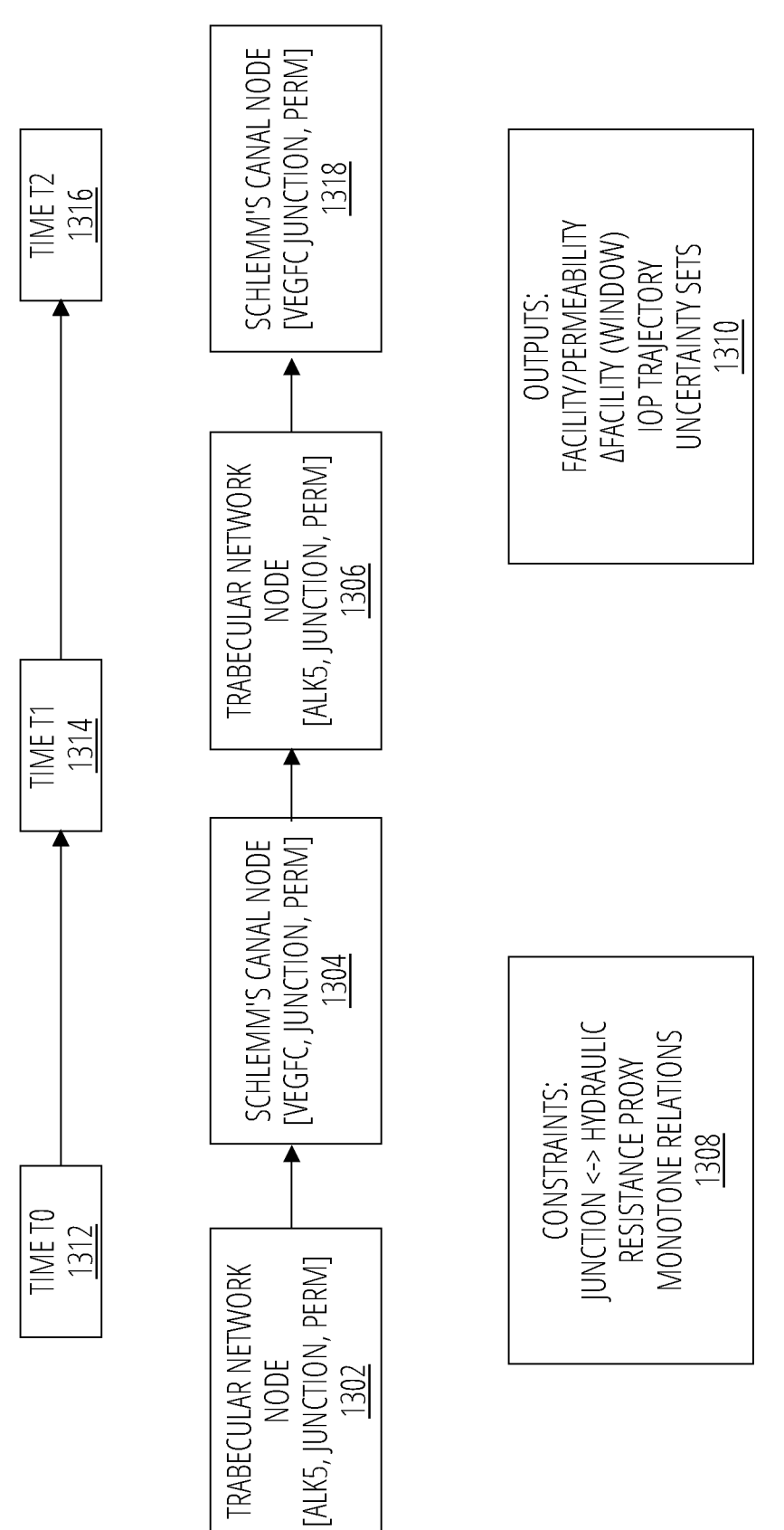
FIG. 13 shows a physics-informed graph state-space model (illustrative).
Figure 14:
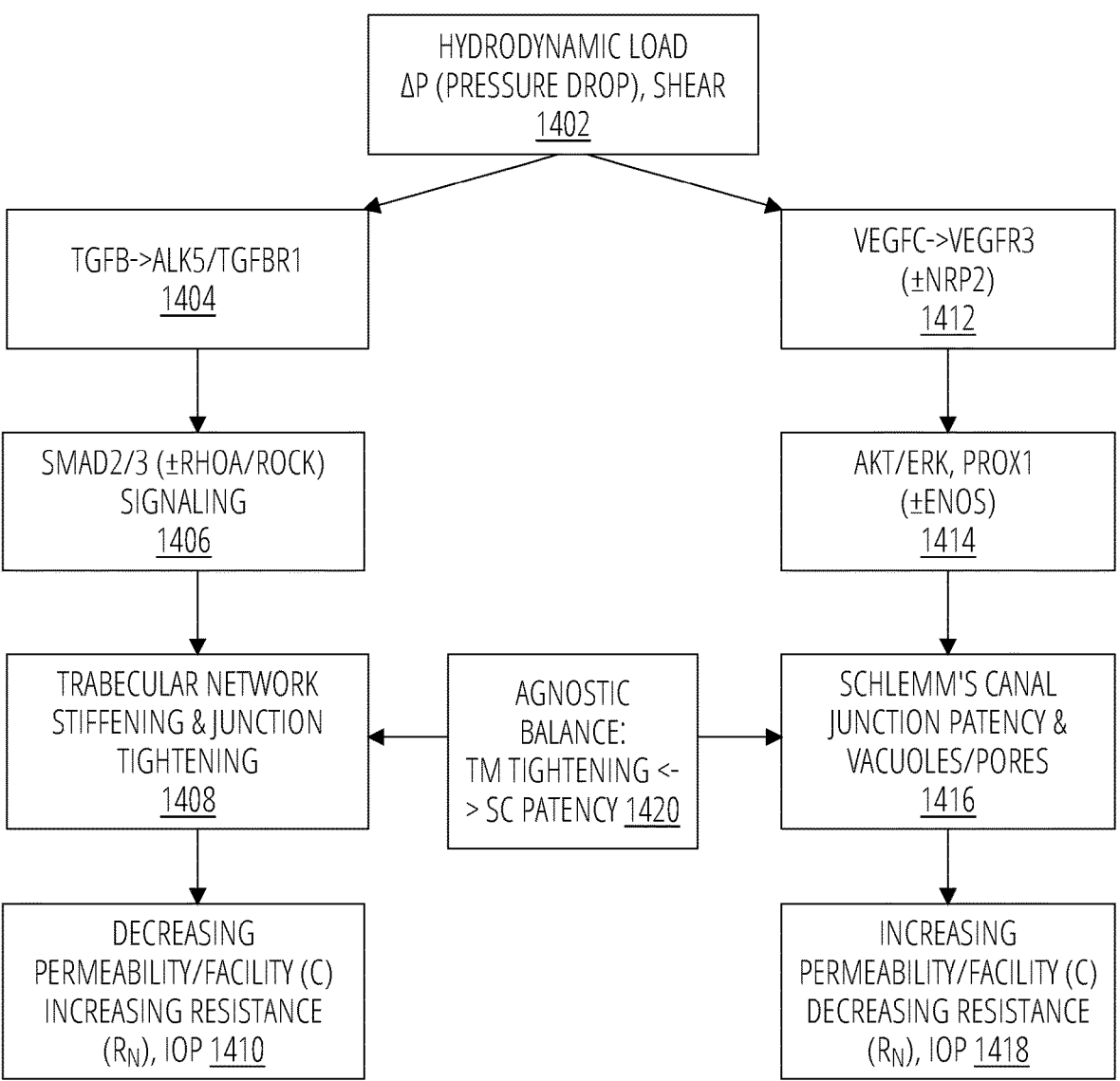
FIG. 14 shows the pathway coupling under load.

The data path shown in FIG. 3 ties the specification together: the hydrodynamic program and QA procedures of FIG. 4, the chip geometry of FIG. 5 and the sensing layouts of FIG. 6-FIG. 8, the global timing of FIG. 9, the graph/state-space formulation of FIG. 12, the pathway balance under load in FIG. 13, and the acceptance metrics of FIG. 14. Each admitted decision is logged with model and encoder versions, calibration records, and gate outcomes, providing traceability suitable for regulated deployment.

Unified Architecture Across Embodiments

Throughout the embodiments, the platform operates under one architecture. A defined hydrodynamic program 302 (pressure-drop and shear waveforms) drives the TM-membrane-SC stack 506, 508, 512, 516 while TEER 308/impedance, ΔP-Q (pressure flow) 310, OCT/OCTA 312, and microscopy, Raman spectra 314 and other molecular readouts are acquired on a common clock and co-registered to the device geometry. Modality-specific encoders normalize these measurements into a shared, device-agnostic latent that captures junction continuity, belt thickness, tortuosity, pathway activity, and an outflow-resistance proxy. A physics-informed graph state-space model 304 then propagates this latent under known biological couplings and enforces monotone relationships between junction features and resistance, yielding calibrated predictions of facility and permeability with associated coverage bands. A decision layer 306 applies admission gates (calibration, drift, and conformal-coverage thresholds) so that actions, such as regimen selection, actuator set-points, or implant-sector schedules, proceed only when confidence and safety criteria are met; otherwise, the system defers and proposes the next most informative measurement. Variants that emphasize particular modalities, analytes, scaffolds, routes of administration, or clinical actuators are alternative implementations of this same loop and do not depart from the descriptions herein, which reside in the synchronized, physics-constrained, uncertainty-aware pipeline rather than in any one sensor, material, or actuator.

FIG. 4 depicts the Calibration and Quality-Assurance workflow used prior to experimental runs, including electrical (TEER) checks 404, hydraulic ΔP-Q linearity/leak checks 414, optical calibrations for Raman 406 and OCT/OCTA 410, and safety/acceptance gates 408.

Referring to FIG. 2, the platform enters each experiment through a calibration and QA gate that harmonizes electrical, hydraulic, and optical subsystems and records acceptance results for traceability.

Electrical (TEER) preparation 404. A blank/reference device (or open-state lane) is measured to obtain Rblank. Electrodes are checked for continuity and a stable phase at the chosen excitation. The test device is then measured to obtain Rsample and area-normalized TEER is computed as $$TEER = (R\text{sample} - R\text{blank}) \cdot A$$

This run proceeds only if TEER drift over a short dwell is within tolerance (illustratively, $<\sim10\%/30$ min) and electrode current density is below a safety limit 412.

Hydraulic readiness. With cells bypassed or off-chip, the pressure-flow path is verified for ΔP-Q linearity 414 (illustratively, $$r2 \geq 0.98 r^2 \backslash ge\ 0.98 r2 \geq 0.98)$$

and for absence of leaks at the intended step range.
Medium temperature and viscosity are logged (e.g., 37° C.; viscosity recorded) so facility estimates are comparable across days and devices. Target shear setpoints in each channel are validated from geometry and flow.

Optical calibration. The Raman channel is wavelength-calibrated 406 (e.g., silicon at 520.7 $cm^{-1}$), spectral resolution verified (illustratively $\sim4$-10 $cm^{-1}$), and power at the sample limited (e.g., $\leq5$ mW). The OCT/OCTA channel is scale-checked against a feature of known thickness, focus is verified, and the scan geometry is registered to the device axes (or implant arc, if present) 410.

Synchronization and logging. Acquisition clocks are aligned to the global timeline (see FIG. 9), and the system records geometry (channel widths/heights, membrane thickness/porosity), environmental conditions, software/firmware versions, and calibration artifacts. This produces a run docket against which subsequent measurements are compared.

Acceptance and fail-forward. A run is released only if QA gates pass: e.g., off-cell ΔP-Q linearity within tolerance, TEER stability within bounds, Raman/OCT calibrations confirmed, and all safety gates (laser power, current density, maximum ΔP and thermal budget) enforced 408. If any check fails, FIG. 4 prescribes a remedial branch (re-calibrate, replace electrode, re-prime hydraulic loop) before re-testing. Establishing this stateful baseline enables reliable fusion of TEER, ΔP-Q, Raman, and OCT/OCTA in later figures and Examples.

Notes: Thresholds and specific values above are illustrative and non-limiting; the workflow remains valid across device materials and geometries so long as the same acceptance logic is applied.

FIG. 5 shows an ocular MPS 104 cross-section with hydrodynamic loading and optical access (illustrative). The device reproduces the outflow interface: a top channel 506 delivering shear 504 over the trabecular meshwork cell layer 508, an ECM scaffold 510 on a porous membrane 512, a Schlemm's canal endothelium 514, and a Schlemm's canal Lumen (bottom channel) 516. The OCT/OCTA beam 520 enters through the imaging window 528. Upstream tap 522 and downstream tap 524 define the ΔP (pressure drop) 526 across the stack 506, 508, 512, 516 for facility/permeability measurements.

Referring to FIG. 5, the ocular MPS 104 reconstructs the hydrodynamic and structural context of the trabecular outflow pathway. A top channel 506 carries perfusate over a confluent trabecular meshwork cell layer 508, establishing a programmable shear stress (τ) as indicated by the streamwise arrow. Beneath the trabecular meshwork cell layer 508 lies an ECM scaffold 510 supported by a porous membrane 512; the basal side is lined by a Schlemm's canal endothelium 514 that opens into the Schlemm's canal Lumen (bottom channel) 516. Together, these layers provide the test path for both trans-layer transport and electrical resistance measurements used elsewhere in the disclosure.

An imaging window 528 spans the stack 506, 508, 512, 516 to allow non-contact optical access. The OCT/OCTA beam 520 is shown entering orthogonally to the layers, enabling co-registered assessment of microstructure (e.g., junction continuity, vacuoles/pores) and, when used with angiographic modes, motion contrast within the Schlemm's canal Lumen (bottom channel) 516. The upstream tap 522 and the downstream tap 524 bracket the device hydraulically; their pressure readings define the pressure drop ΔP applied across the TM-membrane-SC interface. By stepping ΔP while holding channel flow, the system measures facility and apparent permeability under load and correlates those endpoints with simultaneous optical and electrical readouts.

This cross-section serves as the geometric reference for later figures: FIG. 6 places the TEER electrodes normal to this stack; FIG. 7 illustrates Raman excitation/collection through the same window; FIG. 6 details OCT/OCTA scan geometry and registration; and FIG. 8 provides the synchronized timing used for ΔP ramps and shear steps. Dimensions, materials, and port placements are exemplary and non-limiting; the Ocular MPS system 102 generalizes to alternative scaffolds and membranes so long as the essential stack, Top Channel to TM to membrane/ECM to SC endothelium to SC lumen, and access for ΔP, shear, and optical interrogation are preserved.

TABLE 1

Symbols, Definitions, Units

| Symbol | Quantity | Definition/Formula (typical form) | Units (SI/ common lab) | Notes/Typical ranges |
|---|---|---|---|---|
| τ | Wall shear stress | $\tau = \mu \cdot \dot{\gamma} \approx 6\,\mu\,Q/(w\,h^2)$ (rectangular microchannel, $h \ll w$) | Pa/dyn · cm$^{-2}$ (1 dyn · cm$^{-2}$ = 0.1 Pa) | Illustrative for FIG. 3: 0.5-5 dyn · cm$^{-2}$ (≈0.05-0.5 Pa); adjustable 0.1-20 dyn · cm$^{-2}$ |
| $\dot{\gamma}$ | Shear rate | $\dot{\gamma} = 6\,Q/(w\,h^2)$ (laminar, parallel-plate approximation) | s$^{-1}$ | Used with $\tau = \mu \cdot \dot{\gamma}$; depends on channel geometry |
| ΔP | Pressure drop | $\Delta P = P\_up - P\_down$ (across TM-membrane-SC stack) | Pa/mmHg (1 mmHg = 133.322 Pa) | Illustrative for FIG. 3: 2-6 mmHg (≈267-800 Pa); adjustable 0-20 mmHg |
| Q | Volumetric flow rate | Controlled perfusion input; relates to τ and ΔP via geometry/resistance | m$^3$ · s$^{-1}$/μL · min$^{-1}$ | Device-specific (e.g., 0.1-20 μL · min$^{-1}$ typical in microfluidic assays) |
| μ | Dynamic viscosity | Fluid property (e.g., aqueous-like media, ~water at 37° C.) | Pa · s (mPa · s = 10$^{-3}$ Pa · s) | Typical: 0.7-1.0 mPa · s at 37° C. |
| R_h | Hydraulic resistance | $R\_h = \Delta P/Q$ | Pa · s · m$^{-3}$/ mmHg · (μL · min$^{-1}$)$^{-1}$ | Inverse of hydraulic conductance; geometry-dependent |
| C (or F) | Facility (conductance) | $C = Q/\Delta PP$ (in vivo variant: $C = Q/(\Delta P - EVP)$) | m$^3$ · (Pa · s)$^{-1}$/ μL · min$^{-1}$ · mmHg$^{-1}$ | In-chip, EVP term typically not used |
| L_p | Hydraulic conductivity (membrane) | $L\_p = Q/(A \cdot \Delta P)$ | m · (Pa · s)$^{-1}$ | Per-area analogue of facility; used for membranes/monolayers |
| P_app | Apparent permeability | $P\_app = (1/A) \cdot (dC\_B/dt) \cdot (V\_B/C\_A0) = J\_s/(C\_A - C\_B)$ | cm · s$^{-1}$ (SI: m · s$^{-1}$) | Report with donor/receiver volumes, sample interval, and analyte |
| TEER | Trans-epithelial/ -endothelial electrical resistance | $TEER = (R\_sample - R\_blank) \cdot A$ | Ω · cm$^2$ (SI: Ω · m$^2$) | Measure barrier integrity; specify electrode placement/frequency |
| J_s | Solute flux | $J\_s = (1/A) \cdot dN\_B/dt = P\_app \cdot (C\_A - C\_B)$ | mol · m$^{-2}$ · s$^{-1}$ | Pairs with permeability assays |
| A | Area (membrane/ monolayer) | Projected exchange area used in P_app, L_p, TEER | m$^2$/cm$^2$ | Specify effective area after gaskets/inserts |
| w, h, L | Channel width, height, length | Geometry parameters used in τ, $\dot{\gamma}$, and resistance models | m (or μm) | State tolerances; $h \ll w$ assumption noted where used |

TABLE 1-continued

| | | Symbols, Definitions, Units | | |
| --- | --- | --- | --- | --- |
| Symbol | Quantity | Definition/Formula (typical form) | Units (SI/ common lab) | Notes/Typical ranges |
| φ (ε_p), r_p, δ_m | Porosity, pore radius, membrane thickness | Structural properties for transport models | — /m/m | Often provided by manufacturer or measured (SEM) |

Table 1 lists symbols referenced in FIG. 5 with concise definitions, canonical formulas, and units. Values and ranges are illustrative and device-specific unless otherwise noted. Parallel-plate approximations apply under laminar flow with h<<wh unit conversions given for SI and common lab units.

TABLE 2

| | | Scaffold Substrates: Purpose & Selection Criteria | | | |
| --- | --- | --- | --- | --- | --- |
| Substrate (material/ form) | Primary purpose in MPS | What qualifies it for selection (key criteria) | Typical ECM coatings/ primers | Typical specs (illustrative) | Notes/risks |
| Track-etched Polycarbonate (PC) membrane | TM-SC divider enabling bidirectional transport, permeability, and TEER; supports TM/SC monolayers | Consistent cylindrical pores; wide pore-size availability; easy TEER integration; widely available inserts | Collagen IV, laminin, fibronectin; optional plasma activation; polydopamine or silane primer if needed | Pore ≈ 0.2-3 μm; thickness ≈ 6-20 μm; clear/translucent | Moderate optical clarity; ensure solvent compatibility; handle carefully to avoid tearing |
| Track-etched PET membrane | TM-SC interface with good mechanical robustness; transport and barrier assays | Broad vendor support; good mechanical strength; common in Transwell formats | Collagen IV/laminin/ fibronectin; plasma activation; optional polydopamine | Pore ≈ 0.2-3 μm; thickness ≈ 6-20 μm | Autofluorescence/ clarity depends on vendor; verify imaging modality needs |
| Microfabricated SU-8 (epoxy) porous scaffold | SC inner-wall mimic with defined micro-architecture; supports shear studies and vacuole/pore imaging | Precise pore geometry and spacing; rigid under shear; microfabrication repeatability | ECM coat (collagen IV/ fibronectin/ laminin); optional Hystem-C/Ext racel hydrogel overlay | Pores often ~ 1-12 μm; thickness tens of μm | Requires cleanroom/ microfab; ensure cytocompatible processing and leach-out of photoresist residues |
| GelMA (gelatin methacrylate) hydrogel (photo-crosslinked) | 3D TM-like ECM; supports infiltration and tunable stiffness for mechanobiology/ drug response | RGD-rich adhesion; photo-patternable; modulus tunable by degree of methacrylation and light dose | Pre-mix ECM proteins (collagen I/IV) post-gelation or surface coat | E ~ 0.5-20 kPa typical; thickness 100-1000+ μm | Photoinitiator/cell exposure must be controlled; swelling affects channel geometry |
| Methacrylated Collagen I (ColMA) hydrogel | Native-like fibrillar matrix for TM; improved biomimicry vs. purely synthetic gels | Biochemical fidelity; supports TM phenotype; tunable via concentration and crosslinking | Self-contained (collagen) ± laminin/fibron ectin boost; neutralization/ gelation control | E ~ 0.5-10 kPa; fibrillar network | Batch variability; slower gelation vs. GelMA; temperature/pH sensitive |
| Thiolated Hyaluronate + Thiolated Gelatin + PEG-DA (Hystem-C/ Extracel-like) | GAG-rich, compliant matrix; 2D-on-3D SC/TM interfaces; barrier tuning | Independent control of gelation and stiffness; tunable via hyaluronate content for outflow relevance | Intrinsic adhesion via gelatin; augment with collagen IV/fibronectin if needed | E ~ 0.2-5 kPa; thickness 100-1000+ μm | Component mixing accuracy critical; monitor long-term stability under flow |
| Elastin-Like Polypeptide (ELP) blends (with collagen/HA) | Elastic ECM to emulate cyclic strain and recoil; supports TM mechanotrans-duction | High resilience; tunable via sequence/ composition; good for stretch/cycle studies | Collagen IV/laminin co-formulations or surface coats | E ~ 0.5-10+ kPa; viscoelastic behavior | Synthesis cost/availability; thermal responsiveness may affect handling |

TABLE 2-continued

Scaffold Substrates: Purpose & Selection Criteria

| Substrate (material/ form) | Primary purpose in MPS | What qualifies it for selection (key criteria) | Typical ECM coatings/ primers | Typical specs (illustrative) | Notes/risks |
|---|---|---|---|---|---|
| Fibrin hydrogel | Rapidly gelled, degradable matrix for remodeling/ migration assays | Enzymatically remodelable; supports angiogenic/ migration behaviors | Blend with collagen/ laminin; aprotinin control for stability | E ~ 0.1-2 kPa; fast gelation | Mechanical fragility; proteolysis can change geometry during long perfusions |
| Polyacrylamide (PA) gel with ECM coat (2D) | Defined-stiffness 2D substrate for TM/SC mechanotransduction without 3D confounds | Precisely tunable modulus; decouples stiffness from ligand density via ECM coating | Covalently linked collagen IV/laminin/ fibronectin (e.g., Sulfo-SANPAH chemistry) | E ~ 0.1-50 kPa; thin films on glass | Non-degradable/ inert; not suitable for 3D infiltration; requires careful surface chemistry |
| Silicon nitride/ glass nano-porous membrane | Ultra-thin, high-clarity divider for high-resolution imaging and rapid transport | Optical transparency; very low thickness; engineered pore patterns | Collagen IV/laminin coats; silane primers on glassy surfaces | Thickness ~ 0.1-1 µm; pores sub-µm to few µm | Cost/availability; brittle handling; integration complexity |
| Polydopamine (PDA) primer layer (on polymer/glass) | Universal adhesion layer to retain ECM proteins and improve coating durability | Catechol chemistry binds many substrates; boosts ECM adsorption and stability | proteins Apply PDA, then ECM (collagen IV/laminin/ fibronectin) | Film ~ 10-50 nm (self-assembled) | Can darken/absorb light; control deposition time to avoid excess roughness |
| Silane primers (e.g., APTES) on glass/oxide surfaces | Covalent linking of ECM or crosslinkers to improve long-term adhesion under flow | Forms functional groups (—NH2, —COOH) for coupling; mproves repeatability | Silane → crosslinker (e.g., glutaraldehyde) → ECM | Monolayer scale; process-dependent | Moisture-sensitive; over-silanization can cause haze or delamination |
| Basement-membrane ECM coats (Collagen IV, Laminin, Fibronectin) | Promote TM/SC adhesion, junction formation, and barrier function on membranes/ scaffolds | Biochemical relevance to outflow tissues; improves permeability/ TEER stability | Single or mixed coatings; may add heparan sulfate proteoglycans | Surface coverage per vendor protocol | Lot variability; optimize concentration/time; combine with primers if wash-off occurs |

Table 2 summarizing commonly used scaffold substrates for ocular microphysiological systems (MPS) that model aqueous outflow. Entries list primary purpose, what qualifies each substrate for selection, typical ECM/primers, and practical notes. Values/ranges are illustrative and device-specific.

FIG. 6 shows TEER electrode placement and measurement path. A top electrode 602 contacts the top channel 506 and a bottom electrode 604 contacts the Schlemm's canal Lumen (bottom channel) 516; the TEER path 606 indicates the impedance path across the trabecular meshwork cell layer 508 and the porous membrane 512. Reported TEER is area-normalized and blank-subtracted: TEER=(R_sample– R_blank)×A (illustrative layout; device-agnostic).

Referring to FIG. 6, the electrical readout uses a two-electrode configuration arranged perpendicular to the tissue stack 506, 508, 512, 516. A top electrode 602 contacts the top fluid channel 506 upstream of the trabecular meshwork cell layer 508, and a bottom electrode 604 contacts the Schlemm's canal Lumen (bottom channel) 516 downstream of the porous membrane 512. The double-headed arrow indicates the trans-epithelial/endothelial resistance path (TEER path 606), an effective field line that runs normal to the layers through the top channel 506, the trabecular meshwork cell layer 508, the porous membrane 512, and the Schlemm's canal Lumen (bottom channel) 516. The measured resistance along this path reflects barrier integrity:

tighter cell-cell junctions and denser matrix produce higher TEER, whereas junctional opening reduces TEER.

During operation, a small alternating signal is applied between the electrodes 602, 604. The system records voltage and current to estimate the sample's resistance and compares it to a blank or reference measurement acquired without cells (or under a known open state). TEER is reported as the blank-corrected resistance scaled by the effective interface area of the trabecular-meshwork-membrane region. Geometry and temperature are logged so that values remain comparable across devices and days. In FIG. 6, the electrode tips are placed outside the flow chambers and connected with short leaders; this avoids disturbing hydrodynamics and keeps the figure clear and compliant.

FIG. 6 also anchors calibration and quality checks used elsewhere in the specification: verification of a stable blank, acceptable drift over a defined interval, and agreement with the linear relation observed in off-cell pressure-flow tests when those are performed. During experimental runs, TEER is acquired on the same synchronized clock as pressure-flow and optical or spectroscopic sensing (for example, OCT/ OCTA and Raman), allowing electrical barrier changes to be mapped to microstructural and biochemical features. In steroid-challenge examples, TEER typically rises as trabecular-meshwork junctions tighten; under ALK5 attenuation or VEGF-C support, TEER trends back toward baseline in parallel with improved outflow facility. Safety gates-covering current density, maximum drive amplitude, and thermal load-together with acceptance metrics such as repeatability and coverage limits, are enforced using this geometry so that the electrical endpoint integrates cleanly with the broader multimodal analytics.

FIG. 7 shows Raman excitation and collection geometry (illustrative). A near-infrared (785 nm) source 704 interrogates the stack 506, 508, 512, 516 through the imaging window 502; spectra are collected from an interrogation spot 702 (lateral footprint) over a specified dwell (integration time). Acquisition abides by power and resolution limits (e.g., ≤5 mW at the sample; ≈4-10 cm$^{-1}$ spectral resolution). The geometry supports co-registration with hydraulic and electrical readouts.

Referring to FIG. 7, Raman measurements are performed with a near-infrared (785 nm) source 704 beam introduced orthogonally through the imaging window 502 so that illumination and collection paths are co-axial. The interrogation spot 702 denotes the lateral footprint on the TM-membrane-SC stack 506, 508, 512, 516; the dwell is the integration time per spectrum. Backscatter 708 photons are coupled to a spectrometer 706, providing a biochemical fingerprint of junctional and extracellular-matrix states without perturbing the hydraulic geometry.

Power at the sample is limited by a safety gate (illustratively≤5 mW) and verified during Calibration/QA (see FIG. 4). Spectral calibration may use a stable reference (e.g., a silicon line), and the optical train maintains a resolution on the order of ≈4-10 cm$^{-1}$ so that band-integrated ratios and other derived features are consistent across devices and days. Locations are co-registered to the device coordinate frame (and, when present, to an implant or fiducial) so repeated acquisitions address the same anatomical sector under changing ΔP and shear loads.

During an experimental run, spectra are acquired at scheduled times synchronized to the global timeline (see FIG. 9), typically bracketing ΔP steps or shear plateaus. The learning system converts spectra into device-agnostic features (e.g., band ratios linked to junctional order or ECM composition) and fuses them with TEER and ΔP-Q to estimate permeability and facility with calibrated uncertainty. If uncertainty remains high or drift is detected, the controller can request an additional spectrum or an alternate spot/dwell within preset limits. The geometry is non-limiting: fiber-coupled or microscope-based implementations, confocal pinholes, and alternative windows or substrates may be used, provided the essential elements, normal illumination through the window, defined spot/dwell on the TM-membrane-SC stack 506, 508, 512, 516, and backscatter 708 collection under safety/acceptance gates, are preserved.

FIG. 8 shows the OCT/OCTA scan geometry (illustrative). An en face field 802 over the imaging window 502 is swept by multiple parallel B-scans (e.g., B-scan 1 . . . N) 806,808,810, B-scan 4 812,814,816. Each B-scan yields a cross-section 804; the set forms a 3-D volume and en-face projections used to quantify junction continuity, membrane and SC interfaces, lumen patency, and OCTA motion contrast.

Referring to FIG. 8, the en face field 802 defines a rectangular region of interest on the imaging window 502 of the ocular MPS. The instrument acquires a set of parallel B-scans at a defined pitch (illustratively tens of micrometers) across this field (B-scan 1 . . . N) 806,808,810, B-scan 4 812,814,816. Each B-scan provides a cross-section 804 through the TM-membrane-SC stack 506, 508, 512, 516 (see FIG. 5), while the ensemble yields a 3-D volume and en-face projections suitable for structural and angiographic analysis.

During OCT mode, interfaces are segmented to locate the trabecular meshwork cell layer 508, porous membrane 512 plane, Schlemm's canal endothelium 514, and Schlemm's canal Lumen (bottom channel) 516. Derived metrics include junction continuity/tortuosity indices, membrane thickness, lumen height/area, and vacuole/pore counts along the inner wall. In OCTA mode, repeated B-scans at the same position provide motion-contrast maps that report flow/particle movement within the SC lumen or perfusate channels. The scan coordinates are registered to the device axes and, when applicable, to fiducials on the scaffold (e.g., membrane pores) so that spatial sectors can be compared over time or matched to hydraulic taps.

Acquisition parameters, field size, B-scan count and pitch, line rate, frame averaging, and OCTA repeats, are recorded in the run docket (see FIG. 9 for synchronization). Calibration/QA (see FIG. 4) verifies scale, focus, and co-registration; acceptance checks flag excessive speckle, motion, or defocus. The resulting en-face and cross-sectional features are exported in device-agnostic units and fused with ΔP-Q and TEER signals to estimate permeability, facility, and junction integrity with uncertainty bounds (see FIG. 1 and FIG. 10). Parameters above are illustrative and non-limiting; alternative scan orders (raster, bidirectional), pitches, or projection slabs may be used provided that the en-face field, B-scan stack, and cross-section mapping are preserved.

FIG. 9 shows a timeline synchronization and feature assembly (illustrative). Independent data streams (ΔP 904, Q 906, TEER 908, Raman 910, imaging 912, Omics 914) are stamped to a common clock, aligned to step/hold events, and resampled onto a canonical timeline to yield a synchronized feature matrix 902 used for modeling and control.

Referring to FIG. 9, each acquisition channel is collected on its own native cadence (continuous for ΔP 904 and Q 906; periodic for TEER 908; scheduled for Raman 910 and imaging 912; snapshot batches for Omics 914). Prior to analysis, the system performs a synchronization pass:

1. Clock alignment and event marking. All streams are referenced to a shared run clock; control events (e.g., ΔP step times, shear plateaus, dosing pulses) are marked on every channel.
2. Canonical timeline. A canonical time grid is defined (e.g., 1-5 s resolution for continuous channels with additional breakpoints at every control event and measurement timestamp). This grid becomes the backbone for feature assembly.
3. Resampling & registration.
    ΔP 904 and Q 906 are filtered and resampled to the grid; slopes during ramps and means during plateaus are computed.
    TEER 908 traces are drift-corrected and area-normalized; values are interpolated to the grid with hold-last-value between samples.
    Raman 910 spectra acquired at scheduled times are reduced to band ratios or other indices and inserted at those timestamps; between stamps, no interpolation is performed (samples are treated as sparse points).
    imaging 912 outputs (e.g., junction continuity, lumen patency) are converted to scalars per frame and placed at their frame times.
    Omics 914 panels (snapshots) are attached at their collection times and otherwise left empty. Each derived value is registered to hydrodynamic state by attaching the contemporaneous ΔP and shear setpoints.

1. Normalization and quality gates. Features are normalized (e.g., to baseline or vehicle controls) and screened against acceptance checks (calibration passes, drift bounds, data completeness). Missing points are coded explicitly rather than imputed unless a protocol specifies a conservative interpolation.

2. Synchronized feature matrix 902. The outcome is the time-aligned feature matrix (lower right callout in FIG. 7), containing for each grid time: ΔP, Q, TEER, Raman indices, imaging metrics, any available omics features, and associated flags (e.g., plateau ID, dose cohort, replicate). This matrix is the input to the learning and control layers (see FIG. 10 and FIG. 1).

This synchronization scheme supports counterfactual modeling (e.g., comparing matched windows before/after a ΔP step), enables uncertainty-aware fusion of heterogeneous sensors, and ensures that active-experiment proposals schedule new measurements at the most informative times (e.g., mid-plateau Raman 910, end-plateau TEER 908). The approach is device-agnostic and remains valid across alternative sampling cadences and actuator schedules, provided all streams are stamped to a common clock and registered to hydrodynamic load.

Figure 10:
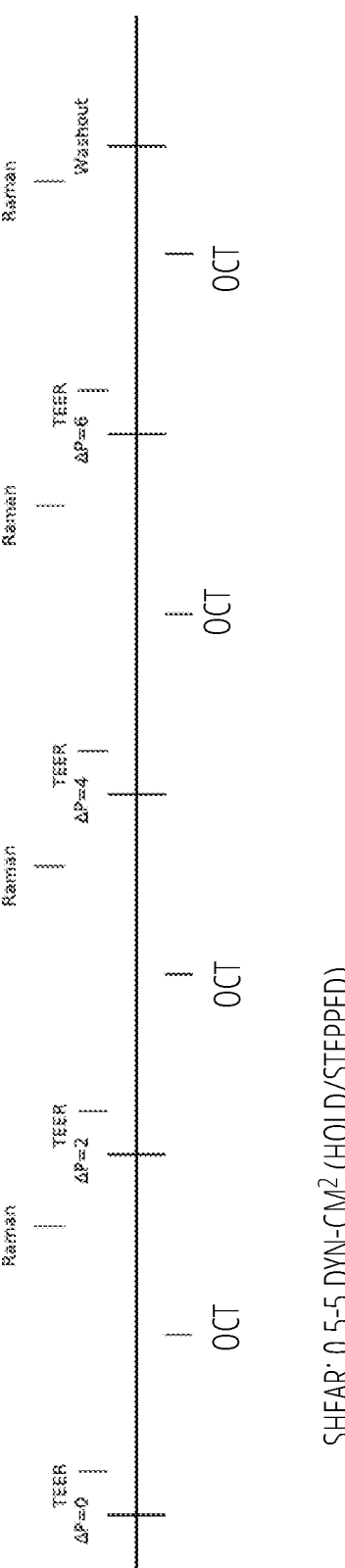
FIG. 10 illustrates a ΔP/Shear Program with Sampling and QA Admission Gates (illustrative).
Figure 11:
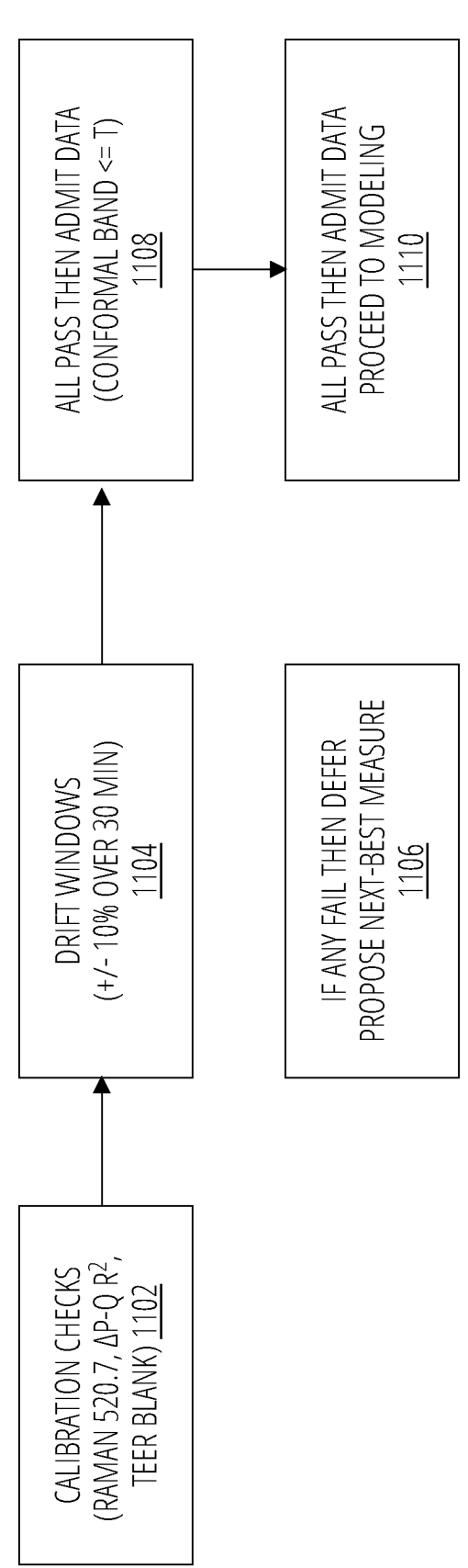
FIG. 11 illustrates how the data is admitted to modeling in a flowchart.

FIG. 10 is a ΔP/Shear Program with Sampling and QA Admission Gates (illustrative). A stepped pressure-drop sequence (ΔP=0→2→4→6 mmHg) under controlled shear ($\approx$0.5-5 dyn·cm$^{-2}$) schedules TEER, Raman, and OCT acquisitions. FIG. 11 shows how the data is admitted to modeling only if calibration checks pass, baseline drift remains within ±10% over 30 minutes, and conformal coverage bands are below the preset threshold t; otherwise, collection is deferred and the next-best measurement is proposed.

FIG. 10 illustrates how sensing is coordinated with the hydrodynamic program and how quality assurance gates control which measurements enter the analysis. The timeline represents a run executed on a synchronized clock in which the pressure drop across the TM-membrane—SC stack 506, 508, 512, 516 is stepped from 0 to 2, 4, and 6 mmHg while shear stress is held or stepped within a physiological window of approximately 0.5 to 5 dynes per square centimeter. At each plateau, specific modalities are triggered: TEER readings bracket the plateaus to capture state before and after the pressure step, Raman spectra are acquired at defined dwell points to sample biochemical state, and OCT frames are interleaved to record structural correlates such as junction continuity and lumen patency. A washout segment closes the sequence to characterize reversibility.

FIG. 11 shows how the data is admitted to modeling only if calibration checks pass, baseline drift remains within +10% over 30 minutes, and conformal coverage bands are below the preset threshold t; otherwise, collection is deferred and the next-best measurement is proposed.

FIG. 11 shows the admission logic that governs whether the acquired data are eligible for modeling. The run begins with calibration checks 1102 that verify the Raman wavenumber reference, the linearity of the ΔP-Q relation off-cell, and the TEER blank. Once these checks pass, the stream is monitored for baseline drift windows 1104, requiring that TEER and Raman indices remain within plus or minus ten percent over a thirty-minute window. If drift exceeds this bound 1106, the system does not advance to modeling; instead, the collection is deferred, and the orchestration engine schedules the next-best measurement to recover coverage efficiently. When calibration and drift criteria are satisfied 1108, the final gate evaluates predictive uncertainty using split-conformal residuals; only if the coverage band is no wider than the pre-specified threshold t are the measurements admitted. Passing data 1110 are time-aligned and normalized and then forwarded to the physics-informed model for facility and permeability estimation, whereas failing data are logged with reason codes to preserve traceability and to guide reacquisition. This gating architecture ensures that downstream inferences are built from calibrated, stable, and sufficiently certain inputs while keeping the experiment synchronized to the hydrodynamic program.

FIG. 12 shows a device-agnostic feature space and cross-MPS normalization. FIG. 12 depicts the cross-MPS normalization pipeline in which modality-specific encoders apply wavenumber and intensity calibration for Raman, geometric and shear registration for pressure-flow and TEER, and field-of-view registration for OCT/OCTA to produce a shared, device-agnostic feature set—junction continuity, belt thickness, tortuosity, TM signaling activity, SC VEGFC signaling level, and a hydraulic-resistance proxy—with missing-modality masking and unit scaling for model input.

FIG. 12 illustrates how heterogeneous measurements are converted into a single, comparable feature set before modeling. Starting from synchronized acquisitions, TEER 308, pressure-flow measurements 310, Raman spectra 314, OCT/OCTA 312 imaging, and optional omics, the pipeline first performs modality-appropriate calibration. TEER 308 is blank-corrected and reported per unit area; pressure-flow 310 traces are aligned to the run clock and to the applied shear and pressure program; Raman spectra 314 are wavenumber-checked against a reference and intensity-scaled; OCT/OCTA 312 fields are registered to the chip geometry so that the same regions are tracked over time. These steps remove instrument bias and ensure that all inputs share a common timing and coordinate frame.

After calibration, each modality is translated by device-agnostic encoders 316 into plain, geometry-independent descriptors of tissue state and flow resistance. Imaging yields junction continuity, junction "belt" thickness, and tortuosity; Raman yields biochemical indices linked to pathway activity; TEER and pressure-flow provide an electrical-barrier measure and a hydraulic-resistance proxy; targeted molecular panels contribute trabecular-meshwork signaling activity and Schlemm's-canal VEGFC signaling level. Unit scaling and device-to-device compensation place these descriptors on consistent ranges across scaffolds, channel sizes, and sites, so that a measurement from one chip is directly comparable to a measurement from another.

The feature assembler also handles real-world irregularities. If a modality is missing or momentarily out of tolerance, the corresponding fields are marked as unavailable rather than imputed, and downstream models are informed to rely on the modalities that passed quality gates. Batch effects and site differences are mitigated with learned normalization parameters and reference controls, while per-run metadata—such as temperature, fluid viscosity, and effective area—are retained to interpret outliers and to support auditability.

The result of FIG. 12 is a compact, device-agnostic feature vector that captures junction structure, biochemical state, pathway activity, and a measure of hydraulic resistance on a common scale. This vector is the standard input to the physics-informed graph state-space model 304 described in FIG. 13 and is used throughout the Examples so that baseline calibration (Example 1), steroid challenge and rescue (Example 2), regimen optimization (Example 3), and VEGF-C scheduling with washout (Example 4) can be compared fairly across chips and over time. By enforcing consistent calibration, registration, and scaling, FIG. 12 is the bridge between raw signals and reliable, mechanism-aware inference.

Unless stated otherwise, all measurements used in the Examples are mapped into the device-agnostic feature space of FIG. 12. TEER is area-normalized and blank-corrected;

pressure-flow traces are registered to the synchronized clock and shear program; Raman spectra are intensity-scaled and wavenumber-calibrated; and OCT/OCTA-derived metrics, such as junction continuity, belt thickness, and tortuosity, are computed from registered fields of view. These normalizations yield a shared set of features (junction continuity, belt thickness, tortuosity, TM signaling activity, SC VEGFC signaling level, and a hydraulic-resistance proxy) that is comparable across scaffolds, chip formats, and runs, enabling cross-MPS analysis and the model training used in Examples 1-4.

FIG. 13 shows a physics-informed graph state-space model (illustrative). Time-unrolled nodes $(t_0 \rightarrow t_1 \rightarrow t_2)$ 1312, 1314, 1316 represent coupled TM and SC compartments with latent variables (e.g., ALK5, VEGFC, junction, permeability). Edges encode biophysical dynamics and cross-talk; constraints 1308 enforce monotone links between junction integrity and hydraulic resistance and bound non-physical values. Encoded observations from ΔP-Q, TEER, OCT/OCTA, and Raman update the state; outputs 1310 include facility/permeability trajectories, IOP projections, and uncertainty sets used for decision and control.

Referring to FIG. 13, the platform formalizes tissue behavior as a graphical state-space system:

State and structure. Each time slice contains nodes for the trabecular meshwork (TM) 1302, 1306 and Schlemm's-canal (SC) endothelium 1304,1318. A node's latent state may include: pathway activities (ALK5 for TM bias; VEGFC for SC bias), junction integrity/continuity, and permeability (or the reciprocal hydraulic resistance). Cross-edges capture TM↔SC coupling (e.g., junction tightening in TM tends to raise resistance; VEGFC-driven SC patency lowers it).

Dynamics (physics-informed). The transition map $$x_{t+1} = f(x_t, u_t, \theta) + w_t$$

is constrained by ocular hydrodynamics and basic plausibility: non-negative permeabilities; monotone relation between junction integrity and resistance; bounded rates of change; and conservation/geometry links so that facility is a deterministic function of permeability, channel geometry, and load (ΔP, shear). Inputs utu_tut encode actuation (dose, ΔP ramp, shear step). The observation map $$y_t = h(x_t) + v_t$$

links latent variables to measured features: TEER (area-normalized resistance), ΔP-Q slope/plateau values, OCT/OCTA (junction continuity, lumen patency, vacuoles/pores), and Raman (band-ratio biochemical indices). Features are time-aligned and normalized per FIG. 12.

Inference. Online filtering (e.g., extended/unscented Kalman, particle filter, or message passing on the time-unrolled graph) updates posteriors over xtx_txt as data arrive, producing facility/permeability estimates with confidence bands. Model calibration includes coverage-guaranteeing uncertainty (e.g., conformal sets) so acceptance metrics can be checked consistently across devices and days.

Outputs and use. The model yields:

Facility & permeability trajectories and windowed estimates for Examples and QA;

IOP trajectory projections via a lightweight anterior-segment link;

Uncertainty sets the gate reporting and control;

Counterfactuals (expected change under a proposed dose, ΔP step, or schedule).

Figure 15:
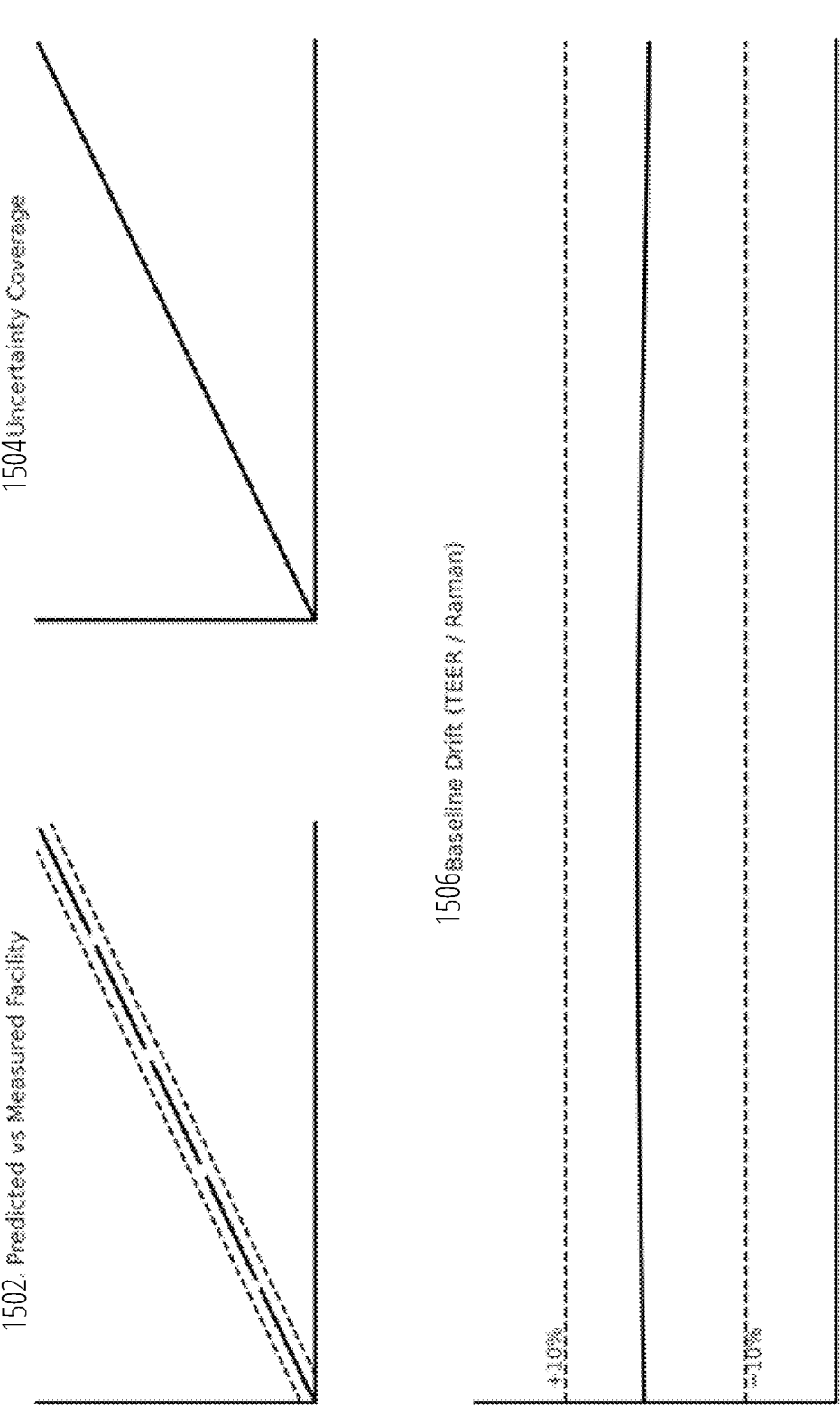
FIG. 15 illustrates acceptance metrics (illustrative).

These outputs drive the optimizer/controller (see FIG. 1) to choose doses, schedules, or next measurements ("active experiment design"), subject to safety and acceptance checks (see FIG. 15).

Generalization. Because inputs are device-agnostic features with explicit geometry/temperature normalization, the same model transfers across scaffolds, membranes, and sensing stacks 506, 508, 512, 516 (cf. FIG. 5-FIG. 8). Priors (e.g., measured membrane porosity or endothelial coverage) may be injected as initial beliefs without limiting claim breadth; novelty resides in the analytics and control layer that fuses multimodal signals under physics-informed constraints.

FIG. 14 shows the pathway coupling under load: ALK5-biased TM tightening versus VEGFC-biased SC patency (illustrative). Left branch: TGFβ→ALK5/TGFβR1 1404 to SMAD2/3 (±RhoA/ROCK) 1406 drives trabecular meshwork stiffening and junction tightening 1408, decreasing permeability/facility (c) 1410 and increasing $R_h$/IOP. Right branch: VEGFC→VEGFR3 (±NRP2) 1412 to AKT/ERK, PROX1 (±eNOS) 1414 promotes Schlemm's canal junction patency 1416 and vacuoles/pores, increasing permeability/facility (c) 1418 and lowering RA/IOP. A central callout notes the agnostic balance 1420 between trabecular meshwork tightening and Schlemm's canal patency.

Referring to FIG. 14, the hydrodynamic load 1402, pressure drop ΔP across the TM-membrane-SC stack and shear within the channels, sets the mechanical context for pathway activity. The diagram summarizes how two mechanistically distinct but interacting arms steer the effective barrier function and, consequently, outflow facility.

TM (left branch, tightening). In response to steroid challenge or load-dependent cues, TGFβ signaling through ALK5/TGFβR1 activates SMAD2/3 with possible reinforcement via RhoA/ROCK. The net effect is cytoskeletal stiffening and junctional tightening within TM cells. Functionally, this reduces permeability and facility (C) and raises hydraulic resistance ($R_h$), which, if uncompensated, elevates IOP. In the platform, this branch is observed as increased TEER, Raman band shifts consistent with tighter junctional/ ECM states, and OCT signatures of diminished trans-cellular vacuoles.

SC endothelium (right branch, patency). VEGFC acting on VEGFR3 (FLT4), influenced by NRP2, engages AKT/ ERK and PROX1 programs (with eNOS-linked tone) that favor junction patency and vacuole/pore formation along the inner wall of Schlemm's canal. This increases permeability/ facility and lowers R$/IOP. On the instrument, the branch appears as OCT/OCTA evidence of lumen patency and vacuoles/pores, Raman features aligned with a more permeable state, and TEER changes in the permissive direction.

Coupling and balance. The agnostic balance 1420 block indicates that the TM-tightening and SC-patency influences combine to set the net working point of the outflow pathway. The balance is context-dependent (load, local biochemistry, sector, or implant geometry) rather than strictly antagonistic. In the learning framework (see FIG. 13), the coupling weights are learned from synchronized features (see FIG. 10 and constrained by physics (junction integrity monotonically maps to $R_h$). This lets the controller (see FIG. 1) propose counter-balancing interventions, for example, ALK5 attenuation to relieve tightening or VEGFC scheduling to promote SC patency, subject to acceptance metrics (see FIG. 15).

Non-limiting scope. The depicted mediators (TGFβ/ ALK5; VEGFC/VEGFR3; SMAD2/3; AKT/ERK; PROX1; eNOS) are exemplary. Additional or alternative modulators may be substituted without departing from the Ocular MPS system 102, provided the analytics capture how junction state and lumen patency determine permeability/facility under load and drive safety-gated control of dosing or perfusion.

TABLE 3

| | | | | Uncertainty | Notes / |
| Investigation | Primary Signals/ | | | & Decision | Operating |
| Focus | Features | AI Engine(s) | Key Outputs | Logic | Windows |
| --- | --- | --- | --- | --- | --- |
| Baseline facility & permeability under load | TEER/impedance (area-normalized); $\Delta$P-Q traces; viscosity-adjusted flow; geometry (w, h, L) | Physics-informed regression; Kalman/state-space smoothing | Facility C; apparent permeability Papp; drift-corrected baseline with CIs | Conformalized residuals; alert if CI width > $\tau$C or $\Delta$P-Q non-linearity ($r^2 < 0.98$) | $\Delta$P $\approx$ 2-6 mmHg (adj. 0-20); shear $\approx$ 0.5-5 dyn · cm$^{-2}$ (adj. 0.1-20) |
| Junctional remodeling under steroid challenge | OCT/OCTA frames (vacuoles, pores); microscopy junction metrics; Raman band ratios; pSMAD2/3; VEGFC | Graph state-space network with image/spectral encoders; physics constraints | Time-courses of junction integrity, permeability, resistance | Coverage-guaranteed prediction sets; propose extra imaging or Raman bands if epistemic width > $\tau$J | Co-registered to $\Delta$P and shear; windowed analysis (e.g., 5-15 min) |
| Pathway attribution (ALK5 vs VEGFC balance) | pSMAD2/3; VEGFC/VEGFR3/ PROX1; Raman indices; TEER/$\Delta$P-Q | Structured causal graph/ SEM; multitask classifiers with SHAP attributions | Pathway activity scores; contributions to resistance change | Jackknife+ conformal for calibrated probabilities; counterfactual queries ('what-if') | Report with assay timestamps and batch-normalization factors |
| Dose-response & schedule optimization (steroids, ALK5 inhibitors, VEGFC supplementation) | Dose/time vectors; facility/ permeability trajectories; safety markers | Hierarchical Bayesian PK/PD; Gaussian-process response surfaces | ED50/EC50 posteriors; optimal dose/ schedule proposals | Expected improvement/ EHVI; safety-constrained optimization | Supports topical, intracameral, depot routes; device-agnostic |
| Active experiment design to reduce uncertainty | Model entropy/variance; candidate measurement menus (Raman bands, OCT time points, panels) | Bayesian optimization; constrained contextual bandits (Thompson sampling) | Next-best measurement set; projected uncertainty reduction | Stop/go when predictive-set width < thresholds ($\tau$C, $\tau$R) | Respects safety gates: laser power/dwell, current density, max $\Delta$P/shear |
| Cross-platform normalization and comparability | TEER frequency/area; Raman 520.7 cm$^{-1}$ reference; OCT scale; geometry/porosity metadata | Batch-effect correction (e.g., ComBat); domain adaptation | Harmonized feature space enabling pooled analyses | Drift monitors (EWMA/KL divergence); two-sample tests for shift | Metadata schema required; device details logged |
| Image/OCT feature extraction | B-scans, en face sequences; lumen patency; vacuole count/size; membrane deformation | UNet/CNN encoder + morphology; optical-flow for dynamics | Quantitative descriptors feeding GSSN/ regressors | Bootstrap CIs; calibration curves for derived counts | Resolution/ focus verified; voxel-to-$\mu$m scaling logged |
| Raman biochemical indexing | Spectra (e.g., 785 nm; 4-10 cm$^{-1}$); baseline-corrected bands; power/dwell metadata | Sparse regression (LASSO/ elastic-net); manifold embedding | Band-integrated biochemical indices; junction/ ECM signatures | Permutation tests for band significance; interval coverage checks | Silicon 520.7 cm$^{-1}$ reference; power limits per safety gates |
| Responder classification (treatment efficacy) | Pre/post facility; junction metrics; pathway scores; genotype modifiers | Penalized GLMs/ gradient-boosted trees; stacked with GSSN outputs | Probability of response; odds ratios for covariates | Platt/Isotonic calibration; decision thresholds by utility | Chip-to-chip random effects via mixed models |
| Risk stratification/ time-to-event (e.g., IOP elevation) | Baseline imaging; pathway scores; exposure history | Cox/ piecewise-exponential survival; Bayesian survival | Hazard ratios; predicted time-to-threshold | Brier/IBS calibration; prediction intervals | Optional for translational/ clinical use |
| Drift, anomaly, and QC monitoring | Feature distributions over time; $\Delta$P-Q linearity; TEER/Raman baseline drift | Unsupervised change-point detection; control charts; two-sample tests | Alerts and holds; auto-recalibration prompts | Guardrails block actuation when out of tolerance | Per QA Narrative (illustrative) |

TABLE 3-continued

| | | AI Analysis Focus - Investigation ↔ Engine Mapping (Illustrative and Non-Limiting) | | | |
|---|---|---|---|---|---|
| Investigation Focus | Primary Signals/ Features | AI Engine(s) | Key Outputs | Uncertainty & Decision Logic | Notes / Operating Windows |
| CRISPR/gene-therapy design & evaluation (optional) | Sequence features; off-target scores; chip-level rescue metrics | Sequence-to-function transformers; RL guide design; digital-twin simulator | Shortlisted constructs with predicted rescue/risk | Posterior update loop with experiment feedback | Vector payload/ tropism noted; segregate TM vs SC delivery |

Table 3 shows the mapping of applications to AI algorithms, inputs, outputs, and rationale (exemplary). Each row links a use case to the main algorithm(s), key inputs, expected outputs/decisions, and the reason that the approach is preferred, with the associated uncertainty and safety gates.

Purpose and structure. Table 3 functions as an implementation map: it shows how device-agnostic features (pressure/ flow, TEER, Raman indices, OCT/OCTA metrics, and omics) feed specific learning components; what each component returns; and how reliability is enforced. The last column makes explicit the safety and uncertainty handling, so that actuation and reporting remain governed by calibrated bounds rather than point estimates.

Core mechanistic layer. For mechanistic modeling of ALK5/VEGFC and junction dynamics, a physics-informed graph state-space model captures TM↔SC coupling and monotone relations between junction integrity and hydraulic resistance. Raman indices, OCT/OCTA junction metrics, pathway panels, and ΔP-Q features are ingested; the model outputs permeability/facility trajectories and causal attributions. Physiologic hard constraints and conformal prediction ensure estimates stay within plausible ranges and achieve coverage.

Perception/feature extraction. Imaging segmentation uses U-Net/Vision-Transformer backbones (with self-supervised pretraining) plus physics-aware post-processing to preserve lumen continuity and topology, yielding junction continuity, belt thickness, tortuosity, and quality scores from OCT/IF/ OCTA. Raman analysis couples lightweight band-ratio models with 1D CNNs to capture subtle biochemical shifts while preserving interpretability; bootstrap CIs and conformal residual sets flag out-of-distribution spectra.

Fusion and prediction. Multimodal fusion relies on modality-specific encoders with attention-based late fusion to form a unified latent state for downstream prediction/ control; masked fusion propagates epistemic uncertainty when modalities are missing and prevents actuation on partial evidence. For risk stratification (IOP rise), a survival model stacked with mechanistic forecasts yields absolute risk by horizon with credible bands and counterfactual drivers; isotonic calibration and conformal bands enforce reliability.

Screening, optimization, and PK/PD linkage. Drug screening uses mixed-effects dose-response with mechanistic consistency checks to deliver EC50/EMax and responder calls while controlling false discovery and enforcing viability/barrier/immune gates. Regimen optimization applies constrained Bayesian optimization and contextual bandits to propose dose/route schedules with confidence and monitoring plans; uncertainty gates defer action when bands are wide. Ocular PK/PD (compartmental ODE with hierarchical Bayes) links formulation and dosing to compartment exposures and exposure-effect relationships, returning posteriors and safe exposure bounds.

Design, simulation, and control. For gene/cell modulation, Bayesian optimization over sequence space is balanced by an off-target transformer to keep specificity high; penalties reject uncertain constructs. A differentiable digital twin enables counterfactual tests of junction dynamics under hypothetical controls; validation is against held-out chip runs with shrinkage to empirical priors. Post-implant sector control is handled by constrained MPC/safe policy gradient to respect actuator limits and sector coupling; policies are uncertainty-aware and hard-limited by tolerability constraints.

Operations & governance. Active learning (EVSI/knowledge-gradient) proposes the next experiment that most shrinks uncertainty per budget unit. Drift/anomaly detection monitors feature distributions over time/sites with simple, auditable statistics (PSI/KS) augmented by model-based checks; fail safes revert to conservative priors and trigger retraining under change control. Explainability uses Integrated Gradients/SHAP with monotone constraints to produce mechanism-consistent attributions and minimal-change recommendations; physics-violating explanations are rejected and logged. Calibration and deployment governance (temperature scaling, isotonic, conformal, model cards) provides coverage audits and rollback rules. Finally, chip→clinic transfer learning (CORAL/MMD/adversarial alignment) maps clinical latents to the chip manifold while detecting distribution shift; under high shift, mappings degrade conservatively and actions are gated.

Non-limiting scope. The specific algorithms and thresholds are exemplary. Substitutes or equivalents may be used so long as the system (i) ingests the standardized, synchronized features, (ii) enforces safety and uncertainty governance, and (iii) preserves the physics-informed coupling between junction state and hydraulic resistance that underlies prediction and control.

FIG. 15 shows acceptance metrics (illustrative). Predicted v measured facilities 1502 with a target 1:1 line and tolerance band. Uncertainty coverage 1504 comparing nominal confidence to empirical coverage. Baseline drift 1506 bounds (e.g., +10%) for stability of TEER and Raman indices during plateaus.

Overview. The platform accepts or rejects runs/models against three families of checks shown in FIG. 15. Thresholds are illustrative and may be tuned per device, cohort, or use case; novelty resides in enforcing consistent, device-agnostic criteria.

Predicted v measured facility 1502 (model concordance). Panel 1502 plots model predictions (x-axis) versus measured facility (y-axis) across chips/plateaus. Acceptance aims for slope≈1, intercept≈0, and tight residuals within a tolerance band around the 1:1 line.

Illustrative Gates:

Linear fit: slope 0.9-1.1, |intercept|≤0.05×median facility.

Goodness: $R^2 \geq 0.95$ (or MAE≤15% over 24 h across ≥6 chips).

Residual symmetry: median residual within ±2% of zero. Runs failing the band or goodness thresholds are quarantined and either re-fit or repeated under FIG. 4 calibration.

Uncertainty coverage 1504 (calibration). Panel 1504 compares nominal confidence (x) to empirical coverage (y) for prediction intervals (e.g., 50%, 70%, 90%). The target is the y=x line. Illustrative gates:

Each nominal level within ±5 percentage points of the diagonal.

Optional summary: max|coverage-nominal|≤0.05 or KS distance≤0.05. Coverage is computed with conformal sets or out-of-sample residuals using the synchronized matrix of FIG. 9.

Baseline drift 1506 (instrument stability). Panel 1506 tracks TEER and Raman indices during a no-perturbation window (e.g., 30 min baseline or long plateau). Dashed lines show a ±10% illustrative acceptance band. Gates:

|drift|≤10% for TEER and Raman;

No step changes at control events that lack physical cause;

Stability holds per channel and jointly (no cross-sensor divergence). Exceedances trigger recalibration (isotonic/temperature per FIG. 2) or run rejection.

Use in workflow. These metrics gate: (i) data admission to training; (ii) model release for Example 2-3 analyses; and (iii) controller enable for regimen selection (cf. FIG. 11-FIG. 12). Reports tabulate pass/fail counts, fitted slopes/intercepts, empirical coverage at each level, and baseline drift summaries, with links to raw logs and model hashes for auditability.

Figure 16:
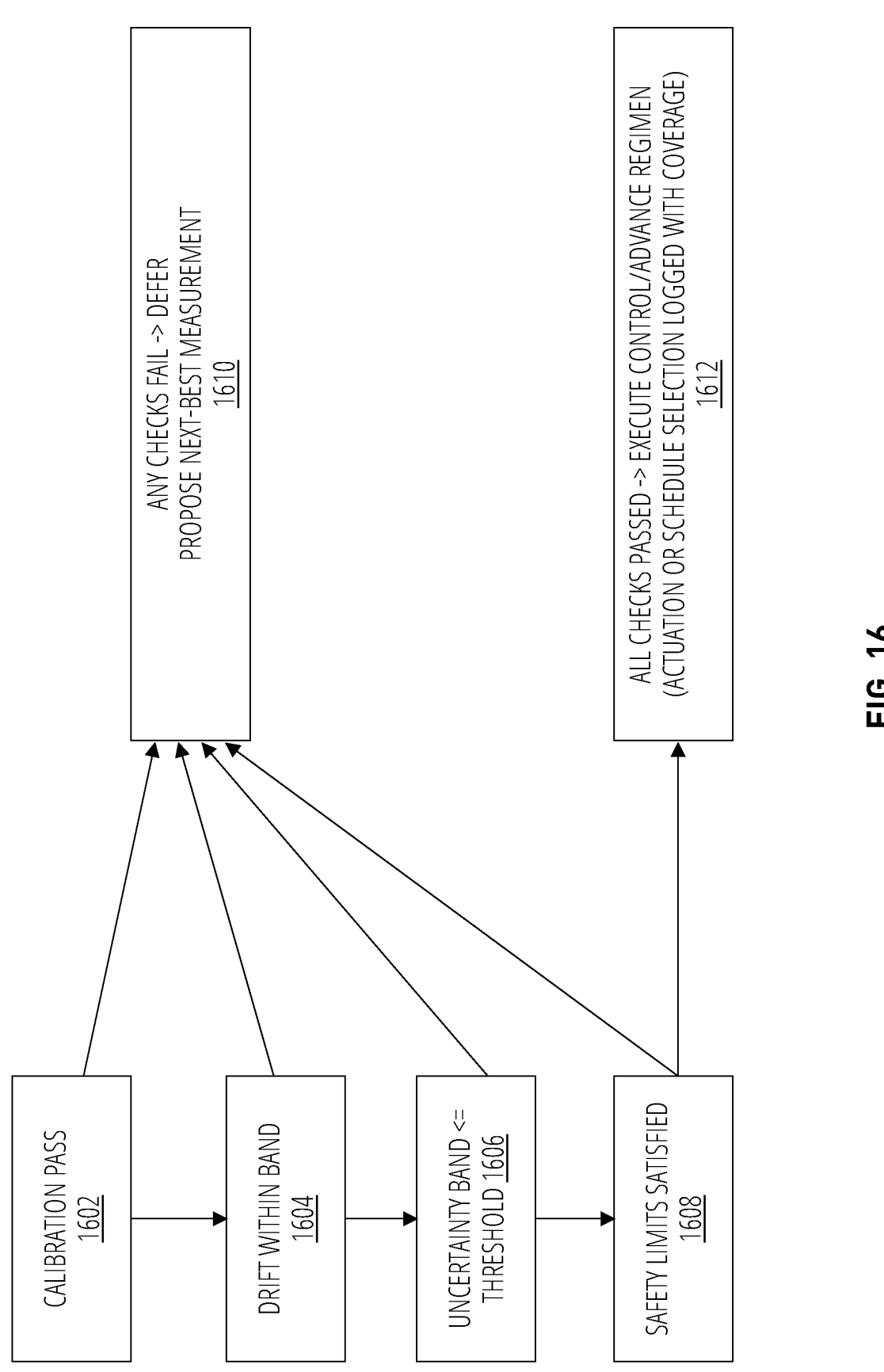
FIG. 16 depicts the acceptance and action gating logic.

FIG. 16 depicts the acceptance and action gating logic: data are admitted only if calibration checks pass 1602, drift remains within predefined limits 1604, predictive-uncertainty coverage is below a policy threshold 1606, and all safety limits are satisfied 1606; otherwise, the system defers and proposes the next-best measurement 1610.

The governance flow in FIG. 16 formalizes how the Ocular MPS system 102 decides to use measurements and whether to proceed with actuation or regimen advancement. Each run enters the pipeline at the calibration gate 1602, where instrument checks and reference standards are verified. Passing calibration routes the run to a drift assessment 1604 that compares short-term behavior of key signals, such as TEER, pressure-flow, and Raman intensity, against allowable variation windows. If drift is acceptable, the run advances to an uncertainty gate 1606 that evaluates the width of the model's predictive coverage bands generated from recent data. Coverage that is narrow enough to meet the preset policy threshold indicates adequate confidence. The final gate enforces safety limits 1608 on laser power, electrical exposure, pressure, shear, and any device-specific tolerances. Only when all four conditions are met does the system admit the data 1612, log the associated confidence, and execute the next control action or advance the dosing or scheduling regimen. If any check fails 1610, the system does not use the run for decision making; instead, it defers action, records the reason, and recommends a next-best measurement designed to resolve the specific deficiency, such as recalibrating a sensor, repeating a segment to remove drift, or collecting an additional imaging or spectral sample to tighten coverage. This governance loop ensures that every decision is both evidence-based and auditable, preventing model drift and unsafe operation while maintaining a clear trail linking data quality to downstream actions.

FIG. 17 illustrates implant-registered sector control. Volumetric OCT/OCTA is aligned to the stent's arc and micropore lattice 1702 to compute sector descriptors such as junction continuity and pulsatility 1704. These descriptors, together with implant QA priors (for example, micropore density and endothelial coverage), pass through uncertainty and tolerability gates to produce controller schedules 1706, such as elution duty cycles or micro-valve setpoints, that are coordinated with a steroid taper 1712 plan.

In clinical mode, the Ocular MPS system 102 anchors its analysis to the implanted device so that sensing, prediction, and actuation are all expressed in the same coordinate frame. A volumetric OCT or OCT angiography scan is first registered to the physical geometry of the implant, including its arc within Schlemm's canal and the pattern of micropores or outlets 1702. This registration yields a stable map that divides the canal into sectors matched to the device's architecture 1704. From the registered volume, the engine extracts sector-wise descriptors that reflect both structure and flow. Examples include junction continuity along the inner wall, local pulsatility as a surrogate for outflow activity, and other measures of patency. These descriptors are interpreted as candidate contributors to outflow facility and provide the context in which actuation will occur.

The controller does not operate on imaging alone. Prior information about the implant, such as the measured density of micropores and the extent of endothelial coverage observed during follow-up, is ingested as quantitative priors 1708. By combining these priors with current sector descriptors, the Ocular MPS system 102 estimates which sectors are most likely to respond to intervention and where control effort would be inefficient or unsafe. Before any schedule is issued the pipeline enforces gating based on uncertainty and tolerability gates 1710. Model coverage bands must be sufficiently tight, patient comfort limits must be respected, and intraocular pressure constraints must remain within bounds. When these conditions are met, the decision layer emits concrete control schedules, such as drug-elution duty cycles by sector or micro-valve setpoints for a reservoir-based device 1706. The schedules are time-aligned with the patient's steroid taper so that dose reduction and local augmentation are coordinated rather than competing 1712. All inputs, gates, and outputs are logged, allowing subsequent visits to adapt the sector plan as the tissue remodels or as new imaging reveals changes in patency.

Figure 18:
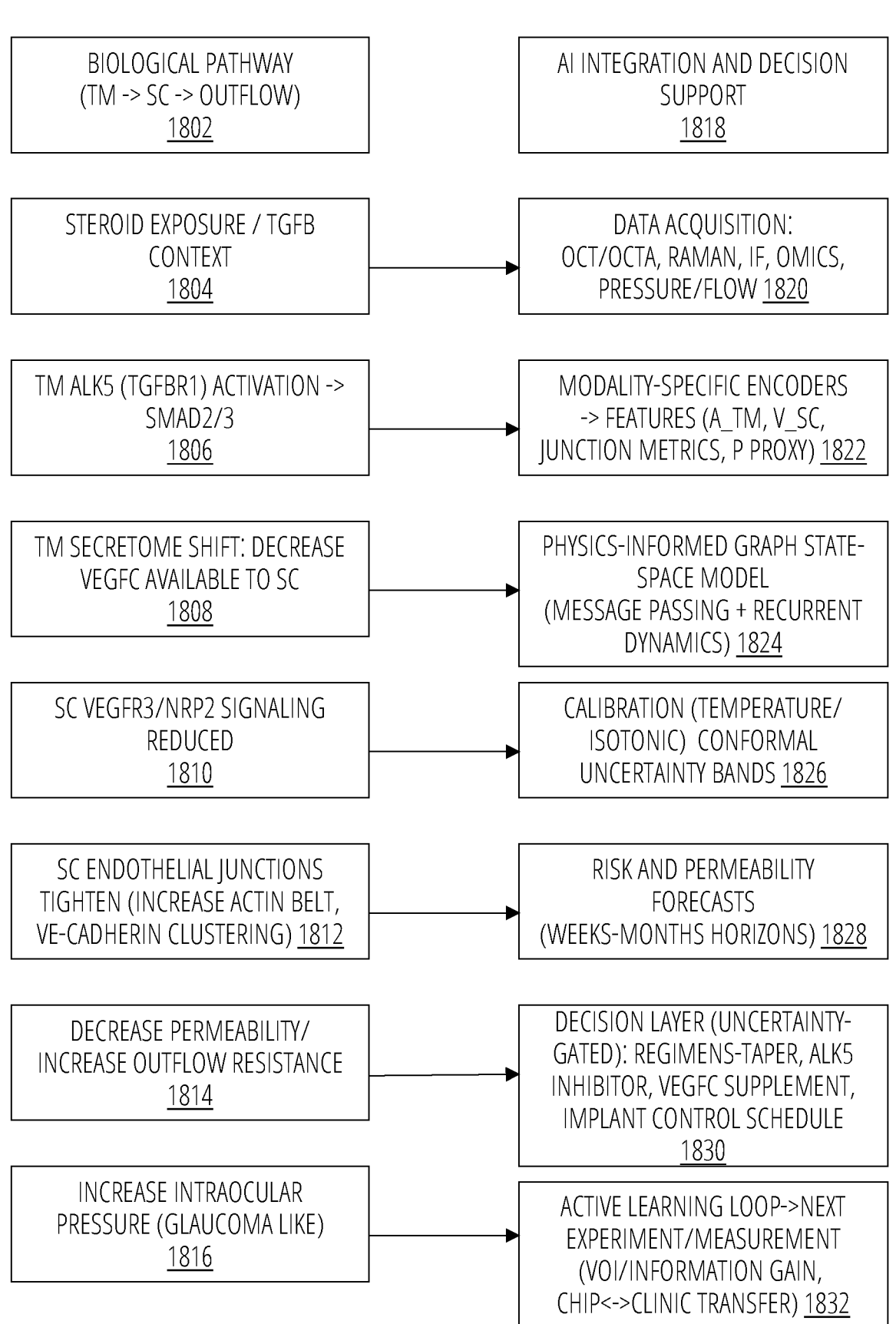
FIG. 18 shows a coupled biological pathway and AI integration (illustrative).

FIG. 18 shows a coupled biological pathway and AI integration (illustrative). The TM→SC pathway (left) maps one-to-one to the analytics and control stack (right): each biological step has a paired sensing/analysis block that ingests OCT/OCTA, Raman, immunofluorescence/omics, and pressure/flow, producing risk and permeability forecasts and regimen proposals.

FIG. 18 couples biology and analytics step-by-step. In the biological pathway 1802 (left column), a steroid exposure/ TGFβ context 1804 activates TM ALK5 (TGFβR1) →SMAD2/3 1806, shifting the TM secretome 1808 and reducing VEGFC available to SC 1808. As VEGFR3/NRP2 signaling in SC decreases 1810, SC endothelial junctions tighten 1812 (increased cortical actin belt, VE-cadherin clustering). The composite effect is lower permeability/ higher outflow resistance 1814, elevating interocular pressure 1816, unless counteracted.

AI integration and decision support 1818 (right column).

Data acquisition 1820. The platform collects OCT/OCTA, Raman, immunofluorescence/omics, and pressure/flow (ΔP-Q) under controlled load.

Modularity-specific encoders 1822. Each stream is transformed into device-agnostic features (e.g., a_TM, v_SC, junction continuity metrics, density/p proxies), time-aligned as in FIG. 9.

Physics-informed graph state-space model 1824. Features enter a graph state-space model (see FIG. 13) that represents TM and SC states (pathway activity, junction integrity, permeability) with recurrent dynamics and message passing between compartments.

Calibration (temperature/isotonic) 1826 & uncertainty. Temperature/isotonic corrections and conformal uncertainty bands enforce coverage and QA (cf. FIG. 4).

Risk and permeability forecasts 1828. The model yields permeability/facility and risk trajectories over relevant horizons (weeks-months).

Decision layer (uncertainty-gated) 1830. An uncertainty-gated controller recommends regimens (e.g., tapering schedules, ALK5 attenuation, VEGFC supplementation, or implant control settings), subject to acceptance metrics (see FIG. 17).

Active learning loop 1832. The system proposes the next measurement/experiment (dose, timing, or modality) to maximally reduce uncertainty and supports chip↔clinic transfer.

Generalization. The mapping is device-agnostic: alternative scaffolds, sensing stacks, or dosing actuators may be used so long as the biological steps can be sensed and the analytics consume the standardized feature set. This figure serves as the narrative bridge between the mechanistic pathway and the closed-loop AI workflow that implements screening, optimization, and control.

Drug Discovery—Companion Tables

These tables summarize the drug discovery workflow and map each stage to specific AI algorithms, inputs, outputs, and acceptance criteria, with explicit uncertainty and safety gating. Narratives below each table explain computation and decision rules. Values are exemplary for enablement.

TABLE 4

Discovery Lifecycle Stages ←→ AI Modules, Inputs, Outputs, and Acceptance Criteria

| Stage | Primary Goal | AI Algorithm(s) | Key Inputs | Outputs/ Decisions | Acceptance Criteria | Uncertainty & Safety Gating |
|---|---|---|---|---|---|---|
| Target hypothesis refinement | Quantify TM→SC causal ordering under steroid | Physics-informed graph state-space; Granger/ transfer entropy checks | Raman indices; p-Smad2/3 (TM); VEGFC (SC); junction metrics; pressure/flow | Direction-ality estimate; delay distribution; constraint verification | Monotone constraints satisfied; delay τ within physiological range | Calibration reliability ≥0.9; conformal coverage ≥0.9 |
| In silico triage | Prioritize compounds/ constructs for chip assays | QSAR; docking surrogate; network proximity; developability screens | Structures; target links; ocular ADME flags | Shortlist with rank and rationale | Developability pass; pathway proximity within top decile | Flag OOD chemotypes; defer if uncertainty band > threshold |
| On-chip triad assay | Measure efficacy vs controls | Orchestration + segmentation + spectral models | Dose ladder; OCT/OCTA; Raman; pathway panels; pressure/flow | Effect sizes vs vehicle/ positive controls | Sustained ≥25% resistance reduction within safety limits | QC pass; conformal band ≤5% for 1-3 mo horizon |
| Dose-response estimation | Quantify EC50/EMax with variance | Mixed-effects Emax/splines | Replicates across chips/doses/ time | EC50/EMax with CIs; goodness-of-fit | CI width ≤ preset; random-effects stable | Bootstrap CI; DEFER on wide bands |
| Mechanistic consistency | Verify ALK5→ VEGFC→ junction→ resistance | Constraint-regularized fit; counterfactual tests | Time-aligned molecular/ structural/ flow features | Pass/fail of mechanistic constraints; counter-factual deltas | All constraints pass; counterfactual matches within band | Defer if mismatch; schedule informative assay |
| Hit progression | Advance/ rework/ reject | Multi-criteria decision w/ Pareto front | Efficacy; safety; developability; uncertainty | Decision + rationale + monitoring plan | Meets efficacy & safety; manageable uncertainty | Gate when band width > policy or QC fail |
| PK/PD translation | Link dose/route to exposure/ effect | Compartmental ODE + hierarchical Bayes | Drug/ formulation; ocular volumes/ clearance | Exposure curves; exposure→ effect link | Credible intervals within bounds; tolerability respected | Conservative outputs when posterior wide |
| Regimen optimization | Select dose/route/ schedule | Bayesian optimization; constrained contextual bandit | PK/PD + efficacy; safety constraints | Regimen + confidence + monitoring plan | Meets target effect; constraints satisfied | Defer on wide bands; propose VoI measure-ments |

TABLE 4-continued

Discovery Lifecycle Stages ←→ AI Modules, Inputs, Outputs, and Acceptance Criteria

| Stage | Primary Goal | AI Algorithm(s) | Key Inputs | Outputs/ Decisions | Acceptance Criteria | Uncertainty & Safety Gating |
|---|---|---|---|---|---|---|
| Combination design | Evaluate combinations/ co-therapy | BO over combinatorial space; safe policy gradient | Pairwise effects; interaction terms | Combo schedule; expected gain | Improvement over monotherapy; safety maintained | Throttle exploration under uncertainty |
| Chip→clinic transfer | Project clinical features into chip manifold | Domain adaptation (MMD/ CORAL); similarity tests | Paired/ simulated features; clinical OCT/OCTA | Mapped latent; transport metrics | Similarity pass; external validation holds | Fallback to priors when shift detected |

Table 4 enumerates the main stages and the corresponding algorithms. Each acceptance criterion is defined a priori and logged with versioned models; uncertainty gates use conformal coverage on forecast errors to prevent overconfident advancement.

TABLE 5

In Silico Triage Metrics and Thresholds (Exemplary)

| Metric | Definition | Example Threshold | Rationale | Action if Fail |
|---|---|---|---|---|
| Pathway proximity score | Graph distance to ALK5/VEGFC nodes | Top 10% | Mechanistic relevance | Re-rank; seek orthogonal rationale |
| Ocular developability | Composite of solubility, stability, melanin binding, P-gp | Pass all subtests | Feasibility in eye | Reformulate or reject |
| Off-target risk | Predicted liability panel | Below risk index 0.2 | Safety | Filter or redesign |
| Novelty/coverage | Training set similarity for QSAR | Within convex hull or flagged | Model reliability | Conservative prior; extra assays |

Table 5 shows the in-silico triage metrics and thresholds (exemplary). Defines screening metrics (pathway proximity, ocular developability, off-target risk, novelty/coverage), their thresholds and rationale, and the action taken on failure to prioritize compounds for chip assays.

TABLE 6

Route/Formulation ↔ PK/PD Translation and Decision Rules

| Route/Formulation | Predicted Compartment Exposure | Constraints | Chip→Clinic Translation | Decision Rule |
|---|---|---|---|---|
| Topical (solution/gel) | Cornea→ Aqueous→ TM/SC (low peaks, frequent dosing) | Tear turnover; corneal permeability | Map chip effect at matched Cmax/AUC | Advance if target effect achieved within tolerability |
| Intracameral bolus | Aqueous→TM/SC (high early peak) | Procedure limits; transient spikes | Use short-window chip efficacy | Advance if spikes stay below safety threshold |
| Depot (sustained) | Stable TM/SC exposure | Device capacity; leachables | Long-window chip trajectories | Advance if steady-state meets target without accumulation |
| Vector-mediated expression | Compartment-selective production | Onset/offset kinetics; specificity | Chip transduction kinetics | Advance with promoter/targeting specificity |

Table 6 discloses the route/formulation↔PK/PD translation and decision rules. Maps dosing routes/formulations to predicted ocular compartment exposure, key constraints, chip→clinic translation method, and the advancement rule used to select clinically feasible regimens.

TABLE 7

Governance and Validation Artifacts

| Artifact | Purpose | Evidence Captured |
|---|---|---|
| Calibration & conformal logs | Show calibrated risks and coverage | Reliability curves; coverage stats |
| Mechanistic constraint checks | Verify ALK5→VEGFC→ junction links | Constraint residuals; pass/fail |
| Orchestration manifests | Document assay timing and controls | Schedules; QC results |
| PK/PD model cards | Link dose/route to effect | Parameter posteriors; safety bounds |
| Optimization traces | Explain regimen selection | EHI curves; constraint satisfaction |

Table 7 has the governance and validation artifacts. Lists calibration and conformity artifacts (e.g., reliability/coverage logs, mechanistic-constraint checks, orchestration manifests, and PK/PD model cards, optimization traces).

TABLE 8

Multimodal Model Notation

| Symbol/ Name | Description | Type/Domain | Notes/Examples |
|---|---|---|---|
| t, Δt | Time index and acquisition interval | Integers; seconds/minutes | Common run clock per FIG. 9 |
| $x\_t$ = [$a\_t${TM}, $v\_t${SC}, $j\_t$] | Latent state: TM ALK5 activity, SC VEGFC signaling, junction morphology | R^d (partitioned) | $j\_t$ includes continuity $J\_c$, belt thickness $T\_b$, tortuosity Y, relaxation constants |
| $u\_t$ | Controls (dose, route, ΔP/shear waveforms, implant actuation) | Structured control vector | Scheduler logs per run docket |
| $y\_t$ = {$r\_t$, $o\_t$, $m\_t$, $q\_t$, $p\_t$} | Observations: Raman $r\_t$, OCT/OCTA $o\_t$, IF markers $m\_t$, targeted omics $q\_t$, pressure-flow pairs $p\_t$ | Heterogeneous | Device-agnostic features after encoding |
| $z\_t$ | Encoded features from each modality | Concatenated latent(s) | $z\_t\hat{}r = E\_r(r\_t)$; $z\_t\hat{}o = E\_o(o\_t) \to (J\_c, T\_b, Y)$; $z\_t\hat{}q = E\_q(q\_t) \to (a\hat{}{TM}, v\hat{}{SC})$ |
| $ρ\_t$ | Outflow-resistance proxy from ΔP-Q | Scalar/unitized | $ρ\_t = E\_p(p\_t)$ |
| G | Two-node graph (TM, SC) with directed edges | Graph with edge features | Edge features $e\_{ji}$ include shear and steroid context |
| $f\_θ$ | Transition map (message passing + recurrent step) | Differentiable function | $x\_{t + Δ} = f\_θ(x\_t, u\_t, G) + w\_t$ |
| $w\_t \sim \mathcal{N}(0, Σ\_w)$ | Process noise | Random vector | Encodes unmodeled effects |
| $g(·)$ | Physics link junction → resistance | Monotone mapping | $∂ρ/∂T\_b \geq 0$, $∂ρ/∂J\_c \leq 0$ |
| $A\_θ$, $B\_θ$, $b\_θ$ | Linear heads on latent | Matrice/ vectors | Used after message-passing stack |
| ⊕ | Permutation-invariant aggregator | Operator | Sum/mean/attention pooling |

Table 8 shows the Modeling Symbols & Notation (Exemplary). Definitions of variables, operators, and mappings used by the physics-informed graph state-space model that fuses multimodal inputs (Raman, OCT/OCTA, TEER, ΔP-Q) to estimate facility/permeability, forecast resistance, and support control decisions. Symbols align with the synchronization scheme of FIG. 9 and the model structure of FIG. 10.

Table 8 consolidates the notation used throughout the modeling section so that the reader can trace how raw measurements become actionable estimates. The time index ttt and interval Δt\Delta tΔt refer to the synchronized acquisition clock (see FIG. 9). At each step, observations yty_tyt collect heterogeneous inputs—Raman spectra, OCT/OCTA images, immuno/omics panels, and pressure-flow pairs—which modality-specific encoders map to compact features ztz_tzt. Those features populate a latent state $$xt=[atTM,vtSC,jt]$$

that separates trabecular-meshwork ALK5 activity, Schlemm's-canal VEGFC signaling, and junctional morphology (e.g., continuity JcJ_cJc, belt thickness TbT_bTb, tortuosity Y\Upsilon Y).

System inputs utu_tut carry the controllable context (dose, route, and hydraulic/shear waveforms, with optional implant actuation). The model evolves by a differentiable transition fθf_\thetafθ on a two-node graph GGG (TM and SC) with directed, context-aware edges; message passing aggregates neighbor effects via the permutation-invariant operator ⊕\oplus⊕ before a recurrent update. A physics link g(•)g(\cdot)g(•) maps junction features to an outflow-resistance proxy ρtρ_tρt under monotone constraints—e.g., $$∂ρ/∂Tb≥0$$

and $$∂ρ/∂Jc≤0$$

to keep predictions physiologically plausible even with missing modalities. Linear heads (Aθ,Bθ,bθ) provide lightweight readouts from the latent state, while a zero-mean noise term $$wt\sim N(0,Σw)$$

absorbs unmodeled variability.

Together, these elements enable calibrated, device-agnostic inference: ztz_tzt standardizes inputs across instruments; xtx_txt captures coupled TM/SC dynamics; ρt and related outputs translate structure into facility/permeability estimates with uncertainty. The notation here is exemplary and non-limiting; alternative encoders or graph parameterizations may be substituted without departing from the scope of the claims.

TABLE 9

Manufacturing & Calibration Tolerances - Microengineered Device and Sensors

| Component | Parameter | Tolerance/ Spec | Calibration/QA Method |
|---|---|---|---|
| TM/SC microchannels | Height/width | ±5% | Profilometry; micro-CT sampling |
| Porous interface | Pore size/ porosity | ±10%/±5% | SEM sampling; flow bench |
| Pressure transducer | Linearity/ zero drift | $R^2 \geq 0.995$/ $\leq 0.5\%$ FS/mo | Ramp test; baseline hold |
| Flow sensor | Min detectable flow | $\leq 0.5$ μL/min | Traceable flow standard |
| Raman probe | Wavenumber accuracy | $\leq 1$ cm$^{-1}$ | Reference standard spectrum |
| OCT alignment | Phantom registration error | $\leq 10$ μm | OCT phantom check |
| Controller timing | Clock drift | $\leq 50$ ppm | Timebase sync procedure |

Table 9 lists components with acceptable ranges and calibration checks to support reproducibility across batches.

Table 9 lists manufacturing tolerances and calibration checks for the microengineered TM-SC device and its sensors. For each component, it specifies the controlled parameter, allowable range, and a traceable QA/calibration method to ensure lot-to-lot reproducibility and valid measurements.

Referring to Table 9, the device and sensing stack are released only when dimensional and metrological tolerances are demonstrated and documented with traceable records.

Channel geometry in the TM/SC microchannels is maintained within +5% for both height and width because these dimensions directly determine the shear and hydraulic resistance used by the state-space model; departures beyond five percent would bias ΔP-Q slopes and confound facility estimation. Each lot is sampled by surface profilometry and, on a periodic cadence, by micro-CT to verify wall uniformity. Substrates that fall outside tolerance are quarantined, and any runs performed with those parts are excluded from model fitting. The porous interface is similarly controlled by pore size and porosity-held within +10% and +5%, respectively, since membrane properties set the apparent permeability and mediate the link between junctional state and hydraulic resistance. Scanning electron microscopy supplies pore-size distributions, while flow-bench testing confirms effective porosity; if porosity is found to be below range, target shear and ΔP windows are adjusted or the lot is rejected outright.

Pressure sensing is qualified by a ramp test across the operating ΔP range to confirm linearity ($R^2 \geq 0.995$) and by a baseline hold to quantify zero drift ($\leq 0.5\%$ full scale per month). Instruments that fail either threshold are recalibrated or replaced, and any example runs occurring during drift excursions are flagged for the acceptance workflow referenced in FIG. 16. Flow sensing is verified against a traceable flow standard to confirm a minimum detectable flow of $\leq 0.5$ μL min$^{-1}$ so that low-flow plateaus used in facility estimation are reliably resolved; sensors that do not meet this sensitivity are removed from screening assays in which small changes in Q are decision-critical.

The Raman probe is calibrated to a wavenumber accuracy of $\leq 1$ cm$^{-1}$ using a reference spectrum, such as silicon at 520.7 cm$^{-1}$, to prevent systematic band shifts that would otherwise corrupt biochemical indices and undermine conformal coverage; this is checked daily before acquisition, and deviations beyond specification trigger an automatic flag. OCT alignment is validated by imaging a registration phantom to hold the phantom-to-chip coordinate error to $\leq 10$ μm; this is required for longitudinal junction metrics and for shear registration as depicted in FIG. 12. Misalignment initiates targeted rescans at the affected coordinates or removal of the affected data from analysis. Controller timing is synchronized to limit clock drift to $\leq 50$ ppm so that actuations and sensor sampling remain co-registered for state-space inference and acceptance windows; excessive drift pauses closed-loop operation until a resynchronization step is performed.

All calibration activities are governed by traceability requirements. Each calibration record carries the date, operator, standard identifier, and measurement uncertainty, and is attached to the run manifest. Geometry calibrations are performed per lot; sensor calibrations are performed on a monthly cadence; Raman and OCT checks are performed per session or per day unless a tighter cadence is specified by protocol. Nonconformances trigger DEFER actions commensurate with risk, including recalibration, exclusion of the affected data from training and decision making, or a rerun under the same protocol to restore data integrity.

Where desired, Table 9 may be expanded to include explicit columns for the sampling plan (for example, n≥3 wafers per lot with an AQL of 1.0), the calibration frequency (per lot, per day, or per month as appropriate to the component), the reference standard and traceability identifier (NIST or internal standard ID), and the prescribed action on failure (recalibrate, reject, or adjust model inputs). For geometry-critical steps, capability index targets such as Cpk≥1.33 can be noted to document manufacturing control relative to the specified tolerances. For each metrology method, the associated measurement uncertainty can be recorded to demonstrate that specification limits exceed the combined measurement error by an appropriate margin, thereby reinforcing that acceptance decisions are statistically defensible.

The numerical tolerances and methods described here are exemplary and non-limiting. Equivalent metrology and alternative bounds may be substituted provided they maintain functional equivalence—i.e., they do not materially alter shear, pressure-drop behavior, or sensing accuracy—and provided that they are enforced by the same calibration logs and acceptance gates described in FIG. 17.

Figure 19:
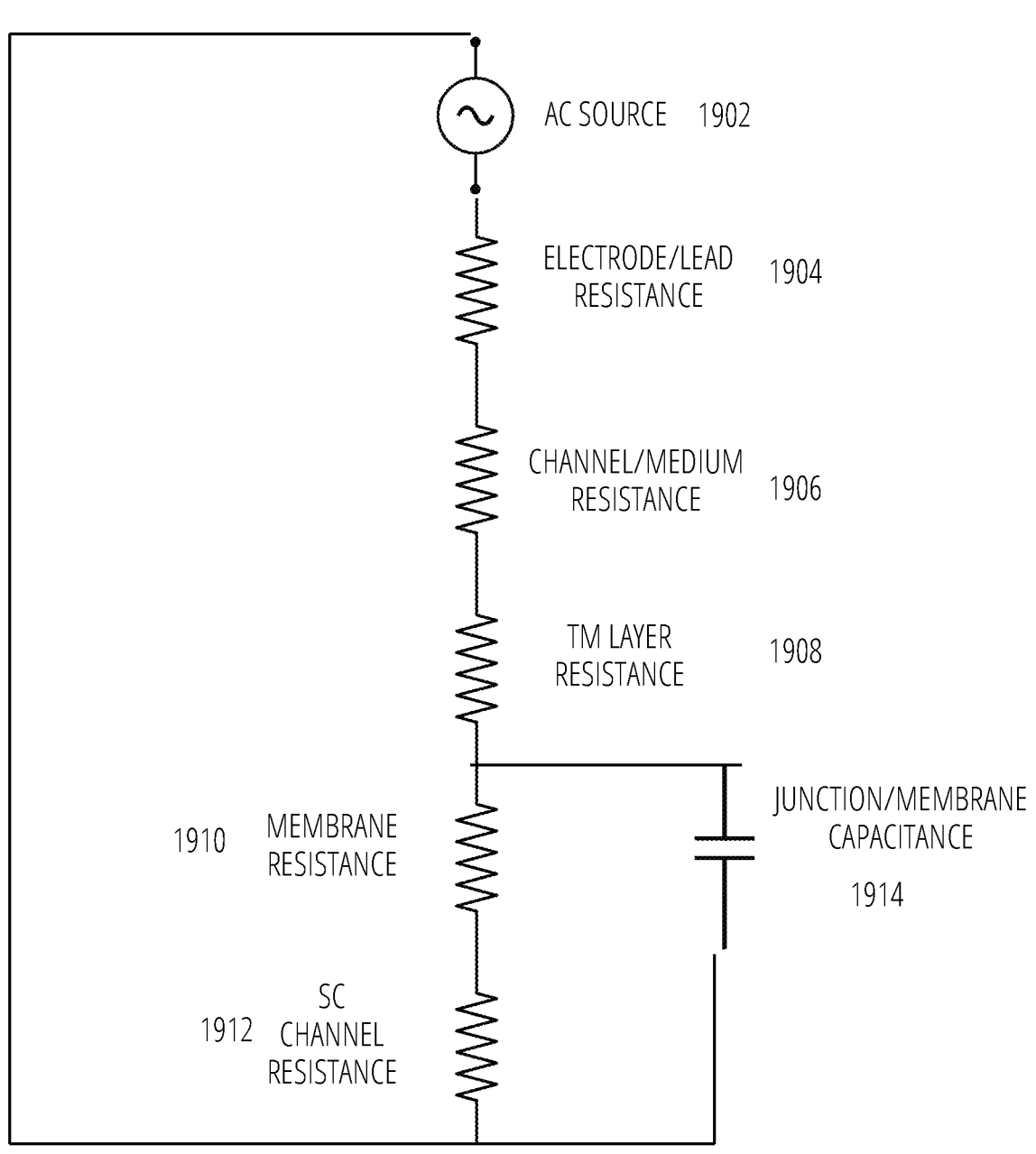
FIG. 19 illustrates the electrical configuration of TEER equivalent elements.

FIG. 19 shows the TEER equivalent elements (device-agnostic): series resistances for electrode/lead resistance 1904, channel/medium resistance 1906, TM layer resistance 1908, membrane resistance 1910, and SC channel resistance 1912 with a shunt junction/membrane capacitance 1914; TEER reported as (R_sample–R_blank)×area.

FIG. 20 is a flowchart of a TEER calibration and measurement workflow. (Illustrative). The workflow starts with device and electrode preparation 2002 leading to a blank/reference measurement 2004 and instrument calibration 2006. Samples are acquired with a small AC drive at pressure plateaus 2008, area-normalized TEER is computed 2010, and quality gates check drift, signal-to-noise, polarization, and frequency window 2014. Data that pass are time-aligned with pressure-flow, OCT/OCTA, and Raman and admitted to modeling 2018; failures are deferred for re-blank, re-seat, or frequency adjustment with re-acquisition as needed 2016.

Referring to FIG. 20, the TEER workflow begins with device and electrode preparation in which the chip is cleaned or wetted and the effective interface area and temperature are recorded 2002. A blank or reference run without cells, or at a verified open state, is acquired at the chosen drive frequency 2004, and the meter's lead compensation and frequency response are checked to confirm instrument calibration 2006. Experimental samples are then measured by applying a small AC stimulus across the orthogonal electrodes while the hydrodynamic program holds pressure plateaus 2008. The Ocular MPS system 102 computes the area-normalized resistance by subtracting the blank from the sample and multiplying by the recorded area 2010, with replicate statistics stored alongside the calibration record 2012. Quality assurance gates evaluate drift over a defined window, signal-to-noise, evidence of electrode polarization, and whether the measurement sits inside the validated frequency window 2014. If all checks pass, the run is admitted to modeling and time-registered with the synchronized pressure-flow trace, OCT/OCTA imaging, and Raman spectroscopy 2018. If any check fails, the pathway branches to deferral for troubleshooting, which can include reseating the electrodes, re-running the blank, or adjusting the frequency, followed by re-acquisition until the data meet acceptance criteria or are excluded from analysis 2016.

Figure 21:
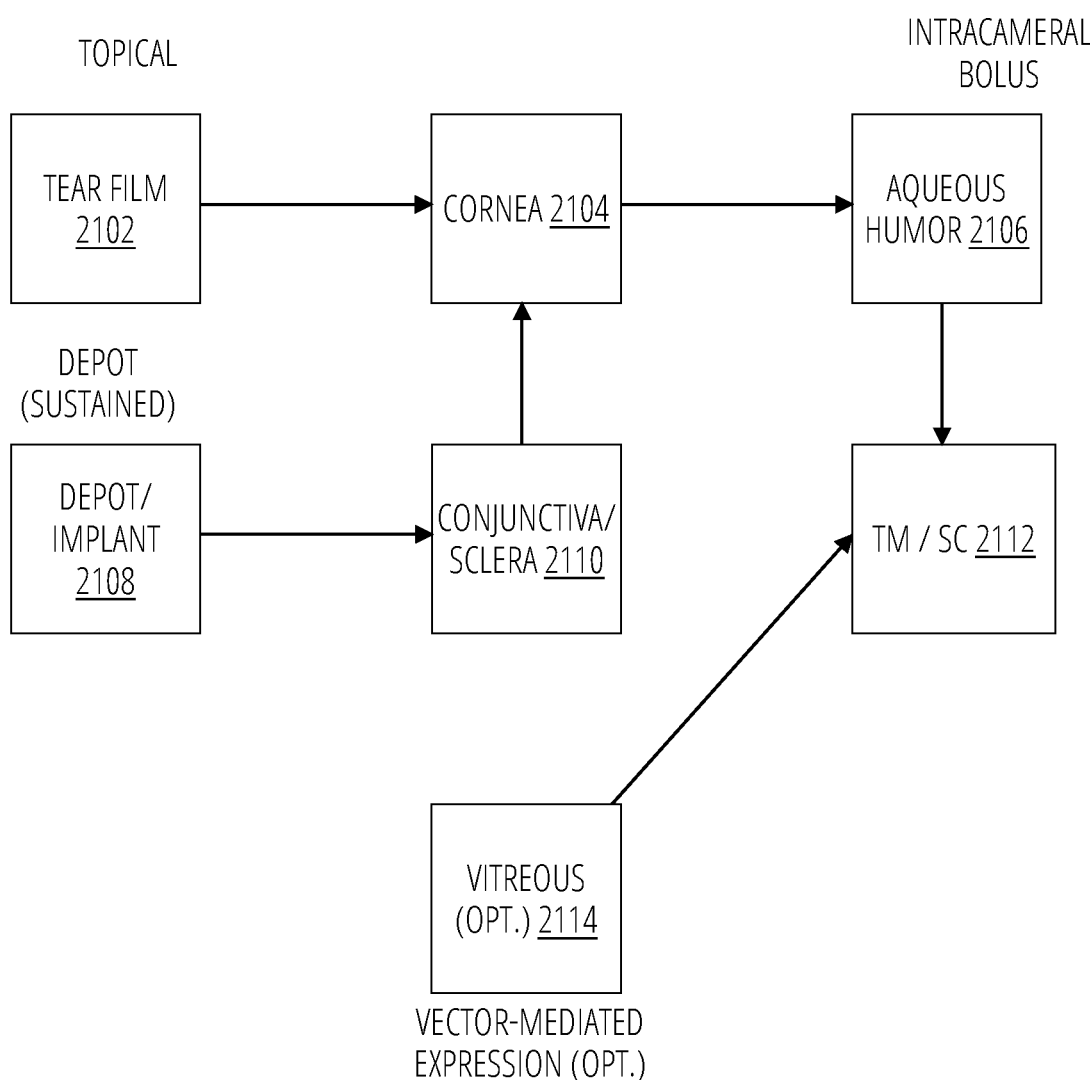
FIG. 21 shows the ocular PK/PD compartments and routes (Illustrative).

FIG. 21 shows the ocular PK/PD compartments and routes (Illustrative). Transport from topical, intracameral, depot, and vector-mediated routes to TM/SC 2112 compartments used for chip↔clinic translation.

3.0 Methodology 3.1 AI Focus

The Ocular MPS system 102 is directed to artificial-intelligence models and systems that fuse co-registered, load-dependent measurements, including TEER/impedance, pressure-flow (ΔP-Q), Raman spectroscopy, and OCT/OCTA/microscopy (optionally omics), to produce physics-informed estimates of facility and permeability, forecast intraocular-pressure trajectories, and drive uncertainty-gated experiment design. The Ocular MPS system 102 described herein is an exemplary implementation environment for generating these inputs; the AI pipeline is device-agnostic and operates with any equivalent platform that yields time-stamped, normalized signals co-registered to ΔP and shear. Model outputs are calibrated and accompanied by coverage-guaranteed uncertainty sets (e.g., conformal bands), and the system provides actionable recommendations for additional measurements or interventions. The methodology that follows enables these AI functions without being limited to any particular device geometry, fabrication method, scaffold, or vendor.

3.2 Scope Statement (Non-Limiting)

Parameter ranges and component choices in this section are illustrative; equivalents in adjacent ranges, alternative materials, and functionally similar layouts are contemplated. This section introduces a foundational, device- and pathway-agnostic workflow that later embodiments instantiate with pathway-specific markers, dosing schedules, or construct designs.

4. System Architecture (Device-Agnostic)

4.1 Platform Setup and Equilibration

An ocular MPS 104 is fabricated with adjacent micro-channels separated by a microporous interface coated with extracellular-matrix (ECM) proteins selected to emulate the juxtacanalicular region. Primary human trabecular meshwork (TM) and Schlemm's canal (SC) endothelial cells are expanded under serum-controlled conditions and introduced into their respective channels 506, 516. Seeding densities are adjusted until the trabecular meshwork cell layer 508 exhibits expected cytoskeletal stress-fiber orientation and the Schlemm's canal Lumen (bottom channel) 516 shows continuous junctional staining.

The ocular MPS 104 device is then perfused within about 0-10 mmHg pressure drop and about $0.5\text{-}5$ dyn·cm$^{-2}$ shear and equilibrated for not less than about 24 hours so that baseline permeability, TEER (area-normalized, blank-subtracted; about 100-10,000 Hz interrogation), and pressure-flow (ΔP-Q) measurements stabilize.

Operating windows (illustrative): TEER frequency about 100-10,000 Hz; Raman excitation about 785 nm, about 4-10 cm$^{-1}$ resolution, <5 mW at the sample; OCT/OCTA scan geometry per device optics; temperature about 36-37° C.; viscosity recorded for each medium lot.

4.2 Perturbation and Measurement

After baseline stabilization, a defined challenge (e.g., corticosteroid exposure) is applied with matched vehicle controls and, where appropriate, pathway-modulator arms. The Ocular MPS system 102 platform acquires concurrent readouts, including molecular panels at prespecified time points (for example, signaling markers and junctional proteins), label-free Raman spectroscopy 314 from the same device using the settings noted above, OCT/OCTA 312 and microscopy to visualize microstructural correlates such as vacuole frequency, pore metrics, and lumen patency, and continuous ΔP-Q 310 and TEER/impedance traces 308 to quantify facility and permeability.

Molecular panels at prespecified time points (e.g., signaling markers and junctional proteins).

Raman spectroscopy 314 to obtain label-free biochemical fingerprints (e.g., settings above) from the same device.

OCT/OCTA/microscopy 312 for structural correlates (vacuole frequency, pore metrics, lumen patency).

Continuous ΔP-Q 310 and TEER/impedance 308 traces for functional endpoints (facility and permeability).

Device geometry, medium viscosity, temperature, and other environmental conditions are logged as metadata. Cross-MPS normalization (e.g., area corrections, pore-size/height matching, viscosity normalization) aligns measurements across alternative scaffolds and geometries. For how these measurement streams map to AI engines and outputs, see Table 3.

4.3 Instrumentation, Calibration, Synchronization, and Analytics-Implementation Environment (Illustrative; Device-Agnostic)

The following describes an exemplary environment that generates the multimodal, load-coupled inputs used by the AI engines; equivalents are contemplated.

4.3.1 Electrodes and TEER/Impedance

Barrier integrity is quantified by TEER/impedance 308 using a frequency sweep of about 100-10,000 Hz (or a validated fixed frequency, for example, ~12.5 Hz), with blank subtraction and area normalization. Illustrative implementations include planar interdigitated electrodes 228, 230 patterned on the channel floor or ceiling, or paired miniaturized Ag/AgCl or Au/Pt electrodes placed on opposing sides of the porous interface to enforce symmetric current paths across the TM-membrane-SC stack 506, 508, 512, 516. Results are reported in Ω·cm$^2$ with a stability criterion of <about 10% drift over about 30 min prior to perturbation; electrode placement and geometry are recorded to support reproducibility and cross-device normalization. Safety gates limit electrode current density to avoid electrochemical or Joule-heating artifacts.

4.3.2 Pressure-Flow and Shear

A pressure transducer 222, 224 spanning TM-SC and an inline flow sensor 218 yield a synchronized resistance proxy. Standard operation imposes $\Delta P$ ramps of about 0-10 mmHg with flows of about 0.1-20 $\mu L \cdot min^{-1}$; facility ($C=Q/\Delta P$) and hydraulic resistance ($R\_h=\Delta P/Q$) are computed with geometry and viscosity reported. Shear over TM is held near about 0.5-5 dyn·cm$^{-2}$ (adjustable to about 0.1-20) using the parallel-plate approximation $\dot{\gamma}\approx6$ Q/(w h$^2$). Linear $\Delta P$-Q behavior is verified off-cell (r$^2$>0.98) to confirm instrument linearity.

4.3.3 Raman 204 Spectroscopy (Label-Free Biochemical Readout)

Near-IR excitation (illustratively 785 nm) 314 with spectral resolution of about 4-10 cm$^{-1}$ and back-scatter collection is used to obtain biochemical fingerprints at registered canal locations under load. Typical on-sample power is kept below about 5 mW with pixel dwell times of about 0.1-2 s to avoid photothermal effects; variants such as SERS (sensitivity), SRS/CARS (rapid CH-stretch imaging), or resonance Raman (chromophores) may be employed. Wavenumber calibration is verified against a silicon standard (520.7 cm$^{-1}$); peak drift and power/dwell are documented per run, and safety checks confirm no photothermal changes in adjacent frames before accepting data.

4.3.4 OCT/OCTA 312 and Microscopy (Structural Readouts)

En-face brightfield imaging captures vacuoles and pores; OCT B-scans traverse TM-SC for wall and lumen profiling; and OCTA or tracer/particle velocimetry quantify canal dynamics. Scan geometry (B-scan orientation, step size across the interface, and field-of-view) is recorded alongside optics (objective NA) to assure comparability. Morphological outputs include pore density/size, vacuole frequency, junction continuity/thickness statistics, and lumen patency, all co-registered to concurrent pressure/shear.

4.3.5 Operating Windows and Safety Gates 408

Illustrative settings include TEER frequency about 100-10,000 Hz; Raman about 785 nm with about 4-10 cm$^{-1}$ resolution and <about 5 mW on-sample; temperature about 36-37° C.; and $\Delta P$ and shear within ocularly relevant ranges, with viscosity logged per medium lot. The Ocular MPS system 102 enforces safety gates 408 before actuation, maximum Raman power/dwell, electrode current-density limits, and maximum $\Delta P$ and shear presets, and runs acceptance checks (TEER blanks, Raman wavenumber/power verification, OCT focus/scale calibration) at startup and per shift.

4.3.6 Acquisition and Synchronization Pipeline

All streams are time-stamped at acquisition and aligned to the experimental schedule. Preprocessing includes illumination correction, motion stabilization, spectral baseline removal, and control-derived normalization. Imaging yields junctional continuity, belt-thickness, spatial variance, and curvature-based tortuosity; Raman produces band indices from pre-specified windows; omics panels are reduced to pathway activity scores; and the pressure-flow pair provides a resistance/facility proxy. Features are embedded in a common latent space and supplied to a physics-informed graph state-space model that honors causal ordering from challenge to molecular change to junctional remodeling and fluidic consequence.

4.3.7 Model Outputs and Uncertainty

After calibration, the model estimates current facility and permeability at time t, predicts $\Delta$facility over prespecified windows, and generates IOP trajectories under standard physiologic assumptions. Each output is accompanied by a coverage-guaranteed uncertainty set (for example, conformal bands), and an experiment-design module proposes minimal additional measurements whenever an uncertainty gate is exceeded.

4.3.8 Governance, Acceptance Criteria, and Metadata for Reproducibility

The Ocular MPS system 102 tracks drift on Raman/imaging distributions, versions model artifacts with full lineage, and prevents actuation if critical sensors are missing or out of tolerance 412. Illustrative acceptance criteria include mean absolute error in facility≤about 15% over about 24 h across ≥about 6 chips, empirical uncertainty coverage within about ±5% of nominal across modalities, and baseline TEER/Raman drift<about 10% per 30 min prior to challenge. To ensure cross-MPS comparability, the record lists channel dimensions, interface thickness/pore geometry and porosity, surface chemistry and lots, cell sources/passages, media, temperature, TEER electrode geometry, Raman objective/NA and calibration, OCT scan geometry, and pump/compliance settings.

4.4 Synchronization and Feature Construction

Heterogeneous measurements are synchronized to a common timeline by interpolating continuous sensor traces to the molecular sampling grid and by correcting batch effects using control-derived normalization factors. Imaging is converted into quantitative descriptors of junctional continuity, tortuosity, and thickness; Raman spectra are reduced to band-integrated biochemical indices; phosphoprotein and gene-expression panels are summarized into pathway activity scores. Each feature set is co-registered to $\Delta P$ and shear.

4.5 Mechanistic Representation and Learning

The canal segment is represented as a physics-informed graph state-space model 304 in which TM and SC are nodes with latent states for junctional integrity, permeability, and other pathway-level variables; edges encode paracrine and biomechanical couplings. Message passing propagates information between compartments, and a recurrent transition maintains temporal memory of prior exposure and shear history.

The learning objective penalizes deviations from experimentally measured resistance/facility while enforcing soft constraints consistent with known monotone relationships (e.g., tighter junctions→lower permeability→higher resistance). Regularization encourages temporal smoothness and discourages biologically implausible oscillations. Training uses stratified splits that hold out entire chip-level experiments for validation; post-training calibration (e.g., conformal prediction) yields coverage-guaranteed uncertainty surfaced with each forecast.

4.6 Estimation, Forecasting, and Experiment Design

Once calibrated, the model estimates current facility and permeability at time, predicts the change in facility ($\Delta$facility) over prespecified windows, and generates intraocular pressure (IOP) trajectories under standard physiologic assumptions, each accompanied by an explicit uncertainty set.

When an uncertainty-set width exceeds a predefined threshold (e.g., >$\tau\_C$ for facility), an experimental-design module proposes the minimal additional measurements (e.g., targeted Raman bands, an interim OCT time point, or a confirmatory molecular panel) expected to most efficiently reduce epistemic uncertainty (see Section 3 for instrumentation and safety gates).

4.7 Prospective Validation and Updating

Model assertions are tested prospectively by executing predicted interventions on fresh devices and repeating acquisition. Discrepancies beyond tolerance are localized by ablation, data processing, causal structure, or constraint set, and corrected datasets update the model under change control. The loop repeats until prediction error converges to a preset acceptance criterion, producing a validated and interpretable map from exposure conditions to therapeutic recommendations, each annotated with predicted outflow restoration and associated uncertainty.

4.8 Governance, QA, and Safety Gates

Governance includes drift monitoring on Raman/imaging features, versioned and auditable model artifacts with full lineage, and reproducible training pipelines. Safety gates prevent actuation if critical sensors are missing or out of tolerance and include, without limitation: maximum Raman power/dwell, electrode current density limits for TEER, and maximum $\Delta P$ and shear presets. Calibration/QA steps (blank TEER checks, Raman wavenumber/power verification, OCT focus/scale calibration) are executed at start-up and per shift.

4.9 Acceptance Criteria (Illustrative)

Illustrative acceptance criteria include predictive accuracy—mean absolute error in facility$\leq$about 15% over about 24 h across $\geq$about 6 chips; uncertainty calibration—empirical coverage within about $\pm$5% of nominal across modalities; and signal stability—baseline TEER and Raman drift <about 10% per 30 min prior to challenge. Thresholds are non-limiting and may be tuned to device geometry, assay sensitivity, and intended use.

The following mapping summarizes, on an illustrative and non-limiting basis, how specific investigative aims align with primary signals, AI engines, outputs, and uncertainty-driven decision logic used by the disclosed system; operating windows and thresholds mirror the Methodology unless stated otherwise.

TABLE 10

| | | Focus of AI Analysis: Investigation ↔ Engine Mapping (Illustrative and Non-Limiting) | | | | |
|---|---|---|---|---|---|
| Investigation Focus | Primary Signals/ Features | AI Engine(s) | Key Outputs | Uncertainty & Decision Logic | Notes/ Operating Windows |
| Baseline facility & permeability under load | TEER/impedance (area-normalized); $\Delta$P-Q traces; viscosity-adjusted flow; geometry (w, h, L) | Physics-informed regression; Kalman/state-space smoothing | Facility C; apparent permeability Papp; drift-corrected baseline with CIs | Conformalized residuals; alert if CI width > $\tau$C or $\Delta$P-Q non-linearity ($r^2 < 0.98$) | $\Delta$P ≈ 2-6 mmHg (adj. 0-20); shear ≈ 0.5-5 dyn · cm$^{-2}$ (adj. 0.1-20) |
| Junctional remodeling under steroid challenge | OCT/OCTA frames (vacuoles, pores); microscopy junction metrics; Raman band ratios; pSMAD2/3; VEGFC | Graph state-space network with image/spectral encoders; physics constraints | Time-courses of junction integrity, permeability, resistance | Coverage-guaranteed prediction sets; propose extra imaging or Raman bands if epistemic width > $\tau$J | Co-registered to $\Delta$P and shear; windowed analysis (e.g., 5-15 min) |
| Pathway attribution (ALK5 vs VEGFC balance) | pSMAD2/3; VEGFC/VEGFR3/ PROX1; Raman indices; TEER/$\Delta$P-Q | Structured causal graph/ SEM; multitask classifiers with SHAP attributions | Pathway activity scores; contributions to resistance change | Jackknife+ conformal for calibrated probabilities; counterfactual queries ('what-if') | Report with assay timestamps and batch-normalization factors |
| Dose-response & schedule optimization (steroids, ALK5 inhibitors, VEGFC supplementation) | Dose/time vectors; facility/ permeability trajectories; safety markers | Hierarchical Bayesian PK/PD; Gaussian-process response surfaces | ED50/EC50 posteriors; optimal dose/ schedule proposals | Expected improvement/ EHVI; safety-constrained optimization | Supports topical, intracameral, depot routes; device-agnostic |
| Active experiment design to reduce uncertainty | Model entropy/variance; candidate measurement menus (Raman bands, OCT time points, panels) | Bayesian optimization; constrained contextual bandits (Thompson sampling) | Next-best measurement set; projected uncertainty reduction | Stop/go when predictive-set width < thresholds ($\tau$C, $\tau$R) | Respects safety gates: laser power/dwell, current density, max $\Delta$P/shear |
| Cross-platform normalization and comparability | TEER frequency/area; Raman 520.7 cm$^{-1}$ reference; OCT scale; geometry/porosity metadata | Batch-effect correction (e.g., ComBat); domain adaptation | Harmonized feature space enabling pooled analyses | Drift monitors (EWMA/KL divergence); two-sample tests for shift | Metadata schema required; device details logged |
| Image/OCT feature extraction | B-scans, en face sequences; lumen patency; vacuole count/size; membrane deformation | UNet/CNN encoder + morphology; optical-flow for dynamics | Quantitative descriptors feeding GSSN/ regressors | Bootstrap CIs; calibration curves for derived counts | Resolution/ focus verified; voxel-to-μm scaling logged |

TABLE 10-continued

Focus of AI Analysis: Investigation ↔ Engine Mapping (Illustrative and Non-Limiting)

| Investigation Focus | Primary Signals/ Features | AI Engine(s) | Key Outputs | Uncertainty & Decision Logic | Notes/ Operating Windows |
|---|---|---|---|---|---|
| Raman biochemical indexing | Spectra (e.g., 785 nm; 4-10 cm$^{-1}$); baseline-corrected bands; power/dwell metadata | Sparse regression (LASSO/ elastic-net); manifold embedding | Band-integrated biochemical indices; junction/ ECM signatures | Permutation tests for band significance; interval coverage checks | Silicon 520.7 cm$^{-1}$ reference; power limits per safety gates |
| Responder classification (treatment efficacy) | Pre/post facility; junction metrics; pathway scores; genotype modifiers | Penalized GLMs/ gradient-boosted trees; stacked with GSSN outputs | Probability of response; odds ratios for covariates | Platt/Isotonic calibration; decision thresholds by utility | Chip-to-chip random effects via mixed models |
| Risk stratification/ time-to-event (e.g., IOP elevation) | Baseline imaging; pathway scores; exposure history | Cox/ piecewise-exponential survival; Bayesian survival | Hazard ratios; predicted time-to-threshold | Brier/IBS calibration; prediction intervals | Optional for translational/ clinical use |
| Drift, anomaly, and QC monitoring | Feature distributions over time; ΔP-Q linearity; TEER/Raman baseline drift | Unsupervised change-point detection; control charts; two-sample tests | Alerts and holds; auto-recalibration prompts | Guardrails block actuation when out of tolerance | Narrative Per QA (illustrative) |
| CRISPR/gene-therapy design & evaluation (optional) | Sequence features; off-target scores; chip-level rescue metrics | Sequence-to-function transformers; RL guide design; digital-twin simulator | Shortlisted constructs with predicted rescue/risk | Posterior update loop with experiment feedback | Vector payload/ tropism noted; segregate TM vs SC delivery |

Table 10. Focus of AI Analysis: Investigation-Engine Mapping (Illustrative and Non-Limiting). Engines and thresholds may be tuned to device geometry, assay sensitivity, and intended use.

4.10 QA Narrative (Illustrative)

This section is illustrative and non-limiting; thresholds may be tuned to device geometry, assay sensitivity, and intended use. As an illustrative, non-limiting protocol, the platform performs start-up and per-shift checks to confirm operability and safety before any challenge or actuation. In brief: an acellular TEER blank is measured and area-normalized to establish a baseline and to record electrode geometry; Raman calibration is verified against the 520.7 cm$^{-1}$ silicon peak with laser power and dwell constrained within preset limits; OCT focus and scale are confirmed against a micrometer target and the scan geometry (B-scan orientation and step size) is logged; ΔP-Q linearity is validated off-cell (e.g., $r^2$>0.98) with viscosity recorded for the current medium lot; safety gates are confirmed for maximum Raman power/dwell, electrode current-density limits, and maximum ΔP and shear presets; and baseline stability is established prior to perturbation (e.g., TEER and Raman drift <about 10% over about 30 min). Deviations are documented with justification and may trigger extended equilibration, recalibration, or a hold on data acquisition.

4.11 Required Metadata for Cross-MPS Comparability

The Ocular MPS system 102 records, at minimum the channel width/height/length, the interface thickness/pore diameter and porosity, the surface coating chemistry and lot, the cell source/passage, the medium composition/viscosity, temperature, TEER electrode geometry, Raman objective/ NA and laser calibration, OCT scan geometry, and pump/ compliance settings. This metadata enables reliable cross-device normalization and reproducibility.

4.12 Notes on Scope and Terminology

This section uses ocular MPS as a device-agnostic term; specific device nicknames may be used in figure captions or examples for convenience only. Subsequent embodiments (e.g., ALK/VEGFC modeling; AI-guided genetic or pharmacologic modulation) adopt this workflow without limiting the general teachings presented here.

4.13 Outputs: Risk Stratification

Risk stratification in the Ocular MPS system 102 is the disciplined translation of multimodal evidence into forward-looking, calibrated probabilities that a given eye will enter an adverse trajectory of aqueous outflow obstruction and intraocular pressure elevation within clinically meaningful horizons. The Ocular MPS system 102 begins by absorbing the synchronized features described in Shared Instrumentation and the AI Deployment section, junctional continuity, belt-thickness and tortuosity descriptors registered to canal segments; Raman-derived biochemical indices linked to protein cross-linking and lipid order; pathway activity scores quantifying ALK5 activation in trabecular meshwork and VEGFC signaling in Schlemm's canal; and the outflow resistance proxy that ties these measurements to hydrodynamics. Each feature vector is time-aligned to steroid exposure schedules and, where applicable, to implant sector geometry so that risk is conditioned on both pharmacologic and anatomic context.

The core risk engine couples a physics-informed graph state-space model 304 with survival and generalized linear components to produce both instantaneous and cumulative risk. From the mechanistic model, the Ocular MPS system 102 forecasts trajectories of permeability and resistance under the controls actually applied; these forecasts are then summarized into covariates that drive a Cox or piecewise-exponential time-to-event model for intraocular pressure rise and a mixed-effects progression model for structural canal deterioration.

Calibration layers transform raw scores into well-calibrated absolute risks through temperature scaling and isotonic regression, and conformal prediction envelops each curve with distribution-free uncertainty sets so that every risk statement carries an explicit confidence band. The same machinery yields relative risk under counterfactual regimens, allowing clinicians to ask not only "what is the risk now" but "how would the risk change if steroid tapering were accelerated or if VEGFC supplementation were introduced."

Age and baseline phenotype are treated as first-class stratifiers rather than nuisances. Hierarchical models learn age-conditioned baselines for junction morphology and biochemical indices, and conditional normalization removes the drift expected from normative aging before risk is computed. Phenotypes derived from mechanosensitivity and pathway balance are preserved as interpretable latent classes within the model so that risk differences can be explained in terms of measured properties, such as a canal endothelium that remains mechanically responsive yet biochemically VEGFC-depleted versus one that is simultaneously stiff and signaling-impaired. This prevents spurious elevation of risk in older eyes that remain within age-appropriate manifolds and focuses attention on true deviations caused by steroids or disease.

In postoperative settings where an endothelial-integrated stent is present, risk is resolved by sector along the implanted arc. OCT and OCTA volumes are registered to the stent's arc length and micropore lattice, and sector-wise junctional descriptors are mapped to predicted outflow contribution by sector. The model then aggregates sector risks into an eye-level curve while preserving explanations that point back to specific sectors responsible for the forecast.

When a drug-eluting reservoir or controllable micro-valve is available, the risk engine emits control schedules, elution windows and duty cycles, reservoir adjustments, or follow-up imaging cadence, that minimize the integrated probability of entering a high-resistance regime subject to ocular tolerability constraints. These outputs are uncertainty-gated; if the conformal band exceeds a configurable width, the Ocular MPS system 102 withholds actuation and proposes the minimal additional measurement set predicted to collapse uncertainty efficiently.

Risk delivery is intentionally plain-language and decision-oriented. For each horizon, the Ocular MPS system 102 states the absolute probability of clinically meaningful pressure rise, the expected timing of peak risk, and the principal drivers ranked by their quantitative contribution, such as a recent increase in ALK5 activity preceding a decline in VEGFC or a sectoral drop in OCTA pulsatility near a cluster of micropores. Counterfactual statements accompany every report to articulate the smallest change in dose timing, steroid substitution, VEGFC supplementation, or implant control that would return the eye to an age-appropriate low-risk manifold. The same report includes a monitoring plan with interval recommendations and modality emphasis informed by value of information calculations-if Raman indices dominate uncertainty, the plan concentrates on biochemical sampling; if sectoral perfusion is equivocal, the plan extends OCTA dwell over the implicated arc.

Governance and safety complete the stratification loop. Every published risk curve is bound to a versioned model artifact and to the raw measurements that generated it; explanations are reproducible and traceable to specific frames and spectra. Drift monitors watch feature distributions across clinics and devices, and, when excursions beyond control limits are detected, the engine falls back to a conservative prior and flags the site for recalibration. In prospective deployment, a watchdog prevents downstream actuation when required modalities are missing or fail quality checks, ensuring that risk never drives therapy without adequate evidence. By anchoring risk assessment to measured mechanism, calibrated probabilities, and explicit uncertainty, this output layer turns complex chip-and-clinic data into reliable, auditable guidance for prevention, monitoring, and intervention.

4.14 Outputs: Risk Stratification

General Approach. Risk is computed by coupling a physics-informed graph state-space model 304, which forecasts permeability and outflow resistance under the actually applied controls, with statistical layers that produce absolute time-to-event probabilities of clinically meaningful intraocular pressure (IOP) rise. Calibration aligns raw scores to observed frequencies; conformal prediction provides distribution-free uncertainty sets so each risk percentage is accompanied by an explicit band.

Table 11 Columns. Horizon: the forward-looking time window for risk estimation (e.g., 1 month, 3 months, 6 months). Calibrated Risk of IOP Rise (%, 95% CI; Conformal Band): the absolute probability that IOP will exceed a clinically meaningful threshold; the 95% confidence interval arises from model calibration; the conformal band indicates a distribution-free uncertainty radius (e.g., +4%). Peak Risk Window: the interval within the horizon when instantaneous risk is highest. Principal Drivers (ranked): the top contributors to risk derived from local feature attributions constrained to respect known monotone relations among ALK5 activation, VEGFC signaling, and junctional tightening. Counterfactual Minimal Change: the smallest feasible adjustment in regimen, timing, or implant settings that returns the forecast to the age-appropriate low-risk manifold. Recommended Intervention: an uncertainty-gated regimen suggestion produced by a safety-constrained optimizer. Monitoring Plan (VoI-driven): an imaging/assay schedule prioritized by expected value of sample information; modalities with greatest expected uncertainty reduction are scheduled earlier or more frequently. Uncertainty Gate: PASS when conformal band width is ≤threshold and required modalities passed QC; DEFER when band width is above threshold or required inputs are missing.

Table 12 Columns. Sector ID (arc deg): a registration of OCT/OCTA volumes to the stent's arc length and micropore lattice; sectors index contiguous arc segments (e.g., 0-30°, 30-60°). Predicted Outflow Contribution (%): the model-based estimate of each sector's contribution to total aqueous outflow under current conditions. Sector Risk (%, band): the absolute risk that junctional tightening in this sector will drive a clinically meaningful rise in IOP within the stated horizon; the band is the conformal uncertainty radius. OCTA Pulsatility (norm.): a motion-contrast amplitude metric normalized to baseline (1.00); values below 0.85 suggest reduced flow dynamics. Junction Δ (thickness/continuity): the median change in junction belt thickness (μm) and the change in continuity (unitless) relative to the age-conditioned normal manifold. Proposed Control Schedule: an implant control program (e.g., drug-elution window, duty cycle, micro-valve setting) coordinated with systemic or topical steroid timing. Notes: phenotype flags (e.g., preserved mechanosensitivity), QC warnings, or trial-specific constraints.

Computation & Gating Rules. Calibration uses temperature scaling and isotonic regression on held-out data; conformal bands use residual-based sets at 90% coverage. Uncertainty gate default thresholds: conformal band width≤5 percentage points for 1-3 month horizons, ≤7 for 6-12 months, with all required modalities present and passing QC. When DEFER, the system proposes the minimal additional measurement set predicted to collapse uncertainty (e.g., focused OCTA dwell on a suspect sector or a Raman panel).

Edge Cases. If age-adjusted morphology remains within normal limits but biochemical indices deteriorate, risk is driven primarily by biochemical features and the monitoring plan prioritizes Raman/omics. If sector risks are discordant with outflow contributions, the optimizer prioritizes control schedules for high-importance sectors even if their absolute risk is modest, subject to tolerability. Conformal band indicates distribution-free uncertainty radius at 90% coverage. Values are exemplary for enablement.

TABLE 11

| | Eye-Level Risk Stratification Output (Exemplary) | | | | | | |
|---|---|---|---|---|---|---|---|
| Horizon (month) | Calibrated Risk of IOP Rise* (%, 95% CI; Conformal Band) | Peak Risk Window (weeks) | Principal Drivers (ranked) | Counterfactual Minimal Change | Recommended Intervention | Monitoring Plan (Vol-driven) | Uncertainty Gate |
| 1 | 18.4% (12.9-24.6); ±4.0% | 3-4 | ↑ ALK5→ ↓ VEGFC; junction thickening; OCTA pulsatility drop (temporal) | Advance steroid taper 7 days; single low-dose VEGFC supplementation | Topical ALK5 inhibitor qd × 4 weeks; reassess week 4 | Raman + OCTA in 2 weeks (temporal arc dwell) | PASS |
| 3 | 32.7% (24.1-41.2); ±6.5% | 8-12 | Persistent VEGFC depletion; increased tortuosity; stagnation near subsector S3 | Add weekly depot at week 8; restrict steroid to mornings | Topical ALK5 inhibitor qd + monthly depot; consider VEGFC vector if no response by week 10 | Monthly OCT/OCTA; Raman q6 weeks; add p-Smad if risk >30% persists | DEFER-acquire Raman at week 6 |
| 6 | 21.2% (14.0-28.3); ±5.8% | 20-24 | Mechano-sensitivity preserved; VEGFC remains sub-therapeutic | VEGFC booster at month 5 | Taper ALK5 inhibitor to qod; schedule single VEGFC booster | OCT months 5 & 6; discontinue Raman if normalized | PASS |

Table 11 is an eye-level risk stratification output (Exemplary). Calibrated absolute risk by horizon with conformal uncertainty, principal drivers, counterfactual minimal changes, proposed interventions, and Vol-driven monitoring plans. *IOP rise threshold defined as clinically meaningful elevation above baseline (e.g., ≥5 mmHg or per protocol). Conformal band indicates distribution-free uncertainty radius at 90% coverage. Values are exemplary for enablement.

TABLE 12

| | Post-Implant Sector Risk and Control Schedule (Exemplary) | | | | | |
|---|---|---|---|---|---|---|
| Sector ID (arc deg) | Pred. Outflow Contribution n (%) | Sector Risk (%, band) | OCTA Pulsatility (norm.) | Junction Δ (thickness/ continuity) | Proposed Control Schedule | Notes |
| S1 (0-30°) | 22 | 14 (±3) | 0.92 | +0.12 μm/ −0.06 | No elution; observe | Mechanosensitivity intact |
| S2 (30-60°) | 18 | 27 (±5) | 0.81 | +0.24 μm/ −0.11 | Elution 0700 daily × 10 days (30% duty) | Avoid overlap with steroid peak |

TABLE 12-continued

| | | | | | | |
|---|---|---|---|---|---|---|
| | Pred. Outflow | | OCTA | Junction Δ | Proposed | |
| Sector ID (arc deg) | Contribution n (%) | Sector Risk (%, band) | Pulsatility (norm.) | (thickness/ continuity) | Control Schedule | Notes |
| S3 (60-90°) | 25 | 35 (±6) | 0.77 | +0.31 μm/ −0.15 | Elution 1900 daily × 14 days (40% duty) + VEGFC booster day 7 | Highest-risk segment |
| S4 (90-120°) | 15 | 16 (±4) | 0.90 | +0.09 μm/ −0.04 | No elution; extend OCTA dwell | Low contribution but equivocal flow |

Table 12-Post-Implant Sector Risk and Control Schedule (Exemplary). Sector-wise risk resolution along a stent arc with predicted outflow contribution, OCTA pulsatility, junction deviations, and proposed control schedules. Sector IDs follow stent arc registration; contributions and risks are model-predicted and normalized to total outflow. Pulsatility is normalized to baseline (1.00). Junction deltas are median belt-thickness change and continuity drop versus age-conditioned normal.

TABLE 13

ΔP/Shear Programs and Admission Thresholds (Exemplary)

| Program Name | ΔP Steps (mmHg) | Shear (dyn · cm$^{-2}$) | Sampling Cadence | QA Checks Required | Admission Thresholds |
|---|---|---|---|---|---|
| Baseline Calibration | 0 → 2 → 4 → 6 | 1-2 (held) | TEER/OCT/ Raman at each plateau | Raman 520.7; ΔP-Q r$^2$ > 0.98; TEER blank | Drift ≤ 10%; coverage ≤ τ_C |
| Steroid Challenge | 2-6 (constant) | 0.5-5 (ramped) | Continuous ΔP-Q & TEER; imaging periodic | All baseline checks + temp/viscosity logs | Directional pSmad2/3 vs resistance; coverage ≤ τ_C |
| Dose-Response | 2-6 (constant) | 0.5-5 (held) | Per dose level: fixed cadence | Lot geometry; Raman/OCT alignment | EC50 CI width ≤ preset; safety gates |

Table 13 shows the in-silico triage metrics, thresholds, rationale, and actions. Lists screening metrics (e.g., pathway proximity, developability, off-target risk, novelty), their definitions, example thresholds, why they matter, and the action taken if a metric fails.

TABLE 14

Physics Constraints and Causal Links Enforced in the Model

| Relation | Mathematical Form | Rationale | Measured By |
|---|---|---|---|
| Junction belt thickness increases resistance | $\partial\rho/\partial T\_b \geq 0$ | Thicker belts impede OCT flow | |
| Junction continuity reduces resistance | $\partial\rho/\partial J\_c \leq 0$ | Continuous junctions OCT reduce leakage paths | |
| TM ALK5 activation reduces SC VEGFC signaling | $a\_TM \uparrow \Rightarrow v\_SC \downarrow$ | Antagonistic pathway coupling | Raman/omics |
| VEGFC increase opens junctions | $v\_SC \uparrow \Rightarrow T\_b \downarrow$ and $J\_c \uparrow$ | Paracrine support of patency | OCT/Raman |

Table 14 shows the route/formulation ↔PK/PD translation and decision rules. Summarizes how topical, intracameral, depot, and vector-mediated routes are translated into ocular exposures, the key constraints, and the rules used to advance or defer.

TABLE 15

| Calibration and Governance Log Schema (Traceable QA) | | | | | | |
|---|---|---|---|---|---|---|
| Instrument/ Component | Specification | Method | Frequency | Uncertainty | Action if Fail | Run Manifest Link |
| Pressure transducer | $R^2 \geq 0.995$; drift $\leq 0.5\%$ FS/mo | $\Delta P$ ramp; baseline hold | Monthly | $\pm X$ % | Recalibrate/ replace; flag runs | ID → manifest |
| Flow sensor | MDL $\leq 0.5$ $\mu L/min$ | Traceable flow standard | Monthly | $\pm X$ % | Remove from low-flow assays | ID → manifest |
| Raman probe | Wavenumber $\leq 1$ $cm^{-1}$ | Reference spectrum (Si 520.7) | Daily/ session | $\pm EX$ $cm^{-1}$ | Recalibrate; pause acquisition | ID → manifest |
| OCT alignment | Registration error $\leq 10$ $\mu m$ | Phantom alignment | Daily/ session | $\pm X$ $\mu m$ | Rescan or exclude | ID → manifest |
| Controller timing | Clock drift $\leq 50$ ppm | Timebase sync | Weekly | $\pm X$ ppm | Resync; pause closed-loop | ID → manifest |

Table 15 shows the governance and validation artifacts↔claims cross-walk. Catalogs calibration logs, constraint checks, orchestration manifests, PK/PD model cards, and optimization traces, and shows which claim elements each artifact supports and what evidence is recorded.

5. System Architecture (Device-Agnostic)

5.1 AI Deployment and Model Architecture

This section describes how artificial intelligence (AI) engines 110 are engineered, trained, validated, and updated. The AI engines 110 are expressly coupled to tangible data sources and actuators: they ingest sensor outputs from the eye-on-a-chip device (pressure and flow), optical measurements (OCT/OCTA and Raman), and molecular assays (transcriptomic and proteomic panels), and they return concrete actions that control experimental runs on the microfluidic platform or produce patient-specific therapeutic recommendations. By binding model inputs and outputs to physical instrumentation and defined laboratory and clinical workflows, the deployment avoids abstraction and enables reliable, reproducible operation in regulated environments.

The learning pipeline begins at the instrument interface, where raw streams are time-stamped and aligned to experimental schedules. Raman spectra are denoised and baseline-corrected before transformation into band-integrated biochemical indices. Imaging frames are registered to the canal segment and converted into quantitative descriptors of junctional continuity, tortuosity, and thickness. Pressure and volumetric flow traces are low-pass filtered to remove mechanical pump jitter and are integrated to yield an outflow-resistance proxy synchronized to each molecular snapshot. These heterogeneous features are then embedded into a common latent space by modality-specific encoders that are trained jointly so that information from trabecular meshwork and Schlemm's canal compartments can be fused without loss of causal structure.

The AI platform couples a device-agnostic ocular microphysiological system (MPS) with multimodal sensing and AI analytics to characterize, forecast, and modulate aqueous outflow. A representative MPS reconstructs the trabecular meshwork-Schlemm's canal (TM-SC) interface using primary human cells on a porous interface and is operated under controlled pressure drops ($\Delta P$) and shear to emulate physiologic loading. The Ocular MPS system 102 provides electrical, hydraulic, optical, and biochemical access to the TM-SC stack 506, 508, 512, 516 while maintaining compatibility with alternative scaffolds and substrates.

Instrumentation includes (i) perfusion and pressure/flow sensing for continuous $\Delta P$-Q (pressure flow) 310 monitoring; (ii) electrodes for TEER 308/impedance to quantify barrier integrity; (iii) optical access for structural/functional imaging (e.g., OCT/OCTA 312 and microscopy); and (iv) a spectroscopy port for label-free Raman spectra 314 readouts. Where required, molecular assays (transcript/protein panels) are sampled at defined time points. All streams are time-stamped and synchronized to experimental schedules, with device geometry, medium viscosity, and environmental conditions captured as metadata.

A standardized preprocessing pipeline denoises and calibrates raw signals, then converts them into quantitative features: pressure-flow segments into facility/resistance metrics; TEER into area-normalized barrier measures; imaging into descriptors of junctional continuity, vacuole/pore dynamics, and lumen patency; and Raman into band-integrated biochemical indices. Modality-specific encoders 316 embed these heterogeneous features into a common latent space while preserving causality and TM↔SC compartmental structure. Cross-MPS normalization aligns data from different scaffolds and geometries so that models trained on one device family generalize to others.

Core inference uses a physics-informed, graph state-space "digital twin" of the canal segment. TM and SC nodes carry state variables (e.g., junctional integrity, permeability), and edges encode paracrine/biomechanical coupling. Recurrent transitions propagate states forward under the actual control inputs (dose, $\Delta P$, shear). The loss function unifies measurement agreement (e.g., predicted vs. observed resistance) with soft constraints reflecting known monotone relationships (e.g., tighter junctions→lower permeability). Calibration layers and distribution-free uncertainty quantification (e.g., conformal prediction) turn raw scores into well-calibrated estimates with explicit confidence bounds.

Once calibrated, the model operates in two modes. In estimation/prediction mode, it fuses ongoing TEER/$\Delta P$-Q/ imaging/Raman to infer current barrier state and forecast near-term facility. In control/simulation mode, it evaluates hypothetical perturbations (mechanical or pharmacologic), ranks strategies by expected outflow restoration, and, when connected to the instrument scheduler, can suggest or execute closed-loop adjustments (e.g., dosing profiles, loading regimens) subject to safety gates. Governance features include data-drift monitors, change-controlled incremental updates, versioned model artifacts with full lineage, and explainability outputs (feature attributions and counterfactuals) to support regulated deployment.

This architecture is deliberately device-agnostic and assay-agnostic: it binds AI inputs and outputs to tangible measurements and actuators, yet leaves freedom to swap scaffolds, imaging optics, spectral modalities, or assay panels without departing from the document. The result is a reproducible, extensible framework for measuring, forecasting, and modulating aqueous outflow across diverse embodiments.

The core predictive model is a physics-informed graph state-space network. Trabecular meshwork and Schlemm's canal compartments are represented as nodes with state variables corresponding to activity and signaling of various biomarkers such as ALK5 and VEGFC, respectively. Message-passing steps propagate information from trabecular meshwork nodes to Schlemm's canal nodes and vice versa; a recurrent transition maps states forward in time under the experimental controls actually applied.

The loss function penalizes deviations between predicted and measured resistance while imposing soft constraints that capture known monotone relationships among ALK5 activation, VEGFC reduction, and junctional tightening. Calibration layers transform raw scores into well-calibrated probabilities, and conformal prediction wraps the outputs with distribution-free uncertainty sets so that every recommendation is accompanied by an explicit confidence radius.

5.2 Statistical Models

Statistical models complement the neural architecture to provide interpretable risk and outcome predictions. For pre-therapy risk assessment, a survival model such as a Cox proportional hazards or piecewise exponential model estimates time to clinically meaningful intraocular pressure elevation, with covariates drawn from baseline imaging, genetics affecting ALK5/VEGFC regulation, and prior corticosteroid exposure. For device-level experiments, mixed-effects regression captures between-chip variability in permeability rescue while isolating the fixed effects of dose, route, and co-therapy. For binary outcomes such as responder status at a prespecified window, generalized linear models with penalization avoid overfitting and yield odds ratios useful for protocol decisions. All statistical models are cross-validated, assessed for calibration with Brier scores and reliability plots, and reconciled with the neural engine via stacking or Bayesian model averaging so that the Ocular MPS system 102 retains both accuracy and interpretability.

Model updating is continuous and explicitly governed. Data-drift monitors watch Raman and imaging feature distributions and trigger intervention when deviations exceed tolerance, at which point an incremental training cycle is launched under change-controlled conditions. For pharmaceutical development, new chip assay results are ingested by a hierarchical Bayesian module that updates posterior beliefs about compound efficacy and safety while preserving uncertainty from small-sample regimes. Dosing, route, and formulation parameters are optimized with Bayesian optimization across multi-objective surfaces defined by permeability restoration, safety margins, and practical constraints; expected hypervolume improvement guides candidate selection.

Where regimen exploration occurs, a constrained contextual bandit with Thompson sampling balances exploitation of known effective regimens against exploration of uncertain ones while enforcing safety gates tied to ocular tolerability assays. Every update yields a new, uniquely versioned model artifact with complete lineage from raw observations through preprocessing, hyperparameters, and validation, enabling auditability and rollback.

Clinical deployment is realized as a containerized decision-support service and a laboratory orchestration service. In the clinic, the service receives baseline OCT/OCTA 312, Raman spectra 314, and genotype panels, returns risk scores with calibrated confidence, and presents a ranked list of therapeutic strategies that includes ALK5 inhibition, VEGFC supplementation, steroid substitution, or watchful monitoring with specified intervals. In the laboratory, the service controls the microfluidic hardware scheduler, programs dose profiles for challenge-treat cycles, and emits assay manifests listing the molecular and imaging time points to be collected. Recommendations are locked until the associated uncertainty bands fall below a configurable threshold; if uncertainty remains high, the system suggests the minimal additional measurements predicted to collapse epistemic uncertainty most efficiently.

Safety, transparency, and explainability are integral. Every recommendation is accompanied by local feature attributions that identify which measurements most influenced the decision, by counterfactual statements that articulate what experimental or clinical change would reverse an unfavorable prediction, and by guardrails that prevent actuation if critical sensors are missing or miscalibrated. Periodic re-validation is automatically scheduled, and synthetic challenge datasets are generated by the digital-twin simulator to stress-test edge cases the laboratory has not yet observed. Together, these deployment practices ensure that the AI engines 110 remain faithful to the underlying mechanism, responsive to new pharmaceutical evidence, and reliable across both experimental and clinical contexts.

An Ocular MPS system 102 includes: (i) a microfluidic device comprising a TM compartment, a porous interface at the TM-SC boundary, and an SC channel 104; (ii) perfusion and pressure control to impose defined ΔP and shear 108; (iii) embedded or adjacent electrodes for TEER 106, 228, 230; (iv) optical access for imaging and spectroscopy 210; and (v) a computing module for acquisition 106, synchronization 108, and AI-assisted analysis 110. The architecture accommodates multiple substrates (e.g., track-etched membranes, microfabricated SU-8 scaffolds, hydrogels) without altering the analytical framework.

5.3 Shared Instrumentation & Feature Encoders

To avoid repetition and ensure reproducibility across embodiments, this subsection consolidates the common instrumentation and feature-engineering steps. The eye-on-a-chip integrates a pressure transducer spanning the TM-SC channels and a volumetric flow sensor that together yield a synchronized outflow resistance proxy. Imaging comprises OCT/OCTA 312 of the canal endothelium for non-invasive structural readouts and confocal immunofluorescence of junctional markers including ZO-1, claudins, and occludins. A fiber-coupled Raman probe acquires Raman spectra 314 at the same registered coordinates to provide label-free biochemical fingerprints sensitive to protein cross-linking and lipid order.

Molecular assays quantify pathway activity in paired compartments: phospho-Smad2/3 and related ALK5 signatures in trabecular meshwork cells, and VEGFC transcript and protein abundance in Schlemm's canal cells. All sensor streams are time-stamped at acquisition and aligned to the experimental schedule; illumination correction, motion stabilization, spectral baseline removal, and control-derived normalization are applied before feature extraction.

Junctional continuity, belt-thickness statistics and spatial variance, and curvature-based tortuosity are derived from registered images; Raman band indices are computed from pre-specified windows; pathway activity scores are calculated from normalized omics panels; and the resistance proxy is computed from the pressure-flow pair. The resulting features are embedded in a common latent space and provided to the physics-informed graph state-space model referenced in AI Deployment and Model Architecture Tailored to ALK5/VEGFC. For clinical translation, OCT-derived canal metrics substitute for chip-only measurements and are mapped into the same latent space so that risk and therapy recommendations remain mechanistically aligned.

6. Measurements & Analytics 6.1 TEER/Impedance

Purpose: quantify barrier integrity across the TM-membrane-SC stack 506, 508, 512, 516. Setup: 100-10,000 Hz frequency sweep or fixed frequency (e.g., ~12.5 Hz); paired blank control. Output: TEER ($\Omega \cdot cm^2$) with area normalization and stability criterion (<10% drift/30 min).

Electrical measurements (TEER/impedance) report barrier integrity; hydraulic measurements ($\Delta$P-Q) report facility; imaging (e.g., OCT/en-face) captures morphology and pore/vacuole events; Raman spectroscopy provides label-free biochemical fingerprints under load. Signals are time-stamped and fused with device metadata. Preprocessing removes artifacts and normalizes across devices; models learn mappings from features to target endpoints (facility, permeability, barrier state), and can drive feedback control of flow or dosing.

6.2 Pressure-Flow ($\Delta$P-Q) & Facility

Purpose: estimate outflow facility/hydraulic resistance under defined load. Setup: impose $\Delta$P ramps (e.g., 0-10 mmHg) and log Q; compute $$R\_h = \Delta P / Q$$

and facility $$C = Q / \Delta P;$$

report geometry and viscosity.

6.3 Raman Spectroscopy (SERS/SRS/CARS)

Purpose: in-situ biochemical fingerprinting under load. Setup: near-IR excitation (e.g., 785 nm), 4-10 $cm^{-1}$ resolution, backscatter microscopy. Variants: SERS for sensitivity; SRS/CARS for rapid CH-stretch imaging; resonance Raman for chromophores. Output: peak/ratio features fused with TEER and $\Delta$P-Q.

6.4 Raman Excitation and Collection Geometry (Illustrative).

A near-infrared beam (e.g., 785 nm) 704 is directed normal to an optically clear imaging window 502 and focused to an interrogation spot 702 at the sample plane. Dwell time denotes the per-position integration interval before advancing to the next location (single-point, line, or raster). Back-scattered 708 photons are collected through the same imaging window 502 in an epi configuration; off-axis and fiber-coupled variants are contemplated. Laser power at the specimen is ≤5 mW and spectrometer 706 resolution is ≈4-10 $cm^{-1}$. The measured layer stack 506, 508, 512, 516 comprises a trabecular-meshwork analog 508, porous membrane 512, and an endothelialized Schlemm's-canal channel 516. Raman acquisitions are synchronized with $\Delta$P/shear loading and co-registered with TEER and OCT (see FIG.

6-FIG. 7). (Illustrative ranges, non-limiting: spot ~10-75 μm; dwell ~50-1000 ms, adjusted to meet safety SNR gates.)

6.5 OCT/OCTA & Microscopy

The imaging stack 506, 508, 512, 516 provides non-destructive measurements of microstructure and lumen dynamics within the TM-membrane-SC ensemble and converts those measurements into quantitative features aligned to the hydraulic loading state. In combination with TEER 308, Raman 314, and $\Delta$P-Q 310, these optical channels let the controller distinguish junctional tightening from loss of lumen patency and attribute changes in facility to specific structural modes.

6.6 Geometry and Setup

An en-face imaging window 802 spans the TM-SC field 506, 508, 512, 516 (see FIG. 8). The Ocular MPS system 102 acquires: (i) wide-field brightfield or phase-contrast images to visualize vacuoles and pores at the TM/SC interface; (ii) OCT cross-sections ("B-scans") 806,808,810,812, 814,816 traversing the TM-SC stack 506, 508, 512, 516 to resolve layer thickness and canal lumen boundaries; and (iii) OCT angiography (OCTA) or particle-tracking velocimetry to estimate motion/flow within the SC lumen. Scan geometry follows FIG. 8: serial B-scans 806,808,810,812,814,816 are tiled across the en face field 802, and one or more reference cross-sections 804 are revisited at a fixed cadence. Imaging timestamps are synchronized to the controller clock (FIGS. 9-10) so that each frame is tagged with the concurrent pressure drop $\Delta$P 904, shear setpoint, and actuation state.

Acquisition protocol (illustrative). Before each run, a scale/registration phantom (etched grid or fiduciary marks on the membrane frame) is captured to set lateral and axial pixel scales and to lock the coordinate frame to device geometry. En-face brightfield is captured continuously or in short bursts, while OCT B-scans 806,808,810,812,814,816 step across the canal at a defined pitch (e.g., tens to hundreds of micrometers, device-dependent). OCTA or particle velocimetry is interleaved at the same coordinates to record speckle-decorrelation or bead trajectories. The controller schedules these acquisitions immediately before, during, and after hydraulic transitions (e.g., $\Delta$P plateaus and ramps) to sample both steady-state structure and transient responses.

Feature computation. Raw volumes and frames are processed by modality-specific encoders and physics-aware post-processing to yield a compact set of structural and dynamic descriptors:

Pore/vacuole metrics (en-face): pore count density, equivalent diameter distribution, and nearest-neighbor spacing, obtained by segmentation with topology-preserving cleanup; vacuole formation rate from frame-to-frame differencing and persistence criteria.

Lumen patency (OCT B-scan): canal cross-sectional area, fraction of continuous lumen length across the scan set, and minimum wall-to-wall distance; junction continuity and belt-thickness indices at the TM-SC boundary.

Intraluminal dynamics (OCTA/velocimetry): qualitative patency score from decorrelation magnitude, or quantitative axial/planar velocity estimates from particle tracks; pulsatility or intermittency indices when applicable.

All features are written into the synchronized feature matrix (FIGS. 9-10), co-registered to $\Delta$P 904 and shear, and aligned with TEER 908 and Raman 910 features for downstream fusion.

Calibration, QA, and acceptance. Prior to experimental runs, axial and lateral scaling are verified against the phantom; focus and SNR thresholds are checked, and motion is evaluated by frame-to-frame registration residuals. During acquisition, QC flags are raised if SNR, contrast, or registration drift falls outside bounds. Acceptance criteria mirror FIG. 16 and Table 10, e.g., (i) lumen continuity metrics reproducible within predefined limits across adjacent B-scans; (ii) vacuole-rate estimates stable under repeated captures at constant load; (iii) uncertainty coverage for derived features within target bands. Failed checks trigger reacquisition or exclusion by the orchestration layer without halting the entire run.

Relevance to mechanism and control. The imaging features separate TM-side mechanisms (junction tightening, reduced pore frequency) from SC-side mechanisms (loss of canal patency, vacuole scarcity). When integrated with TEER and $\Delta$P-Q, the learning system maps these descriptors to facility and permeability and attributes changes to specific biological pathways (cf. FIG. 14). In closed-loop embodiments, the controller uses these imaging-derived signals to schedule additional measurements (active learning), to halt runs that breach safety gates (e.g., suspected barrier failure), or to adjust actuation (e.g., shear waveform or dosing cadence) to drive the Ocular MPS system 102 toward higher facility without violating constraints.

Illustrative parameter ranges (non-limiting). Frame rates, scan pitch, and field-of-view are selected to balance SNR and temporal resolution and are not limited to a particular manufacturer or wavelength band. Light exposure remains within safety gates defined elsewhere in the specification. The approach is compatible with brightfield or phase-contrast microscopy, OCT at various center wavelengths, and OCTA implementations based on amplitude or phase decorrelation; particle velocimetry may use neutrally buoyant tracers when permitted by the protocol.

Device-agnostic generality. The analysis operates in a coordinate system defined by the imaging window 528 and taps 222,224 (FIGS. 5-6), so results are comparable across chips, scaffolds, and materials. By defining pore/vacuole, junction, and lumen features in universal terms and co-registering them to $\Delta$P and shear, the method supports cross-MPS normalization and enables predictive, hypothesis-driven control across pharmacologic, genetic, or mechanical interventions.

6.7 AI Fusion & Modeling

Purpose. The modeling layer unifies heterogeneous measurements, spectral (Raman spectra 314), imaging (OCT/OCTA 312, brightfield), electrical (TEER 308), hydrodynamic ($\Delta$P-Q 310), and optional omics, into a single latent state that predicts facility and permeability, stratifies responders, and, in certain embodiments, drives closed-loop control while enforcing safety and uncertainty gates.

6.8 Inputs and Synchronization

Sensor streams are time-aligned to the controller clock as in FIG. 9. Each observation at time ttt carries: (i) the raw measurement, (ii) acquisition metadata (exposure, focus/ SNR, temperature, geometry), and (iii) the concurrent load state (pressure drop $\Delta$P 904, shear). The result is a synchronized feature matrix that is portable across devices and experiments.

6.9 Modality Encoders (Setup)

To retain manufacturer independence, raw measurements are converted to compact, standardized features using modality-specific encoders 316:

Spectral encoder. A 1-D convolutional or band-ratio model maps baseline-corrected Raman spectra to biochemical indices (e.g., cross-linking and lipid-order ratios) and pathway surrogates (e.g., ALK5/VEGFC signatures).

Vision encoder. A lightweight U-Net/ViT backbone (self-supervised pretraining) transforms OCT/OCTA and en-face microscopy into junction continuity, belt thickness, tortuosity, vacuole/pore density, lumen patency, and pulsatility features; physics-aware post-processing preserves topology (canal continuity).

Hydrodynamic encoder. $\Delta$P-Q traces yield facility C=Q/ $\Delta$PC-Q/$\Delta$PC=Q/$\Delta$P, resistance Rh=$\Delta$P/QR_h=$\Delta$P/ QRh=$\Delta$P/Q, and drift-corrected baselines.

Optional omics/IF encoder. Targeted panels (e.g., pSmad2/3, VEGFC/VEGFR3) are mapped to pathway activity scores.

Encoders 316 write to a shared latent interface with missing-modality masks so that any subset of instruments may be used without retraining.

6.10 Cross-MPS Normalization

To enable pooling across chips, scaffolds, or materials, the platform performs cross-device normalization: (i) geometry-aware scaling (e.g., area-normalized TEER, channel-height normalization), (ii) illumination/temperature correction for spectra and imaging, and (iii) site/batch shift mitigation by domain adaptation (e.g., CORAL/MMD) when transferring between labs or to clinic mode. Normalization parameters are versioned and auditable.

6.11 Fusion and Physics-Informed Head

Encoder outputs zt(k) are fused by attention-based late fusion into a latent state sts_tst that represents the instantaneous junctional and canal condition. A physics-informed head (see FIG. 13) links sts_tst to facility/permeability using monotone constraints consistent with the hydraulic stack:

Increased junction continuity and decreased belt thickness predict higher facility and lower resistance; the converse predicts tightening.

Lumen patency and vacuolization in SC positively modulate facility.

Constraints are enforced by monotone layers or penalty terms and keep outputs physiologically plausible even when data are sparse.

In some embodiments, the head takes the form of a graph state-space model with TM and SC nodes and message passing between them (TM→SC paracrine coupling; shear/ $\Delta$P edges), enabling short-horizon forecasts of C(t) and Rh(t).

6.12 Training Objectives and Governance

Models are trained on synchronized runs with a composite loss: prediction error on facility/permeability, constraint penalties (monotonicity and permeability laws), and regularization. Calibration and data lineage (preprocessing versions, hyperparameters, acceptance gates hit/missed) are logged for each model artifact.

6.13 Uncertainty, Calibration, and Gating

To support regulated use, probabilities and intervals are calibrated (temperature scaling, isotonic) and banded with split-conformal prediction. Coverage and bandwidth are recorded (see FIG. 16; Table 10). Control actions are gated—the Ocular MPS system 102 withholds actuation when bands exceed policy thresholds or when QC flags a modality drift.

6.14 Outputs

Primary: facility and permeability estimates with confidence bands; forecasted trajectories over a user-defined window.

Responder stratification: subject/device-level classes (e.g., ALK5-dominant tightening vs. SC patency deficit), with ranked drivers (feature attributions constrained by the physics).

Diagnostics: drift and anomaly alerts; cross-modal agreement scores; acceptance-metric dashboards (predicted-vs-measured concordance, baseline drift bounds).

6.15 Closed-Loop Control (Optional Embodiment)

When enabled, the latent state feeds a decision layer, e.g., constrained Bayesian optimization or model-predictive control, that proposes dose/route/schedule or actuator settings (shear waveform, implant elution duty cycle) subject to safety limits (laser power, current density, $\Delta P$ maxima). Actions are executed only if uncertainty gates pass; otherwise, the Ocular MPS system 102 schedules active-learning measurements (e.g., an extra OCT time point or targeted Raman bands) expected to shrink the bands most efficiently.

6.16 Safety and QA Integration

Every prediction and action is accompanied by (i) QC status of each modality, (ii) calibration residuals, and (iii) acceptance-metric checks from FIG. 16 (e.g., coverage within +5%, baseline drift within bounds). Failures trigger conservative fallbacks (e.g., re-acquisitions, revert-to-nominal schedule).

FIG. 22 shows a flowchart of the active learning flow under governance gates. When any calibration, drift, coverage, or safety gate fails 2204, the Ocular MPS system 102 selects a next-best measurement (e.g., Raman band, OCT/OCTA time point, or TEER step) 2210 subject to power and electrical limits 2214, ingests the result 2216, updates the model 2208, and re-checks the gates 2206; if all gates pass, the regimen or control schedule executes with coverage logged 2206.

6.17 Relevance

This fusion layer is the bridge between raw sensor data and clinically meaningful outputs. It (i) generalizes across hardware and scaffolds via device-agnostic features and cross-MPS normalization, (ii) localizes a mechanism (TM tightening vs. SC patency) to explain why facility changes, and (iii) enables closed-loop optimization of pharmacologic and mechanical interventions while staying inside calibrated uncertainty and safety constraints. The approach supports the Examples in Section 7, the acceptance metrics of FIG. 16, and the claim elements covering multimodal estimation, prediction, and control.

6.18 QA/Calibration & Safety

Purpose. To ensure that measurements are reproducible across devices and runs and that all optical, electrical, and hydraulic exposures remain within predefined safety limits. The platform performs pre-run calibration, run-time quality control, and post-run acceptance checks before any data are admitted to modeling or control.

6.19 Pre-Run Calibration (Illustrative, Non-Limiting)

Optics (Raman/OCT). A wavenumber standard (e.g., silicon at 520.7 cm$^{-1}$) is acquired at start-of-day and before each batch. The peak position must fall within a preset tolerance (illustratively $\leq\pm1$ cm$^{-1}$) and spectral resolution is verified ($\approx$4-10 cm$^{-1}$). Laser power at the sample is measured at the imaging window 210 and limited by policy (illustratively $\leq$5 mW) with duty-cycle/dwell controls loaded to the controller. OCT is checked against a registration phantom to confirm lateral/axial scale and to set the en-face coordinate frame used for co-registration (FIGS. 9-10).

Electrical (TEER/impedance). Cell-free "blank" devices are filled with the working medium to establish baseline resistance and phase. The TEER 308 measurement chain is verified with a small-signal AC stimulus (no DC bias;

waveform and amplitude within safety, e.g., current density below a conservative limit). TEER electrodes 228, 230 are inspected for polarization/offset; area normalization and blank subtraction are applied per specification (TEER= (R_sample–R_blank)$\times$A).

Hydraulics ($\Delta P$-Q (pressure flow) 310). Pressure transducers 222, 224 undergo a ramp test to confirm linearity (illustratively $R^2 \geq 0.995$) and zero stability. Flow sensors 222, 224 are referenced to a traceable standard down to the minimum detectable flow (e.g., $\leq$0.5 $\mu$L min$^{-1}$). A leak test is performed by holding a set $\Delta P$ and confirming drift within bounds over a fixed interval (e.g., $\leq$2% over 5 min) with bubbles purged before test.

Thermal/medium. Bath temperature is stabilized (illustratively 37° C.$\pm$0.5° C.) and recorded alongside measured viscosity for later normalization. If equipped, a micro-thermistor at the window provides a baseline for photothermal monitoring.

Timing/registration. The controller clock is synchronized (e.g., $\leq$50 ppm drift) and the imaging/TEER/$\Delta P$-Q streams are registered to the device coordinate frame (FIGS. 5 and 9-10).

6.20 Run-Time QC and Safety Interlocks

During acquisition, the orchestrator monitors SNR, focus, motion/registration residuals, spectral peak sanity, and $\Delta P$-Q consistency. Photothermal safety is enforced by instantaneous limits on power at sample, dwell, and duty cycle; a temperature rise above threshold (e.g., >1° C.) triggers an automatic hold. Electrical safety gates prevent DC offsets and cap current density; hydraulic gates cap maximum $\Delta P$ and shear. On any QC or safety breach, the run enters hold/reacquire, logging the cause and corrective action without discarding the entire experiment.

6.21 Post-Run Acceptance and Provenance

Data are admitted to modeling only if acceptance gates are met (see FIG. 16; Table 10). All calibration artifacts (phantom shots, ramp traces, blank readings, power logs) are written to the run record with versions of preprocessing, encoder models, and limits in effect. Failed gates are flagged; the system can automatically request targeted reacquisitions (e.g., one OCT B-scan at a specific coordinate) to cure deficiencies.

6.22 Representative Acceptance Checklist (Exemplary)

1. Raman wavenumber: Si 520.7 cm$^{-1}$ within $\leq$+1 cm$^{-1}$; power at sample$\leq$policy limit; resolution within spec.
2. OCT/OCTA: phantom scale/registration error$\leq$preset (e.g., $\leq$10 $\mu$m); SNR above threshold; motion residuals within bounds.
3. TEER chain: blank recorded; phase/offset acceptable; measurement current density within limit; TEER reported as (R_sample-R_blank)$\times$A.
4. Hydraulics: off-cell $\Delta P$-Q ramp linear ($R^2 \geq 0.98$); $\Delta P$ hold/leak test drift$\leq$2%/5 min.
5. Thermal/medium: temperature and viscosity logged; $\Delta T$ during optical acquisitions$\leq$policy.
6. Synchronization: streams time-aligned; controller drift within spec.
7. Baseline stability: drift of TEER and Raman indices within bounds (illustratively <10% over 30 min at constant load).
8. Uncertainty coverage: prediction-vs-measurement concordance and coverage within target bands (illustratively+5%) per FIG. 10 before advancing to optimization or control.
9. Safety interlocks: optical/electrical/hydraulic gate status "armed" throughout; no excursions logged.

6.23 Relevance

This QA framework makes the platform reproducible across devices and batches, prevents artifactual conclusions (e.g., mis-registered OCT or Raman drift), and provides defensible audit trails for regulated use. By gating modeling and control on calibration and uncertainty coverage, the system links raw acquisition to the acceptance metrics (FIG. 16) and to the claim elements that require calibrated, safety-aware inference and optional closed-loop actuation.

7. Methods of Use (General)

Provide an ocular MPS with an endothelialized TM-SC interface; equilibrate at baseline ΔP and shear; acquire baseline multimodal measurements; apply a defined perturbation (mechanical or pharmacologic); continue acquisition; preprocess and fuse data; compute facility and barrier metrics; optionally adjust $\Delta P/\tau$ or dose to achieve a target state.

8. Advantages

The disclosed measurement-model framework confers five related advantages: device-agnostic analytics that standardize inputs and features rather than hardware; in-situ biochemical and structural readouts acquired under prescribed hydrodynamic load; cross-platform comparability enabled by harmonized calibration, metadata, and normalization; a feature space suited to AI-assisted prediction, uncertainty quantification, and closed-loop control; and extensibility to pharmacologic, genetic, and mechanical interventions. The subsections that follow elaborate on each advantage with exemplary operating windows and implementation details.

8.1 Device-Agnostic Analytics

The disclosed pipeline specifies inputs, calibrations, and feature transformations rather than a particular device geometry. Signals are accepted from any ocular MPS that can provide time-stamped TEER 308/impedance, ΔP-Q (pressure flow) 310, Raman spectra 314, and OCT/OCTA 312 or microscopy frames co-registered to ΔP and shear. Area normalization for TEER, viscosity-adjusted flow conversions, Raman wavenumber/power calibration, and OCT voxel scaling map raw readings into a common analytical space. Because the AI engine 110 consumes these standardized features, rather than chip-specific voltages or pixel coordinates, it generalizes across membranes, scaffolds, channel dimensions, and sensor placements without re-architecting the model. This device-agnostic design reduces revalidation burden when platforms change and supports straightforward technology transfer between labs.

8.2 In-Situ Biochemical Readouts Under Physiologic Load

Raman sampling 314 (e.g., near-IR excitation with controlled power and dwell) and OCT/OCTA 312 imaging are performed while the interface is under prescribed ΔP and shear. Acquiring biochemical and structural information in situ, rather than post-fixation, captures load-dependent states such as junctional tightening/loosening, vacuole dynamics, and ECM compaction as they occur. These label-free spectral and optical features are synchronized with TEER 308 and ΔP-Q (pressure flow) 310 so that molecular signatures can be tied directly to permeability and resistance. The result is a mechanistically coherent dataset that links pathway activity to fluidic function, enabling models that reflect causal order (challenge→molecular change→junctional remodeling→facility shift).

8.3 Cross-Platform Comparability

A harmonized metadata and normalization scheme (e.g., Raman 520.7 cm$^{-1}$ reference, TEER frequency/area reporting, viscosity/temperature logging, OCT scale verification, and geometry descriptors such as channel height and membrane porosity) allows measurements from different devices and scaffolds to be pooled or compared. The analytics expose both absolute metrics (facility, apparent permeability) and dimensionless or geometry-adjusted quantities (e.g., shear rate, hydraulic conductivity) so results can be transferred between platforms with different footprints. Acceptance checks (e.g., off-cell ΔP-Q linearity, baseline drift bounds) provide confidence that cross-site data adhere to common performance envelopes, improving reproducibility and regulatory readiness.

8.4 Suitability for AI-Assisted Prediction and Control

Because signals are synchronized and physics-informed constraints link junction integrity to permeability and resistance, the feature space is well-posed for learning. The models generate calibrated estimates of facility/permeability and forecast intraocular-pressure trajectories with explicit uncertainty sets (e.g., coverage-guaranteed bands), then use those uncertainties to recommend the smallest set of follow-up measurements expected to collapse epistemic error. The same framework supports closed-loop control of laboratory runs (e.g., dose timing, shear/ΔP profiles) under safety gates for laser power/dwell, electrode current density, and maximum ΔP. This yields faster convergence to informative experiments and transparent, auditable recommendations for therapeutic testing.

8.5 Extensibility to Multiple Interventions

The Ocular MPS system 102 evaluates pharmacologic, genetic, and mechanical strategies within a single measurement-model-decision loop. ALK-targeted attenuation, VEGFC restoration, steroid substitution/scheduling, CRISPR or vector-based constructs, and flow/pressure regimens can all be expressed as inputs, with outcomes quantified by the same multimodal readouts and normalized metrics. Because the analytics are device-agnostic and uncertainty-aware, new interventions or combinations can be added without redesigning hardware; dose, route, and timing are optimized against multi-objective criteria that include permeability restoration, safety margins, and practical constraints. This extensibility accelerates discovery while keeping results comparable across protocols and platforms.

9. Embodiments—Pharmacologic/Genetic Modulation

Embodiments include administering agents or transgenes that modulate cell-matrix interactions, cytoskeletal tension, junctional integrity, or lymphatic-like signaling at the TM-SC interface. Readouts are obtained in situ and interpreted by the unified analytics framework described above.

Note that features of the below embodiments may be combined in any order or fashion without limitation, with features from one embodiment combined with or replacing features From any Other Embodiment.

9.1 Embodiment 1 and Example 1 AI Modeling of ALK5/VEGFC from Ocular MPS Data

Without being bound by theory, an Ocular MPS system 102 reconstructs the trabecular meshwork-Schlemm's canal (TM-SC) interface 506, 508, 512, 516 and operates under controlled loading (about 0-10 mmHg pressure drop and about 0.5-5 dyn·cm$^{-2}$ shear). After conditioning to baseline stability, the Ocular MPS system 102 is challenged (e.g., corticosteroid exposure) with matched vehicle and pathway-modulator controls. Synchronized readouts include: (i) molecular assays, ALK5 activity (e.g., pSmad2/3), VEGFC transcript/protein, and junctional proteins (e.g., Claudin-5, ZO-1); (ii) label-free Raman spectra 314 sensitive to junctional/ECM composition (e.g., 785 nm, about 4-10 cm$^{-1}$ resolution, <5 mW at the sample); (iii) OCT/OCTA 312/microscopy for structural correlates (vacuole frequency, pore metrics, lumen patency); and (iv) ΔP-Q (pressure flow)

310 and TEER 308/impedance (TEER frequency about 100-10,000 Hz, area-normalized) for functional endpoints (facility, permeability). Device geometry, medium viscosity, and environmental conditions are logged as metadata, and cross-MPS normalization aligns measurements across alternative scaffolds and geometries.

A standardized pipeline denoises, calibrates, and time-aligns raw streams; feature engineering yields pathway-relevant descriptors—ALK5 and VEGFC pathway scores, Raman peak ratios, and junctional continuity/tortuosity indices—co-registered to $\Delta P$ and shear. The canal segment is represented as a physics-informed graph state-space model 304: TM and SC nodes carry latent states for ALK5 activity, VEGFC signaling, junctional integrity, and permeability, while edges encode paracrine and biomechanical coupling. Message passing propagates influence between compartments, and recurrent transitions capture the sequence from challenge→molecular change→junctional remodeling→fluidic consequence. Soft constraints link junctional integrity to permeability/resistance to maintain biological plausibility.

Training fuses Raman, OCT, omics, and flow features to predict calibrated, uncertainty-bounded changes in outflow resistance and junctional state. Model outputs include (i) estimated facility and permeability at time t; (ii) the change in facility ($\Delta$facility) over a prespecified window; and (iii) a predicted intraocular pressure (IOP) trajectory under standard physiologic assumptions, each accompanied by a coverage-guaranteed uncertainty set (e.g., a conformal prediction set). When an uncertainty-set width exceeds a predefined threshold (e.g., $>\tau\_C$ for facility), an experimental-design module proposes the minimal additional measurements, targeted Raman bands, an extra OCT time point, or a confirmatory molecular panel, expected to most effectively reduce epistemic uncertainty. In simulation/control mode, the engine evaluates steroid dose profiles, genotypes affecting ALK5/VEGFC regulation, or co-therapies (e.g., ALK5 inhibition, VEGFC supplementation, steroid substitution), forecasting junctional evolution and expected facility change; the Ocular MPS system 102 may suggest closed-loop adjustments subject to safety gates. Governance includes drift monitoring of Raman/imaging features, versioned model artifacts with full lineage, and safety guardrails (laser power/dwell, electrode current density, maximum $\Delta P$) that prevent actuation when critical sensors are missing or out of tolerance. Advantages over prior approaches: unlike AI systems that focus predominantly on fundus or OCT/OCTA image analysis detached from pathway biochemistry, this embodiment binds molecular signaling and junctional architecture to fluid-dynamic function within a physiologically controlled chip environment (see, e.g., FIGS. 1-4; Table 1-Table 3), enabling mechanism-aware predictions of junction thickness, aqueous outflow resistance, and IOP trajectories.

9.1.1 Example 1 (Prophetic)—Step-by-Step Protocol for Steroid Challenge, Acquisition, and Modeling Fabrication & conditioning. Fabricate an ocular MPS 104 that recreates the TM-SC interface 506, 508, 512, 516. Seed primary human TM and SC endothelial cells into adjacent microchannels separated by a microporous, ECM-coated interface chosen to emulate the juxtacanalicular region. Adjust seeding densities until the TM layer exhibits expected stress-fiber orientation and the SC channel shows continuous junctional staining. Perfuse at about 0.5-5 dyn·cm$^{-2}$ shear with a pressure drop of about 0-10 mmHg and equilibrate for not less than about 24 hours so that baseline permeability and pressure-flow measurements stabilize.

Challenge & controls. Initiate a corticosteroid challenge (e.g., dexamethasone) at a defined concentration and exposure interval while maintaining matched vehicle controls and, where appropriate, positive controls that perturb TGF-$\beta$ signaling. Instrument the device for concurrent multimodal acquisition throughout exposure.

Multimodal acquisition. At prespecified time points, sample TM cells for phosphorylated Smad2/3 (ALK5 activity) and SC cells for VEGFC transcript/protein and junctional proteins (e.g., ZO-1, claudins). Interrogate the same device non-invasively with Raman spectroscopy 314 (e.g., 785 nm, about 4-10 cm$^{-1}$ resolution, <5 mW at the sample) and OCT/OCTA 312/microscopy for microstructural correlates along the canal endothelium. Record trans-channel differential pressure and volumetric flow continuously to compute an outflow-resistance proxy aligned to each molecular snapshot.

Synchronization & feature engineering. Synchronize heterogeneous data to a common timeline by interpolating continuous sensor traces to the molecular sampling grid and by correcting batch effects using normalization factors derived from controls. Convert imaging into quantitative descriptors of junctional continuity, tortuosity, and thickness; reduce Raman spectra 314 to band-integrated biochemical indices; summarize phosphoprotein and gene-expression panels into pathway activity scores.

Modeling & training. Represent the canal segment as a mechanistic graph with TM and SC nodes (state variables: ALK5 activity, VEGFC signaling, junctional integrity, permeability) and edges that encode paracrine/biomechanical couplings. Unroll the graph across measurement intervals to preserve causality from steroid exposure to junctional outcome and fluidic consequence. Train a physics-informed learning engine 110 with message-passing (TM↔SC) and a recurrent transition for temporal memory. The objective penalizes deviations from experimentally measured resistance and enforces soft constraints that encode known monotone relationships between ALK5 activation, VEGFC reduction, and junctional tightening. Regularization encourages temporal smoothness and discourages biologically implausible oscillations. Train on a stratified split that withholds entire chip-level experiments for validation; apply post-training calibration for well-behaved predictive uncertainty.

Simulation & uncertainty-driven measurement. After calibration, simulate operator-specified scenarios (steroid dose profiles, patient-specific genotypes, co-therapies). Forecast junctional integrity and expected change in facility ($\Delta$facility) and translate to a predicted IOP trajectory under standard physiologic assumptions. When uncertainty bands exceed a predetermined threshold (e.g., $>\tau\_C$ for facility), propose additional, minimal measurements (e.g., targeted Raman bands, an extra OCT time point, or a confirmatory molecular panel) predicted to reduce epistemic uncertainty most efficiently.

Prospective validation & updating. Execute predicted interventions on fresh devices and replay the acquisition pipeline. If discrepancies exceed tolerance (e.g., mean absolute facility error≤about 15% over about 24 h across≥about 6 chips), localize error by ablation (preprocessing, causal structure, or constraints) and update the model under change control. Iterate the closed loop until prediction error converges to a preset acceptance criterion, yielding a validated map from exposure conditions to therapeutic recommendations (e.g., ALK5 inhibition, VEGFC supplementation, tailored steroid substitution), each annotated with predicted outflow restoration and associated uncertainty.

9.1.2 Validation, Acceptance Criteria, and Governance

Validation and acceptance criteria may include, without limitation: (i) mean absolute error for facility≤about 15% over about 24 h across≥about 6 chips; (ii) calibration metrics within predefined bounds (e.g., empirical coverage within ±5% of nominal); and (iii) stability of TEER and Raman baselines (e.g., <about 10% drift per 30 min). Governance comprises drift monitoring on spectral/vision features, versioned and auditable model artifacts with full lineage, and safety guardrails on laser power/dwell, electrode current density, and maximum ΔP. Where applicable, sequence-level information for CRISPR/gene-therapy embodiments is maintained in compliant formats and referenced in-spec without limiting the scope of this embodiment.

9.2 Embodiment 2 and Example 2—AI-Guided Genetic Modulation (ALK5/VEGFC) for Ocular MPS In this embodiment, an Ocular MPS system 102 integrates AI-driven target discovery and construct design with digital-twin simulation and on-chip validation under controlled pressure and shear. Paired multi-omics profiles from trabecular meshwork (TM) and Schlemm's canal (SC) cells, including differential expression, phosphoproteomics, and secretome, are fused to reconstruct a pathway-level portrait of the ALK5-VEGFC axis and collateral branches. A network-inference stage estimates the direction and strength of edges linking TM-restricted ALK5 activity to SC-restricted VEGFC production and junctional maintenance and ranks intervention points by expected reduction in outflow resistance within experimentally feasible bounds. The AI then performs sequence-level design: for TM-focused attenuation of ALK5 signaling (loss-of-function), it proposes CRISPR nuclease/base/prime-editing or CRISPRi strategies; for SC-focused restoration of VEGFC (gain-of-function), it proposes CRISPRa or vectorized expression (e.g., AAV) with compartment-specific promoters. Designs are scored for on-target efficiency, off-target burden, payload and promoter constraints, and immunogenic motifs.

Constructs are screened in silico using a digital twin of the canal segment: a reaction-diffusion module predicts VEGFC gradients; a junction-dynamics module maps VEGFC levels to time-dependent junctional integrity and permeability; a fluidic solver converts permeability to outflow resistance. Safety-constrained multi-objective optimization returns a Pareto-optimal shortlist for on-chip verification. Results feed back into the model under change control; drift monitors, versioned artifacts, and safety guardrails (laser power/dwell, electrode current density, maximum ΔP) govern deployment. By tying sequence design to chip-level functional rescue, this embodiment enables rapid, reproducible advancement of gene and cell therapies targeting steroid-induced ALK5/VEGFC dysregulation.

9.2.2 Example 2—Exemplary Methodology (Prophetic; Non-Limiting)

Overview. Paired multi-omics profiles are acquired from TM and SC cells harvested from ocular MPS 104 devices exposed to clinically relevant steroid regimens and matched controls. Omics matrices are normalized, aligned to pressure/shear timelines, and integrated to reconstruct the ALK5-VEGFC network. Candidate nodes/edges are prioritized by the modeled reduction in outflow resistance achievable within about feasible perturbation limits.

Construct design. For TM (ALK5 attenuation), guide RNAs are generated for CRISPR nuclease, base editing, or prime editing based on locus accessibility, predicted repair outcomes, and the need for durable vs. transient modulation. For SC (VEGFC restoration), expression cassettes are assembled with compartment-specific promoters and regulatory elements in a vector suitable for anterior-chamber delivery under ocular payload constraints. Each candidate is scored in silico for off-target potential and immunogenic motifs using models tuned on ocular datasets.

Digital-twin screening. Each design is evaluated in a physics-informed digital twin: (i) reaction-diffusion predicts VEGFC gradients for a given expression/turnover; (ii) junction-dynamics maps VEGFC levels to time-dependent junctional continuity and effective permeability; (iii) a fluidic solver converts permeability to outflow resistance. Safety-constrained optimization yields a shortlist for wet-lab testing.

On-chip delivery and readouts. Shortlisted constructs are synthesized and delivered to TM or SC compartments under conditions that segregate transduction (to preserve causal attribution). Editing/expression is verified by targeted sequencing and quantitative protein assays. Functional rescue is quantified via the same junctional imaging and Raman indices used in modeling, plus continuous pressure-flow and TEER/impedance measurements, under the same hydrodynamic windows disclosed elsewhere.

Model update and iteration. If observed rescue or safety deviates from simulation beyond tolerance, the discrepancy is attributed (e.g., promoter strength, nuclear access, pathway compensation), parameter posteriors in the digital twin are updated, and the optimizer proposes revised constructs that address the diagnosed failure while preserving prior gains.

Acceptance criteria and governance (illustrative). Constructs advance when they achieve about predefined responder criteria (e.g., permeability recovery and resistance reduction over a durability window reflecting clinical steroid courses), maintain empirical uncertainty coverage within about ±5% of nominal, and pass safety gates (laser power/dwell, electrode current density, maximum ΔP). Each candidate is archived with a design dossier (sequence, simulation↔experiment concordance, predicted ocular distribution, risk register). Where sequence listings are applicable, compliant formats are maintained and cross-referenced.

9.3 Embodiment 3—AI-Enhanced Pharmaceutical Optimization for ALK5/VEGFC Modulation (Ocular MPS)

In this embodiment, the Ocular MPS system 102 operationalizes the modeling framework into a closed-loop pharmaceutical pipeline that discovers, optimizes, and deploys pharmacologic interventions to counteract steroid-induced dysregulation of the ALK5-VEGFC axis. Therapeutic hypotheses are grounded in the mechanism: attenuate ALK5 signaling within trabecular meshwork (TM), restore VEGFC signaling within Schlemm's canal (SC), and minimize steroid-induced junction tightening without compromising anti-inflammatory objectives.

A computational triage stage profiles curated libraries, ALK5 inhibitors, VEGFC biologics/mimetics, and repurposing sets of FDA-approved small molecules, using QSAR, target-class filters, and docking surrogates calibrated on ocular datasets. Generative chemistry proposes structural analogs around promising chemotypes and applies liability filters (photoreactivity, aggregation propensity, nonspecific membrane effects).

Candidates advance to standardized ocular MPS triad assays (steroid-challenged devices, matched vehicle, pathway positive controls) operated under the same shear/ΔP and baseline-stability windows used elsewhere (see, e.g., FIGS. 1-6; Table 1-Table 3). During challenge-treat cycles, permeability and outflow resistance are recorded continuously, while molecular markers (ALK5 activity, VEGFC levels, junction integrity) are sampled at scheduled time points. Datasets are normalized to control traces and transformed into a common feature representation (junctional continuity indices, Raman-derived biochemical ratios, phosphoprotein pathway scores).

In parallel, an ocular PK/PD model (including, without limitation, cornea, anterior chamber, TM, and SC compartments) links dose/route/formulation to intraocular exposure profiles and to expected shifts in pathway activity and permeability learned from the chip assays. This supports rational regimen design across topical, intracameral, and sustained-release strategies. When co-administration with anti-inflammatory steroids is needed, an optimizer evaluates synchronous vs. staggered schedules to separate anti-inflammatory benefit from ALK5-VEGFC penalties.

Regimen search, uncertainty gating, and dosing/route selection follow the Bayesian optimization and contextual-bandit framework described elsewhere, yielding a candidate regimen with calibrated confidence and a corresponding monitoring plan. Prospective validation executes the full schedule on-chip; discrepancies are localized to exposure (PK) or mechanism (PD) and used to update both the PK/PD link and the mechanistic model under change control. Safety gates (cell viability, unintended barrier disruption, innate immune activation, off-target signaling) are enforced throughout. Regimens meeting responder criteria (predefined thresholds for permeability recovery, resistance reduction, and safety margins) are compiled into a dossier with critical quality attributes, acceptable material ranges, risk registers, and next-step recommendations (scale-up or in vivo confirmation). The system also supports drug repurposing by periodically rescoring repurposing libraries through the chip-model linkage.

9.4 Embodiment 4: Analysis of Endothelial Junctions: AI-Enhanced Pathology, Steroid Effect, Pharmaceutical Modulation, and Age In this embodiment, the Ocular MPS system 102 provides an AI-enhanced methodology dedicated to quantitative analysis of endothelial junctions within Schlemm's canal and their coupling to trabecular meshwork signaling. The method starts by establishing a stable co-culture on the eye-on-a-chip and acquiring high-content images of the canal endothelium under baseline conditions using fluorescence markers of tight and adherens junctions together with label-free Raman spectra obtained at the same coordinates. The imaging stack 506, 508, 512, 516 is registered to the device coordinate system so that every field of view is indexed to a known shear and pressure microenvironment and is paired with simultaneous pressure-flow traces.

Raw frames are corrected for illumination and motion, then passed to a segmentation engine that has been pretrained on canal endothelium and adapted with a small number of chip-specific annotations. The engine yields continuous maps of junctional continuity and thickness rather than binary traces; where signal-to-noise is limited, a super-resolution reconstruction trained on matched confocal stacks restores sub-pixel detail without introducing hallucinated structures because physical priors penalize discontinuities that would be incompatible with membrane mechanics.

With reliable maps in hand, the Ocular MPS system 102 computes a suite of interpretable, physics-anchored descriptors in continuous time. Junctional continuity is expressed as a pathwise integral normalized to perimeter, thickness is summarized by the median belt width and its spatial variance across a canal segment, and tortuosity is estimated from curvature distributions that penalize kinks consistent with pathological stiffening.

These image-derived descriptors are cross-checked against Raman band ratios associated with protein crosslinking and lipid order, and against instantaneous outflow resistance computed from the pressure-flow signal. A temporal filter converts these instantaneous values to trajectories with well-defined rise times and relaxation half-times. The trajectories form the basis of a junctional state space in which normal physiology occupies a compact region characterized by high continuity, moderate thickness, low tortuosity and rapid relaxation, whereas pathology and steroid-induced tightening move the system toward thicker, more tortuous, slowly relaxing junctions.

9.4.1 Pharmacological Modulation

Pharmaceutical effects are evaluated by introducing candidate modulators, such as ALK5 inhibitors, VEGFC supplementation vectors, or repurposed small molecules, at specific points along the steroid course. The AI estimates an immediate looseness increment and a sustained conductivity gain by comparing post-treatment trajectories to their pre-treatment extrapolation and to a learned age-matched normal manifold. Because pharmacological responses often show hysteresis, the model distinguishes elastic recovery from plastic remodeling by fitting two-timescale relaxation kernels; the relative weights yield a reversibility score that predicts whether repeated dosing will restore a physiological junctional state or whether compensatory pathways are likely to blunt the benefit. When compensatory signatures are detected, for example, Raman patterns consistent with excess extracellular matrix deposition, the optimizer proposes a co-therapy sequence that staggers steroid peaks away from windows of heightened junctional vulnerability while preserving anti-inflammatory action.

Modulation is not restricted to biochemistry. The orchestration service can alter shear waveforms and cyclic stretch within safe bounds to probe mechanotransductive flexibility. The AI records how junctional descriptors react to these controlled mechanical perturbations and infers a mechanosensitivity profile that, together with biochemical responses, classifies the canal endothelium into phenotypes with distinct therapeutic routes. A phenotype with preserved mechanosensitivity but impaired VEGFC signaling, for instance, shows rapid improvement under VEGFC supplementation, whereas a phenotype with flattened mechanosensitivity benefits more from ALK5 inhibition and ROCK-pathway-sparing steroid substitution. The classification is learned from chip-level evidence and remains interpretable because it is defined by measured descriptors and actuated perturbations rather than latent embeddings alone.

9.4.2 Steroid Effect

The steroid effect is elicited by perfusing dexamethasone according to a defined exposure profile. The AI monitors junctional texture in real time and detects sub-visual precursors of tightening, including band-limited fluctuations that precede macroscopic belt thickening. A causal encoder links contemporaneous increases in trabecular meshwork ALK5 activity to subsequent declines in canal VEGFC signal and to the observed junctional drift in state space, quantifying the delay between upstream signaling and endothelial response. From the detected drift, the model forecasts the magnitude and timing of outflow resistance elevation and, where predictions cross a predefined risk boundary, the Ocular MPS system 102 proposes early countermeasures that can be executed on the same device or translated into a clinical regimen.

9.4.3 Age Effect

Age is treated as both a biological covariate and a source of domain shift. Donor age metadata and in-chip models of accelerated senescence establish age-conditioned baselines for the junctional descriptors and Raman indices; hierarchical models then borrow strength across age strata to produce robust estimates even when individual strata are sparsely sampled. During inference, conditional normalization removes age-expected drift so that the remaining deviation reflects true pathology or drug effect rather than normative aging. The survival layer links age-adjusted junctional states to time-to-event predictions for intraocular pressure rise, while the mixed-effects layer separates donor-level variation from treatment effects to avoid confounding. In practice this means a canal endothelium from an older donor is not penalized for naturally thicker belts so long as its continuity, tortuosity and relaxation kinetics fall within the age-conditioned normal range; by contrast, steroid-treated chips that deviate from this range are flagged early even when absolute thickness has not yet surpassed a fixed threshold.

9.5 Embodiment 5: Post-Implant Endothelial Junction Testing and Analysis (Clinical Mode)

This embodiment translates the chip-learned junction mechanics into a clinical, post-implant analytics pipeline for eyes receiving an endothelial-integrated Schlemm's canal stent. The analysis begins at a defined pre- or immediate postoperative baseline in which structural OCT and OCT angiography of the implanted segment are acquired under standardized scan geometry and fixation. The structural stack is registered to the canal circumference and collector channel ostia, and a lumen-aware segmentation reconstructs the inner wall surface in cylindrical coordinates so that junction-level descriptors can be inferred from macroscopic signals. From these registered volumes the Ocular MPS system 102 extracts canal-lining continuity, a belt-thickness proxy derived from reflectivity and edge spread at the inner wall, and a curvature-based tortuosity profile along the stent-endothelium interface. The OCTA stack is co-registered and reduced to motion-contrast amplitude, pulsatility indices synchronized to the cardiac cycle, and a segmental perfusion map that quantifies flow asymmetry and stagnation along the implanted arc.

These imaging-derived descriptors are mapped into the junctional state space learned on the chip using a clinical transfer model that was pre-trained on paired chip descriptors and simulated clinical features, then adapted to clinical data using a small set of high-quality OCT/OCTA exemplars. The mapping preserves the mechanistic axes of continuity, thickness, tortuosity, relaxation kinetics, and their coupling to predicted outflow resistance so that the clinical state can be compared directly to the age-conditioned normal manifold defined in the research embodiments. The model produces a calibrated prognosis of resistance drift and a time-to-event estimate for clinically meaningful intraocular pressure rise, accompanied by an uncertainty band; if uncertainty exceeds a threshold, the Ocular MPS system 102 recommends a minimal measurement set predicted to collapse epistemic uncertainty most efficiently, such as a repeat OCTA with extended dwell around regions of suspected stagnation.

Steroid co-therapy and pharmaceutical modulation are handled by explicitly conditioning prognosis on exposure schedules and by forecasting counterfactual trajectories under feasible regimen adjustments. Where postoperative steroids are likely to tighten junctions, the Ocular MPS system 102 simulates substitution or taper windows and, when a drug-eluting stent or reservoir is present, proposes elution timing that maximizes predicted junction loosening while respecting ocular tolerability. The same clinical pipeline detects early endothelial compromise, including hyper-reflective deposits, thinning, multilayer domes, vacuole changes, and bridging patterns, and separates elastic recovery from plastic remodeling by fitting two-timescale relaxation kernels to serial scans; the resulting reversibility score guides whether continued observation, pharmaceutical adjustment, or interventional revision is indicated. Age is incorporated as a biological covariate via hierarchical models that establish age-conditioned baselines for all descriptors; conditional normalization removes expected aging drift so that alerts reflect true pathology or drug effect rather than normative changes.

Closed-loop operation is identical in structure to the laboratory embodiments but uses clinical inputs and outputs. Each new visit updates the posterior over patient-specific response parameters; recommendations are uncertainty-gated and accompanied by local explanations that identify the image regions and flow segments most responsible for the forecast and by counterfactuals that specify the minimal change in steroid timing, elution window, or follow-up cadence required to return the junctional state to the age-appropriate normal region. Safety guardrails prevent action if scans fail quality checks or if segmentation confidence falls below threshold; in such cases the Ocular MPS system 102 requests repeat imaging rather than issuing therapy guidance. By anchoring clinical analytics to the same junction-mechanics state space used in the chip, this embodiment provides a reproducible, mechanism-aware method for post-implant surveillance and therapy steering without requiring invasive sampling.

In eyes fitted with the commonly owned Schlemm's-canal endothelial-integrated stent, this clinical mode treats the implant as a standardized anatomic scaffold and a controllable actuator. The OCT/OCTA volumes are additionally registered to the stent's arc length and micropore lattice so that junction-descriptor trajectories can be computed along stent subsectors and mapped to predicted outflow contribution by sector. The decision engine then translates the age-conditioned junctional state into concrete control schedules for the implant, such as timing and duty cycle of drug-elution phases or adjustment of micro-valve or reservoir settings where present, and coordinates those actions with systemic or topical steroid tapering to avoid overlap with windows of heightened junctional vulnerability. Manufacturing specifications and in-clinic quality metrics for the implant, including micropore density and endothelial coverage, can be propagated into the model as priors so that post-implant forecasts respect device-specific constraints. The linkage preserves claim independence: the stent remains the environment and actuator, while novelty resides in the mechanism-aware analytics and control that steer post-implant care.

9.6 Embodiment 6—AI-Guided CRISPR and Gene-Therapy Optimization in Steroid-Perturbed Pathways In another embodiment, the Ocular MPS system 102 provides an AI-assisted pipeline that designs and validates genetic modulation strategies targeting the ALK5/TGFβ and VEGFC/VEGFR3/PROX1 axes within trabecular meshwork (TM) and Schlemm's canal (SC) cells using an Ocular MPS system 102. Without being bound by theory, corticosteroid exposure can increase ALK5-mediated signaling and promote junctional tightening in the TM-SC interface, while VEGFC activity supports junctional patency and lymphatic-like endothelial features in SC. The disclosed pipeline closes the loop between in silico design, digital-twin simulation, and chip-level validation under controlled pressure and shear.

9.6.1 Target Identification and Prioritization

The AI engine 110 mines transcriptomic and proteomic datasets acquired from steroid-exposed TM and SC cells in the ocular MPS 104, supplemented by baseline controls and pathway-modulator arms. It ranks candidate genetic levers that contribute to junctional tightening beyond VEGFC itself, including secondary VEGF receptors, TGF-β co-receptors, cytoskeletal regulators, and junctional scaffolds, by combining differential expression/effect sizes with causal-graph attribution. For each target, the Ocular MPS system 102 classifies the desired direction of modulation (loss-vs. gain-of-function) and links it to measurable functional endpoints (facility, permeability).

9.6.2 Construct and Guide Design

For loss-of-function in TM (e.g., dampening ALK5 signaling), the engine proposes CRISPR/Cas edits (e.g., Cas9/Cas12a) or CRISPRi constructs; for gain-of-function in SC (e.g., enhancing VEGFC), it proposes CRISPRa or vectorized expression (e.g., AAV-based) with tissue-appropriate promoters. A reinforcement-learning generator and multi-objective scorer jointly optimize guide RNAs (on-target efficiency, predicted off-targets, PAM constraints, GC content, edit context) and vector designs (capsid tropism for TM vs. SC, payload constraints, promoter strength, expression kinetics). Designs are rejected if predicted off-target burden, immunogenicity surrogates, or delivery constraints exceed predefined thresholds.

9.6.3 in Silico Ocular-MPS Validation

Proposed edits/vectors are passed to a physics-informed digital twin of the canal segment that couples molecular pathway states to junctional integrity and fluid dynamics. The simulator forecasts how a construct will reshape VEGFC gradients, ALK5 activity, and junctional loosening/tightening over time under specified pressure and shear, then translates those effects into predicted facility changes and intraocular pressure (IOP) trajectories. Virtual screening triages candidates and identifies the minimal wet-lab experiment set most likely to reduce uncertainty.

9.6.4 Closed-Loop Experimental Validation

Prioritized constructs are executed on fresh ocular MPS 104 chips with matched controls. The platform acquires synchronized readouts, molecular panels (e.g., pSmad2/3, VEGFC expression, junctional proteins), Raman spectral fingerprints 314, OCT/OCTA 312/microscopy for structural correlates, and ΔP-Q (pressure flow) 310/TEER 308 for functional endpoints, under the same hydrodynamic windows used elsewhere in the specification. Results are fed back to the AI; if a construct partially restores permeability but triggers off-target stress signatures, the Ocular MPS system 102 automatically proposes revised guides/vectors and updates its priors under change control.

Optimization, governance, and safety. Multi-objective optimization balances on-target rescue (facility/permeability restoration) against off-target risk, vector constraints, and assay safety gates (laser power/dwell, electrode current density, maximum ΔP). Drift monitors watch Raman/imaging feature distributions; exceeding tolerance triggers recalibration or retraining. Every iteration yields a versioned model artifact and construct design with full lineage from raw data through preprocessing and hyperparameters, enabling auditability and rollback. Sequence information (when present) is managed in compliant formats and linked to in-spec references.

9.6.5 Enablement and Distinction

This embodiment establishes a reproducible AI-driven feedback loop, from target discovery to construct design, digital-twin screening, and chip-level validation in a physiologic context, explicitly tuned to steroid-perturbed ALK5/VEGFC pathways.

The embodiment culminates in a calibrated, uncertainty-aware report that integrates pathology assessment, steroid-induced risk, observed pharmaceutical modulation and age conditioning. The report includes a predicted resistance trajectory with confidence bands, a reversibility and mechanosensitivity profile, and a proposed intervention plan selected by the optimization engine, all cross-referenced to the measurements that most influenced the decision and accompanied by counterfactual statements that describe the minimum changes in dose, timing or mechanical environment required to return the junctional state to the age-appropriate normal manifold. The same report format is produced for clinical use with OCT-derived canal metrics substituted where necessary, preserving the mechanistic link by mapping clinical features into the chip-learned junctional state space.

9.7 Embodiment 7-ALK Signaling Modulation (ALK1/ALK5)

In this embodiment, signaling through Activin receptor-like kinases (ALKs), including ALK1/ACVRL1 and ALK5/TGFβR1 (alone or in combination), is modulated at the TM-SC interface by pharmacologic, biologic, nucleic-acid, or mechanical inputs. Effects are quantified in situ under defined hydrodynamic load (e.g., $\Delta P \approx 0$-10 mmHg; shear$\approx 0.5$-5 dyn·cm$^{-2}$) using ΔP-Q facility 310, TEER 308/permeability, morphology, and Raman-derived biochemical features 314, as standardized in the Methodology. (Illustrative and non-limiting.)

In certain embodiments, signaling through Activin receptor-like kinases ("ALKs") is modulated at the trabecular meshwork-Schlemm's canal (TM-SC) interface. "ALKs" includes, without limitation, ALK1/ACVRL1 and ALK5/TGFβR1, alone or in combination, and functional analogs or downstream effectors. Modulation may be achieved by small molecules, biologics, nucleic acids, or mechanical cues. Effects are quantified under prescribed loading conditions—about 0-10 mmHg pressure drop and about 0.5-5 dyn·cm$^{-2}$ shear-using pressure-flow (ΔP-Q) facility, TEER/permeability, morphological descriptors, and Raman-derived biochemical features.

Without limiting to any mechanism, ALK5/TGFβR1 activity in TM generally promotes cytoskeletal reinforcement and ECM deposition via SMAD2/3 and RhoA/ROCK branches, which tightens the interface and elevates hydraulic resistance. In contrast, endothelial ALK1/ACVRL1 signaling is associated with shear-responsive endothelial programs and, when balanced against ALK5, may support junctional configurations compatible with fluid entry on the SC side. Because both axes are load-sensitive, modulation is performed while the device is under defined ΔP and shear so that biochemical state, junctional architecture, and fluidic function are measured in situ and co-registered.

9.7.1 Exemplary Inputs and Controls

Modulators may include ALK5-pathway attenuators (e.g., small-molecule type-I receptor inhibitors or ligand traps), ALK1 agonists or biased ligands, nucleic acids that reduce or enhance expression of ALK1/ALK5 or their immediate transducers (e.g., SMAD2/3, SMAD1/5/8), and mechanical cues such as shear waveforms that bias ALK1-favored endothelial responses. Steroid challenge (e.g., dexamethasone) may be applied to reveal differential rescue, with matched vehicle and pathway-positive controls to anchor effect sizes. Dose and exposure intervals are chosen to remain within ocular tolerability and device limits; in non-limiting examples, perfusate concentrations span low-nano-molar to micromolar for small molecules, picomolar to nanomolar for biologics, and 10-100 nM for siRNA or ASO delivery to the targeted compartment.

9.7.2 Readouts and Timing

TM-side ALK5 engagement is indexed by pSMAD2/3 immunoreactivity, cytoskeletal stress-fiber metrics, and Raman bands sensitive to protein and matrix composition; SC-side responses are assessed by markers of endothelial identity and junctional patterning, including VE-cadherin/ZO-1 distribution, vacuole/pore dynamics, and, where relevant, pSMAD1/5/8 as an ALK1-biased readout. OCT/OCTA 312 or microscopy provides structural correlates (e.g., vacuole frequency, pore size distributions, membrane deformation), while TEER 308 ($\Omega \cdot cm^2$), apparent permeability (P__app_, $cm \cdot s^{-1}$), and facility (C=Q/Δ_P_) quantify functional consequence. Measurements are acquired at baseline, during modulation, and post-washout to estimate onset, magnitude, and durability of effect under the same ΔP-Q and shear windows.

9.7.3 Normalization and Comparability

To support cross-platform analyses, TEER 308 is area-normalized and reported with electrode placement and frequency; ΔP-Q 310 linearity is verified off-cell (e.g., $r^2 \geq 0.98$) with viscosity entered for the current lot; Raman 314 is calibrated to the 520.7 $cm^{-1}$ silicon reference with laser power/dwell within preset limits; and OCT 312 scale is confirmed against a micrometer target. Geometry descriptors (channel height h, width w, length L, membrane porosity, and thickness) are logged so shear rate ($\approx 6 \cdot Q\_/wh^2$ under a parallel-plate approximation) and hydraulic conductivity (L_p_=Q/AAP) can be reported alongside raw facility.

9.7.4 Illustrative Operating Sequence

After baseline stabilization under about 2-6 mmHg ΔP and about 0.5-5 $dyn \cdot cm^{-2}$ shear, a first modulation phase attenuates ALK5 (TM-targeted) and/or activates ALK1 (SC-targeted). Molecular, structural, and fluidic signals are recorded continuously or at scheduled intervals (e.g., 5-30 min) with washouts between conditions to assess reversibility. A second phase explores schedule effects, for example, sequencing ALK5 attenuation before or after steroid pulses, or staggering ALK1-biased stimuli relative to shear peaks, to separate anti-inflammatory objectives from junction-tightening penalties. Safety gates (maximum ΔP, shear, laser power/dwell, and electrode current density) prevent actuation when sensors are out of tolerance; baseline drift bounds (e.g., <about 10% over about 30 min) are enforced before accepting runs.

9.7.5 Analysis and Decision Rules

Physics-informed analytics link junctional integrity to permeability and resistance, yielding calibrated estimates of Δfacility over a prespecified window and associated uncertainty sets (e.g., coverage-guaranteed bands). Where uncertainty exceeds thresholds, the Ocular MPS system 102 proposes additional measurements, such as targeted Raman bands or an extra OCT time point, to resolve ambiguity efficiently. Effect sizes are summarized as change from baseline (e.g., percent increase in facility or decrease in TEER), along with responder rates and durability over an interval that mirrors clinically relevant steroid courses.

9.7.6 Outcomes and Uses

Successful ALK-axis modulation induces a measurable increase in permeability/facility and a corresponding reduction in resistance under matched load, with corroborating molecular and structural signatures (e.g., reduced pSMAD2/3 and stress-fiber prevalence on the TM side; stabilized junctional patency and vacuolation on the SC side). Because the framework is device-agnostic and load-aware, results are comparable across alternative scaffolds, membranes, and geometries and can be extended to combination strategies, including ALK5 attenuation with VEGFC supplementation, route and dose scheduling, and co-therapies that preserve anti-inflammatory benefit while avoiding undue junction tightening.

All parameter ranges, materials, and component placements in this embodiment are illustrative and non-limiting. Functionally equivalent modulators, delivery methods, schedules, and operating windows fall within the scope of this document.

9.8 Embodiment 8—AI Modeling of ALK5/VEGFC Molecular Signaling with an Ocular MPS In this embodiment, an Ocular MPS system 102 that recapitulates the trabecular meshwork-Schlemm's canal (TM-SC) interface, using primary TM cells 508 and SC endothelial cells 514 separated by a porous membrane 512 and operated under defined hydrodynamic load, serves as the data source for AI modeling of ALK5/VEGFC signaling. Ccorticosteroid exposure (e.g., dexamethasone) can elevate TM ALK5/TGFβR1 pathway activity, as indexed by phosphorylated SMAD2/3 and related markers, while Schlemm's canal endothelium 514 can exhibit reduced VEGFC output and increased junctional protein density (e.g., occludins, claudins, ZO-1), findings consistent with heightened barrier resistance.

The Ocular MPS system 102 acquires synchronized, multimodal readouts in situ under load: molecular assays quantifying ALK5/VEGFC pathway state and junctional proteins; label-free Raman spectra 314 sensitive to junctional and extracellular-matrix composition (e.g., 785 nm excitation, ~4-10 $cm^{-1}$ spectral resolution, ≤5 mW at the sample); OCT/OCTA 312 and/or microscopy for structural correlates such as vacuole frequency, pore metrics, and lumen patency; and ΔP-Q (pressure flow) 310 plus TEER 308/impedance for functional endpoints (facility, permeability). Device geometry, medium viscosity/temperature, and environmental conditions are logged as metadata, and cross-MPS normalization aligns measurements across alternative scaffolds and geometries. For how these measurement streams map to AI engines and outputs, see Table 3.

9.8.1 Calibration and Safety Limits

Prior to challenge, calibration and safety gates are verified to ensure cross-platform comparability and regulatory readiness. TEER 308 is area-normalized and reported with electrode placement and frequency (e.g., ~100-10,000 Hz), with acellular blanks recorded. Off-cell ΔP-Q (pressure flow) 310 linearity is confirmed (e.g., $r^2 \geq 0.98$) with viscosity at 37° C. entered; Raman 314 is referenced to the 520.7 $cm^{-1}$ silicon peak with laser power and dwell constrained within preset limits; and OCT scale/focus are checked against a micrometer target with scan geometry (B-scan orientation and step size) logged. Safety gates define maximum ΔP, shear, laser power/dwell, and electrode current density; runs are held if baseline drift of TEER or Raman exceeds illustrative bounds (e.g., <~10% over ~30 min).

9.8.2 Feature Engineering, Normalization, and Derived Quantities

Heterogeneous inputs are denoised, calibrated, and time-aligned to yield pathway-relevant features co-registered to load. Feature engineering produces ALK5 and VEGFC activity scores from phospho-protein and transcript/protein panels; Raman band ratios and band-integrated biochemical indices; and image-derived junctional continuity/tortuosity and vacuole/pore descriptors aligned to ΔP and shear. Facility and permeability are computed by canonical relations (e.g., facility $C=Q/\Delta P$ $PC=Q/\backslash Delta$ $PC=Q/\Delta P$; hydraulic conductivity $Lp=Q/(A\cdot\Delta P)$ $L\_p=Q/(A\backslash cdot\backslash Delta$ $P)Lp=Q/(A\cdot\Delta P)$); TEER is reported as TEER=(Rsample-Rblank)·A\mathrm $\{TEER\}=(R\_\{\backslash text \{sample\}\}-R\_\{\backslash text \{blank\}\})$ \cdot ATEER=(Rsample–Rblank)·A. Batch effects are corrected (e.g., ComBat or domain-adaptation approaches), and geometry descriptors (channel width www, height hhh, length LLL; membrane thickness and porosity) are logged so that dimensionless or geometry-adjusted quantities (e.g., shear rate≈6 $Q/(wh2)\backslash approx$ 6 $Q/(wh^2)\approx 6$ $Q/(wh2)$ under the parallel-plate approximation; hydraulic conductivity) can be compared across devices. Engine selection for baseline facility/permeability, image/OCT feature extraction, and Raman biochemical indexing follows Table 3.

9.8.3 Model Architecture and Outputs

AI modeling is performed with a physics-informed graph state-space model 304 implementable as a graph neural network with recurrent transitions. TM and SC compartments are represented as nodes whose latent states include ALK5 activity, VEGFC signaling, junctional integrity, and permeability; edges encode paracrine and biomechanical coupling. Message passing propagates influence between compartments, while the recurrent dynamics capture time-ordering from steroid challenge to molecular change to junctional remodeling to fluidic consequence. Soft constraints encode known monotone relationships linking junctional integrity to permeability and resistance, improving biological plausibility and convergence in small-sample regimes. Trained on Raman/OCT/omics/flow features, the model outputs (i) estimated facility and permeability at time ttt; (ii) the change in facility (Δfacility) over a prespecified window; and (iii) a predicted intraocular-pressure (IOP) trajectory under standard physiologic assumptions, each accompanied by calibrated uncertainty sets (e.g., coverage-guaranteed conformal prediction). This corresponds to the "Junctional remodeling under steroid challenge" and "Pathway attribution (ALKS vs, VEGFC balance)" rows in Table 3.

9.8.4 Uncertainty-Gated Experimental Design and Simulation

Uncertainty is used to drive efficient data acquisition and control. When the coverage-guaranteed uncertainty set for a target (e.g., Δfacility over the window of interest) exceeds a predefined threshold, the engine proposes the minimal additional measurements predicted to reduce epistemic uncertainty most efficiently, for example, a targeted Raman band, an extra OCT time point, or a confirmatory molecular panel. The same model can simulate steroid dose profiles, genotypes affecting ALK5/VEGFC regulation, or co-therapies (e.g., ALK5 attenuation, VEGFC restoration) and, where implemented, recommend closed-loop adjustments subject to safety gates. In representative use, a VEGFC polymorphism associated with reduced expression is simulated to forecast accelerated junctional tightening under a standard dexamethasone regimen, prompting earlier prophylactic or counter-regulatory intervention. Active experiment design and measurement menus follow the "Active experiment design to reduce uncertainty" entry in Table 3.

9.8.5 Prospective Validation and Acceptance Criteria

Predicted interventions are executed on fresh chips under matched load and schedule; acceptance criteria include, by way of example, mean absolute facility error≤15% over 24 h across ≥6 chips. Uncertainty thresholds and decision logic are harmonized with Table 3. Deviations beyond tolerance trigger ablation to localize error to preprocessing, causal structure, or constraint layers and are followed by change-controlled updates with full lineage from raw observations through preprocessing, hyperparameters, and validation. Drift monitors track Raman and imaging feature distributions; triggers initiate incremental retraining under configuration control. Each released model is uniquely versioned to enable auditability and rollback.

9.8.6 Cross-Platform Comparability, Explainability, and Governance

Cross-MPS comparability is maintained through harmonized calibration, geometry-aware normalization, and explicit reporting of operating windows and metadata. Each recommendation is accompanied by local feature attributions and counterfactuals (what measurement change would reverse an unfavorable prediction). Versioned model artifacts, audit trails, and drift monitoring of core feature distributions support transparency, safety, and regulatory readiness.

All materials, parameter ranges, and component placements in this embodiment are illustrative and non-limiting. Functionally equivalent devices, sensors, and operating windows fall within scope, provided that inputs are time-stamped, normalized, and co-registered to ΔP and shear to support the disclosed AI modeling.

9.9 Embodiment 9—Modulation of the VEGF-C/VEGFR3/PROX1 Axis at the TM-SC Interface In this embodiment, lymphatic-like signaling associated with Schlemm's canal (SC) endothelial identity is modulated at the trabecular meshwork-Schlemm's canal (TM-SC) interface while the Ocular MPS system 102 operates under defined hydrodynamic load. Activation of VEGF-C/VEGFR3 (FLT4), with neuropilin-2 (NRP2) as an optional co-receptor, promotes a PROX1-linked endothelial program that supports junctional patency, vacuole/pore formation, and effective trans-interface fluid entry. In contrast to ALK5-biased tightening on the TM side, engagement of this axis tends to reduce hydraulic resistance. Because these behaviors are load-responsive, all interventions and measurements are performed in situ under prescribed pressure drop (ΔP) and shear so that biochemical state, junctional architecture, and fluidic function are co-registered.

9.9.1 Calibration and Safety Limits

Before challenge, calibration and safety gates are verified to ensure cross-platform comparability. TEER 308 is area-normalized and reported with electrode placement and measurement frequency (e.g., ~100-10,000 Hz), with acellular blanks recorded. Off-cell ΔP-Q (pressure flow) 310 linearity is confirmed (e.g., $r^2 \geq 0.98$) with viscosity entered at 37° C.; Raman 314 is referenced to the 520.7 $cm^{-1}$ silicon peak with laser power and dwell constrained within preset limits; OCT scale/focus is checked against a micrometer target with scan geometry logged. Safety gates define maximum ΔP, shear, laser power/dwell, and electrode current density; runs are held if baseline drift of TEER or Raman exceeds illustrative bounds (e.g., <~10% over ~30 min).

9.9.2 Modulators and Dosing Schedules

After establishing baseline stability (illustratively ΔP≈2-6 mmHg; wall shear≈0.5-5 $dyn\cdot cm^{-2}$), VEGF-C pathway modulation is applied. Non-limiting examples include recombinant VEGF-C or functionally equivalent agonists (activated/"mature" forms where potency is required), small molecules or biologics that enhance VEGFR3 signaling or PROX1 expression, and nucleic acids (mRNA, viral vectors, CRISPRa) that up-regulate VEGFC in SC endothelium. Antagonists or knockdown reagents (anti-VEGFR3, NRP2 blockade, siRNA/ASO) can be used to map causal directionality and dynamic range. Dose and timing are selected within ocular tolerability and device limits; ligand equivalents typically span low-picomolar to low-nanomolar at the cell surface with exposure intervals of minutes to hours. Schedules may include pre-treatment, co-treatment with steroids, or post-challenge rescue.

9.9.3 Multimodal Readouts and Derived Quantities

Molecular assays quantify VEGF-C/VEGFR3/PROX1 pathway state and junctional proteins (e.g., VE-cadherin, ZO-1), together with downstream AKT/ERK and eNOS activation. OCT/OCTA 312 and/or microscopy provide structural correlates (vacuole frequency, pore metrics, SC lumen patency, membrane deformation). Label-free Raman 314 spectroscopy captures junctional/ECM biochemical signatures under the same $\Delta$P and shear. $\Delta$P-Q (pressure flow) 310 with TEER 308/impedance yields facility and permeability endpoints. Derived quantities include facility ($C=Q/\Delta P$), hydraulic conductivity ($Lp=Q/(A\cdot\Delta P)$), and TEER (($R\_sample-R\_blank)\cdot A$). Geometry (channel w, h, L; membrane thickness/porosity) and media viscosity/temperature are logged to enable shear-rate normalization ($\approx 6$ $Q/(w\cdot h^2)$ under a parallel-plate approximation) and cross-device comparison.

9.9.4 Feature Engineering, Normalization, and Comparability

Heterogeneous inputs are denoised, calibrated, and time-aligned to yield pathway-relevant features co-registered to load. Features include VEGFR3 activity and PROX1 expression indices; Raman band-integrated biochemical measures; and junctional continuity/tortuosity and vacuole descriptors aligned to $\Delta$P and shear. Batch effects are corrected (e.g., ComBat or domain-adaptation approaches), and acceptance checks (e.g., off-cell $\Delta$P–Q $r^2\geq 0.98$) support pooled analyses across scaffolds and geometries.

9.9.5 Model Architecture and Outputs

Time-courses under different doses and schedules are modeled to estimate the effect of VEGF-C axis engagement on junctional patency and fluidic function. In an illustrative implementation, a physics-informed graph state-space model 304 (as in Embodiment 8) represents TM and SC compartments with latent states for VEGF-C signaling, junctional integrity, and permeability, subject to constraints linking junctional status to resistance. The model outputs: (i) estimated facility and permeability at time t; (ii) $\Delta$facility over a prespecified window; and (iii) predicted intraocular-pressure trajectories under standard physiologic assumptions—each with calibrated (coverage-guaranteed) uncertainty sets.

9.9.6 Uncertainty—Gated Experiment Design and Simulation

When the uncertainty set for a target (e.g., $\Delta$facility over the window of interest) exceeds a predefined threshold, the engine proposes minimal additional measurements predicted to reduce epistemic uncertainty efficiently, for example, a targeted Raman band, an extra OCT time point, or a confirmatory molecular panel. The same model can simulate dose profiles, genotypes affecting VEGF-C/VEGFR3/PROX1 regulation, or co-therapies, and may recommend closed-loop adjustments subject to safety gates.

9.9.7 Therapeutic Exploration and Decision Rules

Pre-, co-, and post-steroid schedules of VEGF-C axis activation are compared against appropriate controls. Non-limiting decision rules include: (i) a statistically significant increase in facility and/or decrease in TEER under matched load; (ii) corroborating structural signatures—sustained junctional continuity with increased vacuole events consistent with controlled trans-endothelial passage, without barrier failure; and (iii) molecular evidence of VEGFR3/PROX1 engagement with acceptable off-target profiles. Safety criteria may set a TEER floor and a maximum allowable increase in permeability for solute surrogates, alongside viability and innate-immune markers. Combination strategies (e.g., TM-directed ALK5 attenuation with SC-directed VEGF-C activation) are quantified for additivity/synergy and schedule optimization (order and spacing vs. steroid pulses), all under safety gates.

9.9.8 Prospective Validation and Acceptance Criteria

Predicted dose-schedule regimens are executed on fresh devices under matched $\Delta$P and shear, with pre-specified acceptance criteria (illustratively, mean absolute facility error$\leq 15\%$ over 24 h across $\geq 6$ chips). Deviations beyond tolerance are localized to exposure (PK at the interface), mechanism (collateral pathway compensation), or preprocessing/constraints and are followed by change-controlled updates with full lineage.

9.9.9 Cross-Platform Comparability, Explainability, and Governance

Comparability is maintained through harmonized calibration, geometry-aware normalization, and explicit reporting of operating windows and metadata. Each recommendation is accompanied by local feature attributions and counterfactuals (what measurement or dose change would reverse an unfavorable prediction). Versioned model artifacts and drift monitoring on Raman and imaging features support transparency, safety, and regulatory readiness.

9.9.10 Scope

All parameter ranges, materials, and component placements are illustrative and non-limiting. Functionally equivalent agents, delivery methods, sensors, and operating windows fall within the scope so long as inputs are time-stamped, normalized, and co-registered to $\Delta$P and shear.

10. Examples-Calibration, Mechanistic Perturbation, and Dose-Schedule Optimization Under Load in an Ocular MPS

10.1 Example 1: Baseline Facility Calibration and Raman-TEER Fusion Under $\Delta$P Ramp (Working; Non-Limiting)

Purpose. Establish baseline facility and apparent permeability under load, and verify Raman-TEER fusion and $\Delta$P-Q linearity prior to challenge.

Setup. Ocular MPS conditioned to baseline; media at 37° C. with viscosity recorded; TEER electrodes placed as specified; Raman 785 nm ($\approx 4\text{-}10$ cm$^{-1}$ resolution, $\leq 5$ mW at the sample); $\Delta$P ramp $0\rightarrow 2\rightarrow 4\rightarrow 6$ mmHg (illustrative), shear held$\approx 1\text{-}2$ dyn$\cdot$cm$^{-2}$. Timing follows FIG. 9; calibration/QA follow FIG. 4.

Procedure (illustrative).

1. Verify QA gates (TEER blank, Raman 520.7 cm$^{-1}$ reference, OCT scale/focus if used, off-cell $\Delta$P-Qr2>0.98).
2. Apply stepped $\Delta$P ramp; acquire synchronized Q, TEER (with frequency/area), and Raman spectra at each plateau; log geometry and temperature.
3. Repeat once for reproducibility; document drift (<10%/ 30 min). Use n$\geq 3$ devices where feasible.

Signals & features. $\Delta$P-Q traces; TEER ($\Omega\cdot$cm$^2$); Raman band indices; geometry (w, h, L), membrane thickness/porosity.

Derived quantities. Facility $C=Q/\Delta P$; hydraulic conductivity $L\_p=Q/(A\cdot\Delta P)$; TEER=$(R\_sample-R\_blank)\cdot A$.

AI engine(s) & outputs. Physics-informed regression with Kalman/state-space smoothing to produce baseline C, P_app, and drift-corrected series with CIs; conformalized residuals for coverage. (See FIG. 16 and Table 10: "Baseline facility & permeability under load".)

Acceptance & QA. Off-cell $\Delta$P-Q $r^2\geq 0.98$; coverage within +5% of nominal; baseline TEER/Raman drift<10%/ 30 min.

Reporting. Tabulate C vs. ΔP, TEER vs. time, Raman indices; attach QC plots and uncertainty intervals; record model/artifact versions.

10.2 Example 2: ALK Modulation with Time-Lapse TEER, ΔP-Q, Raman (Working; Non-Limiting)

Purpose. Quantify ALK-biased junctional tightening and resistance change under corticosteroid exposure (with/without ALK5 attenuation).

Setup. Baseline-verified chip; shear≈0.5-5 dyn·cm$^{-2}$ (illustrative); ΔP≈2-6 mmHg; dexamethasone dose/timing per protocol; optional ALK5 inhibitor arm; OCT or microscopy for junction metrics.

Procedure (illustrative).

1. Start exposure (dexamethasone vs. vehicle±ALK5 inhibitor).
2. Acquire continuous ΔP-Q and TEER; scheduled Raman spectra; imaging at defined time points (e.g., 0, 15, 30, 60, 120 min).
3. Maintain safety gates (ΔP, shear, laser power/dwell, current density); hold run if QC drifts exceed bounds.

Signals & features. pSMAD2/3 (snapshots), Raman band ratios, junction continuity/tortuosity, TEER, facility trajectory.

AI engine(s) & outputs. Graph state-space network (physics-informed) with image/spectral encoders; outputs time-series of junction integrity, permeability, and resistance; calibrated Δfacility over a prespecified window. (See Table 10: "Junctional remodeling under steroid challenge"; "Pathway attribution (ALK5 vs. VEGFC)".)

Uncertainty-gated add-ons. If predictive-set width for Δfacility>τ_C, schedule extra Raman band(s), or an additional imaging time point.

Acceptance & QA. Mean absolute facility error≤15% over 24 h across≥6 chips (illustrative); calibrated coverage within +5%; consistent directionality of pSMAD2/3 with functional tightening.

Reporting. Overlay facility/TEER/Raman trajectories; show attributions (which features drove predictions); record dose, schedule, geometry, and QC.

10.3 Example 3: Pharmaceutical Regimen Optimization (Prophetic; Non-Limiting)

In silico screening and chip assays identify two ALK5 inhibitors that improve barrier integrity and outflow facility while meeting predefined safety and acceptance thresholds.

Purpose. Demonstrate a screening-to-optimization workflow in which candidate pharmacologic modulators of TGFβ/ALK5 signaling are prioritized in silico and then verified on-chip, with model-guided dose scheduling and taper coordination.

Setup. An ocular microphysiological system (MPS) is conditioned to baseline facility and TEER. Raman (785 nm, ≤5 mW at sample) and OCT are co-registered to the MPS field of view. Two small-molecule ALK5 inhibitors (I-1 and I-2) are prepared in matched vehicles. A glucocorticoid challenge is optionally applied to reduce junction integrity prior to treatment. Acquisition timing follows FIG. 9; calibration/QA follow FIG. 4.

Procedure (illustrative).

1. In silico prioritization. Graph/state-space and QSAR/knowledge models (see FIG. 13) score candidates by predicted impact on junction descriptors and facility, subject to safety constraints.
2. On-chip screening. Apply I-1 and I-2 across a dose range (e.g., 3-4 levels) with vehicle controls and n≥3 replicates per condition; record TEER, Raman spectra, and OCT time-series under ΔP ramps and controlled shear (see FIG. 12).
3. Model-guided optimization. Fit dose-response surfaces and update the controller's priors; select schedules that maximize predicted facility restoration and junction integrity subject to Acceptance Metrics (FIG. 16, Table 10).

Analytics & Endpoints.

Primary: TEER increase vs. pre-dose and vehicle; facility restoration under ΔP ramp; OCT-derived junction continuity.

Secondary: Raman features consistent with tighter junction states; run stability and drift limits; safety gates (laser power, current density, thermal budget).

Decision rule: a candidate proceeds if it meets or exceeds the Acceptance Metrics (repeatability, agreement, classifier performance) summarized in FIG. 16 and Table 10.

Illustrative outcome. Both I-1 and I-2 surpass the TEER and facility gates; I-1 shows a faster onset while I-2 provides broader robustness across shear setpoints. The controller selects a schedule for I-1 with shorter pulses and for I-2 with longer duty cycles, each coordinated with steroid tapering.

Clinical mode (cross-reference to Embodiment 5). In eyes with an endothelial-integrated Schlemm's canal stent, the implant is treated as a standardized scaffold and controllable actuator. OCT/OCTA are registered to the stent's arc and micropore lattice; the AI maps sector-wise junction descriptors to predicted outflow contribution; and the engine outputs concrete control schedules (e.g., drug-elution timing/duty cycle or micro-valve/reservoir settings) coordinated with steroid tapering. Implant QA specifications (e.g., micropore density, endothelial coverage) can be ingested as priors while claim breadth is maintained by placing novelty on the analytics and control layer.

10.4 Example 4: VEGF-C Dosing Schedule with Washout; Facility and Raman Response (Prophetic; Non-Limiting)

Purpose. Evaluate VEGF-C axis activation on SC junctional patency and facility, including onset/offset dynamics with washout.

Setup. Baseline-verified chip; ΔP..2-6 mmHg; shear≈0.5-5 dyn·cm$^{-2}$; recombinant VEGF-C (mature form) at low-pM→low-nM equivalents; schedule variants: pre-, co-, or post-steroid; defined washout phase.

Procedure (illustrative).

1. Apply VEGF-C for a defined dosing interval (T_dose); record ΔP-Q and TEER continuously; collect Raman and imaging at scheduled time points.
2. Initiate washout; continue acquisitions to capture decay kinetics.
3. Optional antagonist/NRP2-block arm to test specificity.

Signals & features. VEGFR3/PROX1 markers (snapshots), Raman indices of junction/ECM, vacuole/pore metrics, TEER, facility.

AI engine(s) & outputs. Physics-informed graph state-space model 304 plus hierarchical Bayesian PK/PD linkage to estimate Δfacility (t), ED50/ECso posteriors, and optimal dose/schedule; calibrated IOP trajectory projections. (See Table 10: "Dose response & schedule optimization" and "Active experiment design".)

Uncertainty-gated add-ons. If posterior uncertainty on $EC_{50}$ or Δfacility remains above thresholds (t_R, τ_C), propose next-best measurement set (targeted Raman bands, extra OCT time point) while respecting safety gates.

Acceptance & QA. Significant increase in facility and/or decrease in TEER vs. baseline under matched load; corroborating structural signatures (increased vacuoles without barrier failure); drift and calibration within QA bounds.

Reporting. Dose-response curves with credible intervals; schedule comparisons (onset/washout); counterfactuals (dose or timing change needed to achieve target Δfacility); full lineage/versioning.

TABLE 16

| Operating Ranges (TEER, ΔP-Q, Raman, OCT/OCTA, Safety) | | | |
|---|---|---|---|
| Module | Typical settings | Report as | Acceptance/safety notes |
| TEER/Impedance | Sweep 100-10,000 Hz or fixed ~12.5 Hz; blank-subtracted; area-normalized | $\Omega \cdot cm^2$; % drift over 30 min | <10% baseline drift; specify electrode geometry & frequency |
| Pressure-Flow (ΔP-Q) | ΔP ramp 0-10 mmHg; Q = 0.1-20 μL · min⁻¹ | C = Q/ΔP; R_h = ΔP/Q | Linear fit $r^2 > 0.98$ (no cells); viscosity/geometry reported |
| Shear over TM | $\tau \approx$ 0.5-5 dyn · cm⁻² (adjustable 0.1-20) | dyn · cm⁻² (or Pa) | State channel w,h; compute $\dot{\gamma} \approx 6Q/(wh^2)$ |
| Raman (Spontaneous) | 785 nm; 4-10 cm⁻¹ res.; <5 mW at sample; 0.1-2 s/px | Peak positions/areas/ ratios; map stats | No peak drift beyond calibration; verify no photothermal change |
| Raman (SERS/SRS/CARS) | SERS: substrate away from flow path; SRS/CARS: CH-stretch imaging + point Raman | Spectral images/features | No obstruction of transport; co-register to baseline |
| OCT/OCTA & Microscopy | B-scans across TM-SC; en-face for vacuoles/pores; optional OCTA | Pore density/size; vacuole rate; lumen patency | Co-register to ΔP/τ timestamps; document objective/NA |
| Environment | 37° C.; humidified; CO₂ optional | Setpoint logs | Stable within ±0.5° C.; note medium viscosity |
| Safety | Laser power/dwell; electrode current density; max ΔP | Limits & exposure budget | Document limits per run; stop on deviation |

TABLE 17

| Abbreviations - ALK/VEGFC and Related Pathways (Extended) | | | | |
|---|---|---|---|---|
| Abbreviation | Full Name | Also Known As/ Gene | Type | Notes |
| ALK | Activin receptor-like kinase | Family of TGF-β superfamily type I receptors | Serine/threonine kinase receptors (Type I) | Not the oncogenic anaplastic lymphoma kinase (a distinct RTK). |
| ALK5 | Activin receptor-like kinase 5 | TGF-β receptor type I; gene: TGFBR1 | Serine/threonine kinase receptor (Type I) | Canonical mediator of TGF-β/SMAD2/3 signaling; promotes junctional tightening in TM context. |
| TGFBR1 | Transforming growth factor-β receptor 1 | Same protein as ALK5; gene: TGFBR1 | Serine/threonine kinase receptor (Type I) | Interchangeable with ALK5 in this specification. |
| VEGFC | Vascular endothelial growth factor C | VEGFR3 (FLT4) Ligand for | Secreted growth factor (ligand) | Supports lymphatic-like SC endothelial identity; associated with junctional patency. |
| VEGFR3 | Vascular endothelial growth factor receptor 3 | FLT4 | Receptor tyrosine kinase (RTK) | Primary receptor for VEGF-C/-D; linked to PROX1 program in SC endothelium. |
| SMAD2/3 | SMAD family members 2 and 3 | SMAD2; SMAD3 | Signal transducers/ transcription factors | Canonical downstream effectors of TGF-β/ALK5; form complexes with SMAD4 to regulate gene expression. |

TABLE 17-continued

| | | Also Known As/ | | |
|---|---|---|---|---|
| Abbreviation | Full Name | Gene | Type | Notes |
| RhoA/ROCK | RhoA GTPase and Rho-associated coiled-coil kinases | RHOA; ROCK1/ROCK2 | Small GTPase and serine/threonine kinases | Non-canonical branch of TGF-β; increases actomyosin tone and stress fibers, supporting junctional tightening. |
| TEER | Trans-epithelial/Trans-endothelial electrical resistance | — | Barrier integrity metric (electrical) | Area-normalized resistance (e.g., $\Omega \cdot cm^2$) used to quantify monolayer integrity and permeability inversely. |
| ΔP-Q | Pressure-flow relationship | Pressure drop (ΔP) and volumetric flow (Q) | Fluid-dynamic pair/facility metric | Facility C = Q/ΔP; used with viscosity and geometry to infer resistance and permeability. |
| AKT/ERK | AKT (Protein kinase B) and ERK (extracellular signal-regulated kinase) | AKT1/AKT2/AKT3; ERK1/ERK2 = MAPK3/MAPK1 | Serine/threonine kinases (PI3K-AKT and MAPK pathways) | Common VEGFR3 downstream nodes that support survival, junctional remodeling, and shear adaptation. |
| PROX1 | Prospero homeobox protein 1 | PROX1 | Transcription factor | Key regulator of lymphatic-like identity in SC endothelium; linked to VEGFC/VEGFR3 signaling. |
| eNOS | Endothelial nitric-oxide synthase | NOS3 | Enzyme (oxidoreductase) | Shear-responsive NO production; modulates vascular tone and junctional behavior on the SC side. |

TABLE 18

| | | | | | Notes/ |
|---|---|---|---|---|---|
| Investigation Focus | Primary Signals/ Features | AI Engine(s) | Key Outputs | Uncertainty & Decision Logic | Operating Windows |
| Baseline facility & permeability under load | TEER/impedance (area-normalized); ΔP-Q traces; viscosity-adjusted flow; geometry (w, h, L) | Physics-informed regression; Kalman/ state-space smoothing | Facility C; apparent permeability Papp; drift-corrected baseline with CIs | Conformalized residuals; alert if CI width > τC or ΔP-Q non-linearity ($r^2 < 0.98$) | ΔP ≈ 2-6 mmHg (adj. 0-20); shear ≈ 0.5-5 dyn · cm$^{-2}$ (adj. 0.1-20) |
| Junctional remodeling under steroid challenge | OCT/OCTA frames (vacuoles, pores); microscopy junction metrics; Raman band ratios; pSMAD2/3; VEGFC | Graph state-space network with image/spectral encoders; physics constraints | Time-courses of junction integrity, permeability, resistance | Coverage-guaranteed propose extra prediction sets; imaging or Raman bands if epistemic width > τJ | Co-registered to ΔP and shear; windowed analysis (e.g., 5-15 min) |
| Pathway attribution ALK5 vs | pSMAD2/3; VEGFC/VEGFR3/ PROX1; Raman | Structured causal graph/SEM; multitask | Pathway activity scores; contributions | Jackknife+ conformal for calibrated | Report with assay timestamps |

TABLE 18-continued

AI Anaylysis Focus - Investigation ↔ Engine Mapping (Illustrative and Non-Limiting)

| Investigation Focus | Primary Signals/ Features | AI Engine(s) | Key Outputs | Uncertainty & Decision Logic | Notes/ Operating Windows |
|---|---|---|---|---|---|
| VEGFC balance) | indices; TEER/AP-Q | classifiers with SHAP attributions | to resistance change | probabilities; counterfactual queries ('what-if') | and batch- normalization factors |
| Dose-response & schedule optimization (steroids, ALK5 inhibitors, VEGFC supplementation) | Dose/time vectors; facility/ permeability trajectories; safety markers | Hierarchical Bayesian PK/PD; Gaussian-process response surfaces | ED50/EC50 posteriors; optimal dose/ schedule proposals | Expected improvement; EHVI; safety-constrained optimization | Supports topical, intracameral, depot routes; device-agnostic |
| Active experiment design to reduce uncertainty | Model entropy/variance; candidate measurement menus (Raman bands, OCT time points, panels) | Bayesian optimization; constrained contextual bandits (Thompson sampling) | Next-best measurement set; projected uncertainty reduction | Stop/go when predictive-set width < thresholds ($\tau$C, $\tau$R) | Respects safety gates: laser power/dwell, current density, max $\Delta$P/shear |
| Cross-platform normalization and comparability | TEER frequency/area; Raman 520.7 cm$^{-1}$ reference; OCT scale; geometry/porosity metadata | Batch-effect correction (e.g., ComBat); domain adaptation | Harmonized feature space enabling pooled analyses | Drift monitors (EWMA/KL divergence); two-sample tests for shift | Metadata schema required; device details logged |
| Image/OCT feature extraction | B-scans, en face sequences; lumen patency; vacuole count/size; membrane deformation | UNet/CNN encoder + morphology; optical-flow for dynamics | Quantitative descriptors feeding GSSN/ regressors | Bootstrap CIs; calibration curves for derived counts | Resolution/ focus verified; voxel-to-$\mu$m scaling logged |
| Raman biochemical indexing | Spectra (e.g., 785 nm; 4-10 cm$^{-1}$); baseline-corrected bands; power/dwell metadata | Sparse regression (LASSO/elastic-net); manifold embedding | Band-integrated biochemical indices; junction/ ECM signatures | Permutation tests for band significance; interval coverage checks | Silicon 520.7 cm$^{-1}$ reference; power limits per safety gates |
| Responder classification (treatment efficacy) | Pre/post facility; junction metrics; pathway scores; genotype modifiers | Penalized GLMs/ gradient-boosted trees; stacked with GSSN outputs | Probability of response; odds ratios for covariates | Platt/Isotonic calibration; decision thresholds by utility | Chip-to-chip random effects via mixed models |
| Risk stratification/ time-to-event (e.g., IOP elevation) | Baseline imaging; pathway scores; exposure history | Cox/piecewise-exponential survival; Bayesian survival | Hazard ratios; predicted time-to-threshold | Brier/IBS calibration; prediction intervals | Optional for translational/ clinical use |
| Drift, anomaly, and QC monitoring | Feature distributions over time; $\Delta$P-Q linearity; TEER/Raman baseline drift | Unsupervised change-point detection; control charts; two-sample tests | Alerts and holds; auto-recalibration prompts | Guardrails block actuation when out of tolerance | Narrative Per QA (illustrative) |
| CRISPR/gene-therapy design & evaluation (optional) | Sequence features; off-target scores; chip-level rescue metrics | Sequence-to-function transformers; RL guide design; digital-twin simulator | Shortlisted constructs with predicted rescue/risk | Posterior update loop with experiment feedback | Vector payload/ tropism noted; segregate TM vs SC delivery |

Notes: Table 18 is illustrative and non-limiting. Engines and thresholds may be tuned to device geometry, assay sensitivity, and intended use.

Singular includes plural unless context requires otherwise. Ranges prefaced by "about" or "approximately" include manufacturing/measurement tolerances. Claim terms such as "comprising" are open-ended. References to an MPS or AO-MPS are non-limiting and do not restrict the invention to any single device architecture.

While the above description focuses on human embodiments, the system and techniques could be applied to veterinary implementations in the eyes of various animals.

Those skilled in the art will appreciate that the exemplary embodiments and descriptions thereof are merely illustrative of the inventions as a whole. Any dimensions used herein are for example, and any dimension may be modified without changing the scope of the claims. While the principles of the inventions have been made clear in the exemplary embodiments, it will be obvious to those skilled in the art that modifications of the structure that modifications of the structure, arrangement, proportions, elements, and materials may be utilized in the practice of the inventions, which are particularly adapted to specific environments and operative requirements without departing from the principles of the inventions.

LISTING OF DRAWING ELEMENTS

102 Ocular MPS system
104 ocular MPS
106 sensors/readouts
108 synchronization
110 AI engine
112 outputs
202 Schlemm's canal microchannel
204 Raman
206 upstream tap
208 downstream tap
210 imaging window
212 trabecular meshwork chamber
214 trabecular meshwork chamber
216 porous membrane interface
218 inlet
220 outlet
222 upstream tap
224 downstream tap
226 OCT/OCTA
228 TEER electrodes
230 TEER electrodes
302 hydrodynamic program
304 physics-informed graph state-space model
306 decision layer
308 TEER
310 $\Delta$P-Q (pressure flow)
312 OCT/OCTA
314 Raman spectra
316 device-agnostic encoders
318 shared latent
320 outputs
402 block
404 block
406 block
408 block
410 block
412 block
414 block
502 imaging window
504 shear
506 top channel
508 trabecular meshwork cell layer
510 ECM scaffold
512 porous membrane
514 Schlemm's canal endothelium
516 Schlemm's canal Lumen (bottom channel)
518 electrode
520 OCT/OCTA beam
522 upstream tap
524 downstream tap
526 $\Delta$P (pressure drop)
528 imaging window
602 top electrode
604 bottom electrode
606 TEER path
702 interrogation spot
704 near-infrared (785 nm) source 706 spectrometer
708 backscatter
802 en face field
804 cross-section
806 B-scan 1
808 B-scan 2
810 B-scan 3
812 B-scan 4
814 B-scan 5
816 B-scan 6
902 synchronized feature matrix
904 $\Delta$P
906 Q
908 TEER
910 Raman
912 imaging
914 Omics
1102 calibration checks
1104 drift windows
1106 if any fail then DEFER
1108 all pass then admit data
1110 all pass then admit data
1202 facility/permeability
1302 Schlemm's canal node
1304 Schlemm's canal node
1306 trabecular meshwork node
1308 constraints
1310 outputs
1312 time to
1314 time t1
1316 time t2
1318 Schlemm's canal node
1402 hydrodynamic load
1404 TGF$\beta$→ALK5/TGF$\beta$R1
1406 SMAD2/3 ($\pm$RhoA/ROCK)
1408 trabecular meshwork stiffening and junction tightening
1410 decreasing permeability/facility (c)
1412 VEGFC→VEGFR3 ($\pm$NRP2)
1414 AKT/ERK, PROX1 ($\pm$eNOS)
1416 Schlemm's canal junction patency
1418 increasing permeability/facility (c)
1420 agnostic balance
1502 predicted v measured facility
1504 uncertainty coverage
1506 baseline drift
1602 calibration pass
1604 drift within band
1606 coverage<=threshold
1608 safety limits satisfied
1610 Any checks fail→DEFER
1612 all checks passed→execute control/advance regimen
1702 OCT/OCTA volume
1704 sector-wise descriptors
1706 controller schedules
1708 implant QA priors
1710 uncertainty and tolerability gates
1712 coordinated with a steroid taper
1802 biological pathway
1804 steroid exposure/TGF$\beta$ context
1806 TM ALK5 (TGF$\beta$R1) activation→SMAD2/3
1808 TM secretome shift
1810 SC VEGFR3/NRP2 signaling reduced
1812 SC endothelial junctions tighten (increase actin belt, VE-cadherin clustering)
1814 decrease permeability/increase outflow resistance

1816 increase Intraocular pressure (glaucoma like)
1818 AI integration and decision support
1820 data acquisition
1822 modularity-specific encoders
1824 physics-informed graph state-space model
1826 calibration (temperature/isotonic)
1828 risk and permeability forecasts
1830 decision layer (uncertainty-gated)
1832 active learning loop
1902 AC source
1904 electrode/lead resistance
1906 channel/medium resistance
1908 TM layer resistance
1910 membrane resistance
1912 SC channel resistance
1914 junction/membrane capacitance
2002 block
2004 block
2006 block
2008 block
2010 block
2012 block
2014 block
2016 block
2018 block
2102 tear film
2104 cornea
2106 aqueous humor
2108 depot/implant
2110 conjunctiva/sclera
2112 TM/SC
2114 vitreous (opt.)
2202 current posterior
2204 gate check
2206 all gates pass
2208 update model
2210 any gate fails
2212 candidate set
2214 feasibility
2216 acquire measurement

The invention claimed is:

1. A method for measuring, forecasting, and modulating aqueous outflow, comprising:

providing an ocular microphysiological system reproducing a trabecular-meshwork-membrane-Schlemm's-canal interface operating under a defined hydrodynamic program comprising time-varying pressure-drop and shear waveforms generated by modulating the aqueous outflow through a microchannel;

acquiring, during execution of the defined hydrodynamic program, synchronized multimodal signals from said ocular microphysiological system including transepithelial/endothelial resistance (TEER) resistance, pressure-flow measurements, optical coherence tomography/optical coherence tomography angiography (OCT/OCTA) images, and Raman spectra;

encoding said multimodal signals into a device-agnostic feature representation comprising descriptors of junction continuity, belt thickness, tortuosity, pathway activity, and outflow-resistance proxies;

executing a physics-informed graph state-space model that fuses the device-agnostic feature representation into inferred parameters, the inferred parameters are inferred from barrier integrity, permeability, and outflow facility subject to monotonic constraints between structural and hydraulic variables, where the physics-informed graph state-space model includes a graph neural network and a physics-based constraint;

quantifying uncertainty from the inferred parameters;

generating calibrated forecasts of aqueous outflow performance; and controlling a drive actuator according to the calibrated forecasts when the uncertainty and the calibrated forecasts, satisfy a safety gate criterion.

2. The method of claim 1, wherein the defined hydrodynamic program imposes a pressure drop of 0-10 mm Hg and shear stress of 0.5-5 dyn·cm$^{-2}$.

3. The method of claim 1, further comprising performing electrical calibration and optical wavelength calibration prior to acquisition.

4. The method of claim 1, wherein the Raman spectra are acquired with near-infrared excitation and spectral resolution of 4-10 cm$^{-1}$.

5. The method of claim 1, wherein the physics-informed graph state-space model represents trabecular-meshwork and Schlemm's-canal compartments as coupled nodes exchanging mechanical and biochemical messages.

6. The method of claim 1, wherein monotonic constraints enforce that increases in junction continuity or VEGFC signaling decrease hydraulic resistance, and increases in ALK5 signaling increase hydraulic resistance.

7. The method of claim 1, wherein the quantifying of uncertainty employs conformal prediction to establish coverage probabilities.

8. The method of claim 1, further comprising an active-learning controller that selects a next measurement configuration when uncertainty exceeds a defined threshold.

9. The method of claim 1, wherein the safety gate criteria restrict at least one of laser power, electrode current density, and maximum pressure drop.

10. The method of claim 1, wherein the ocular microphysiological system includes a porous membrane between trabecular-meshwork and Schlemm's canal chambers fabricated from a polycarbonate.

11. The method of claim 1, further comprising normalizing heterogeneous device outputs from cross-MPS (microphysiological systems) into a common latent space.

12. The method of claim 1, further comprising administering a pharmacologic intervention targeting ALK5/TGF-β pathways.

13. The method of claim 12, wherein the pharmacologic intervention includes administering a corticosteroid challenge and forecasts facility recovery under an ALK5 inhibitor regimen.

14. The method of claim 1, further comprising storing the device-agnostic feature representation, the inferred parameters, calibrated forecasts, model version, calibration record, and gate outcomes.

15. A system for multimodal measurement, forecasting, and modulation of aqueous outflow, comprising:

an ocular microphysiological device including:

a trabecular-meshwork compartment, a porous membrane, and a Schlemm's canal channel with inlet and outlet ports;

a plurality of synchronized sensors connected to the ocular microphysiological device, the plurality of synchronized sensors configured to measure calibration, transepithelial/endothelial resistance (TEER), pressure-flow pairs, optical coherence tomography/optical coherence tomography angiography (OCT/OCTA) data, and Raman spectra into synchronized sensor data;

a timing hub configured to align the synchronized sensor data to a common clock into a multimodal feature set;

a computing module executing a physics-informed graph state-space model trained to infer uncertainty, barrier integrity, permeability, and outflow facility from the multimodal feature set into model forecasts, where the physics-informed graph state-space model includes a graph neural network and a physics-based constraint; and a controller configured to control a drive actuator based on the model forecasts when the calibration and the uncertainty satisfy a safety gate criterion.

16. The system of claim 15, wherein the computing module applies device-agnostic encoders normalizing geometry, temperature, and sampling cadence.

17. The system of claim 15, wherein the drive actuator comprises a dosing pump configured for closed-loop regulation of pressure and flow.

18. The system of claim 15, further comprising a calibration subsystem performing transepithelial/endothelial resistance (TEER) blank correction, Raman wavelength alignment, and optical coherence tomography (OCT) scale verification.

19. The system of claim 15, wherein the physics-informed graph state-space model includes monotone constraints coupling junction features to hydraulic resistance.

20. The system of claim 15, wherein uncertainty and safety gates are implemented as acceptance metrics for coverage, drift, and power thresholds.

21. The system of claim 15, wherein the ocular microphysiological device further includes optical windows allowing simultaneous optical coherence tomography/optical coherence tomography angiography (OCT/OCTA) and Raman interrogation.

22. The system of claim 15, further comprising a data logger that records calibration artifacts, model parameters, and control histories for regulatory audit.

23. The system of claim 15, wherein the computing module executes active-learning logic selecting a next-best measurement.

24. The system of claim 15, wherein the plurality of synchronized sensors and the controller are network-connected to permit federated learning across multiple laboratory or clinical sites.

25. A non-transitory computer-readable medium storing instructions that, when executed by one or more processors coupled to a pump actuator, cause the one or more processors to:

receive calibration and synchronized electrical, hydraulic, optical, and spectroscopic data from an ocular microphysiological system;

encode the synchronized electrical, hydraulic, optical, and spectroscopic data into device-agnostic features;

apply a physics-informed graph state-space model on the device-agnostic features to estimate barrier integrity, permeability, and outflow facility with uncertainty, where the physics-informed graph state-space model includes a graph neural network and a physics-based constraint; and actuate the pump actuator when the calibration and the uncertainty satisfy a safety gate criterion.

26. The non-transitory computer-readable medium of claim 25, wherein the instructions further cause adaptive updating of model parameters based on calibration results or longitudinal drift.

27. The non-transitory computer-readable medium of claim 25, wherein the physics-informed graph state-space model employs monotonicity regularization and causal constraints derived from fluid-structure relations.

28. The non-transitory computer-readable medium of claim 25, wherein quantification of the uncertainty uses Bayesian techniques to define prediction intervals.

29. The non-transitory computer-readable medium of claim 25, wherein the instructions interface with an electronic laboratory notebook to export standardized diagnostic reports.

30. The non-transitory computer-readable medium of claim 25, wherein the instructions further cause computation of ALK5 and VEGFC signaling indices from Raman or omics features to forecast therapeutic response.

*   *   *   *   *